US011786603B2

(12) United States Patent
Han et al.

(10) Patent No.: US 11,786,603 B2
(45) Date of Patent: Oct. 17, 2023

(54) OPTIMIZED TRANSGLUTAMINASE SITE-SPECIFIC ANTIBODY CONJUGATION

(71) Applicant: REGENERON PHARMACEUTICALS, INC., Tarrytown, NY (US)

(72) Inventors: Amy Han, Hockessin, DE (US); William Olson, Yorktown Heights, NY (US); Christopher D'Souza, Pomona, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/079,851

(22) PCT Filed: Feb. 24, 2017

(86) PCT No.: PCT/US2017/019537
§ 371 (c)(1),
(2) Date: Aug. 24, 2018

(87) PCT Pub. No.: WO2017/147542
PCT Pub. Date: Aug. 31, 2017

(65) Prior Publication Data
US 2019/0070306 A1 Mar. 7, 2019

Related U.S. Application Data

(60) Provisional application No. 62/300,727, filed on Feb. 26, 2016.

(51) Int. Cl.
A61K 47/68 (2017.01)
C07K 1/107 (2006.01)

(52) U.S. Cl.
CPC ...... *A61K 47/6803* (2017.08); *A61K 47/6883* (2017.08); *A61K 47/6889* (2017.08); *C07K 1/1072* (2013.01)

(58) Field of Classification Search
None
See application file for complete search history.

(56) References Cited

U.S. PATENT DOCUMENTS

| 5,156,956 | A | 10/1992 | Motoki et al. |
| 5,731,183 | A | 3/1998 | Kobayashi et al. |
| 5,948,662 | A | 9/1999 | Kobayashi et al. |
| 6,010,871 | A | 1/2000 | Takahara et al. |
| 6,100,053 | A | 8/2000 | Bech et al. |

(Continued)

FOREIGN PATENT DOCUMENTS

| WO | WO 03/060073 A2 | 7/2003 |
| WO | WO 2013/176516 A1 | 11/2013 |

(Continued)

OTHER PUBLICATIONS

US 8,420,094 B2, 04/2013, Seed et al. (withdrawn)

(Continued)

*Primary Examiner* — Karl J Puttlitz
(74) *Attorney, Agent, or Firm* — SQUIRE PATTON BOGGS (US) LLP

(57) ABSTRACT

Provided herein are methods and compositions for site-specific conjugation of antibodies in the presence of a transglutaminase.

32 Claims, 24 Drawing Sheets
Specification includes a Sequence Listing.

(56) References Cited

U.S. PATENT DOCUMENTS

| | | | |
|---|---|---|---|
| 6,322,996 | B1 | 11/2001 | Sato et al. |
| 6,620,916 | B1 | 9/2003 | Takahara et al. |
| 6,927,050 | B1 | 8/2005 | Hampp et al. |
| 7,396,656 | B2 | 7/2008 | Lin et al. |
| 7,485,438 | B2 | 2/2009 | Chou |
| 8,198,418 | B2 | 6/2012 | Kamiya et al. |
| 8,524,241 | B2 | 9/2013 | Seed et al. |
| 8,586,532 | B2 | 11/2013 | Buchardt et al. |
| 8,859,629 | B2 | 10/2014 | van Delft et al. |
| 8,993,295 | B2 | 3/2015 | Seed et al. |
| 9,388,454 | B2 | 7/2016 | Kamiya et al. |
| 9,688,777 | B2 | 6/2017 | Kamiya et al. |
| 2003/0138785 | A1 | 7/2003 | Kopytek et al. |
| 2006/0110782 | A1 | 5/2006 | Bertozzi et al. |
| 2009/0264366 | A1 | 10/2009 | Johansen et al. |
| 2010/0104589 | A1 | 4/2010 | Govindan et al. |
| 2011/0184147 | A1 | 7/2011 | Kamiya et al. |
| 2013/0122020 | A1 | 5/2013 | Liu et al. |
| 2013/0189287 | A1 | 7/2013 | Bregeon et al. |
| 2013/0230543 | A1 | 9/2013 | Pons et al. |
| 2014/0113832 | A1 | 4/2014 | Wolfe et al. |
| 2014/0356385 | A1 | 12/2014 | Dennler et al. |
| 2015/0111246 | A1 | 4/2015 | Samant et al. |
| 2015/0165064 | A1 | 6/2015 | Bregeon et al. |
| 2015/0284713 | A1 | 10/2015 | Fischer et al. |
| 2016/0022833 | A1* | 1/2016 | Bregeon ............ A61K 47/6803 530/391.1 |
| 2016/0193356 | A1 | 7/2016 | Farias et al. |
| 2016/0214917 | A1 | 7/2016 | Van Delft et al. |
| 2017/0043033 | A1 | 2/2017 | Strop et al. |
| 2017/0362330 | A1 | 12/2017 | Liu et al. |
| 2018/0037921 | A1 | 2/2018 | Rao-Naik et al. |
| 2018/0071402 | A1* | 3/2018 | Bregeon ............... A61K 47/60 |
| 2018/0140714 | A1 | 5/2018 | Dashin et al. |
| 2018/0360793 | A1* | 12/2018 | Hu ..................... A61K 47/6855 |
| 2019/0194344 | A1* | 6/2019 | Piater .................... C07K 16/00 |

FOREIGN PATENT DOCUMENTS

| | | | |
|---|---|---|---|
| WO | 2015162563 | * | 10/2015 |
| WO | WO 2015/162563 A1 | | 10/2015 |
| WO | WO 2016/144608 A1 | | 9/2016 |

OTHER PUBLICATIONS

Dennler et al., Biooconjugate Chemistry, vol. 25, No. 3, Mar. 19, 2014 (Mar. 19, 2014), pp. 569-578 (Year: 2014).*

Josten et al., "Use of microbial transglutaminase for the enzymatic biotinylation of antibodies", Journal of Immunological Methods, 2000, vol. 240, pp. 47-54.

Kamiya et al., "Site-specific cross-linking of functional proteins by transglutamination", Publication Enzyme and Microbial Technology, 2003, vol. 33, pp. 492-496.

LHOSPICE et al., "Site-Specific Conjugation of Monomethyl Auristatin E to Anti-CD30 Antibodies Improves Their Pharmacokinetics and Therapeutic Index in Rodent Models", Molecular Pharmaceutics, 2015, vol. 12, pp. 1863-1871, DOI: 10.1021/mp500666j.

LHOSPICE et al., ADC Summit, San Francisco on Oct. 15, 2013, "Towards Homogenous ADCs: A New Site Specific Antibody Conjugation Using Bacterial Transglutaminase", Innate Pharma, 29 pages.

LHOSPICE et al., ADC Summit, San Francisco, Oct. 15-16, 2013, "Towards Homogenous ADCs: A New Site Specific Antibody Conjugation Using Bacterial Transglutaminase", Innate Pharma, poster, 1 page.

Pasternack et al., "TA fluorescent substrate of transglutaminase for detection and characterization of glutamine acceptor compounds" Analytical Biochemistry, 1997, vol. 249, pp. 54-60.

Jeger, Simone "Site-specific conjugation of tumour-targeting antibodies using transglutaminase", 2009, ETH Zurich, Research Collection, Doctoral Thesis, 141 pages.

Takazawa et al., "Enzymatic labeling of a single chain variable fragment of an antibody with alkaline phosphatase by microbial transglutaminase", Biotechnology and Bioengineering, May 20, 2004, vol. 86, No. 4, pp. 399-404.

International Search Report and the Written Opinion in PCT/US2017/019537 dated Aug. 31, 2017, 17 pages.

Dennler et al., "Transglutaminase-Based Chemo-Enzymatic Conjugation Approach Yields Homogeneous Antibody-Drug Conjugates", Bioconjugate Chemistry, Mar. 19, 2014, vol. 25, No. 3, pp. 569-578.

Jeger et al., "Site-Specific and Stoichiometric Modification of Antibodies by Bacterial Transglutaminase", Angewandte Chemie International Edition, 2010, vol. 49, No. 51, pp. 9995-9997 and Supporting Information, 46 pages.

Klinguer-Hamour et al., "World Antibody-Drug Conjugate Summit, Oct. 15-16, 2013, San Francisco, CA", mAbs 6:1, pp. 18-29; Jan./Feb. 2014; http://doi.org/10.4161/mabs.27437.

Lin and Ting, "Transglutaminase-Catalyzed Site-Specific Conjugation of Small-Molecule Probes to Proteins in Vitro and on the Surface of Living Cells", J. Am. Chem. Soc. 2006, vol. 128, pp. 4542-4543.

Mindt et al., "Modification of Different IgG1 Antibodies via Glutamine and Lysine using Bacterial and Human Tissue Transglutaminase", Bioconjugate Chem. 2008, vol. 19, pp. 271-278.

Perez et al., "Antibody-drug conjugates: current status and future directions", Drug Discovery Today, vol. 19, No. 7, Jul. 2014, pp. 869-881.

Strop et al., "Location Matters: Site of Conjugation Modulates Stability and Pharmacokinetics of Antibody Drug Conjugates", Chemistry & Biology, Feb. 21, 2013, vol. 20, pp. 161-167.

Strop, "Versatility of Microbial Transglutaminase", Bioconjugate Chem. 2014, vol. 25, pp. 855-862.

* cited by examiner

| Lane | Sample |
|---|---|
| 1 | Standards (Bench Mark 10 µL) |
| 2 | Naked anti-HER2 |
| 3 | Deglycosylated anti-HER2 |
| 4 | Deglycosylated anti-HER2-PEG$_3$-N$_3$ |
| 5 | Deglycosylated anti-HER2-PEG$_3$-LP1 |
| 7 | Naked anti-HER2 (reduced) |
| 8 | Deglycosylated anti-HER2 (reduced) |
| 9 | Deglycosylated anti-HER2-PEG$_3$-N$_3$ (reduced) |
| 10 | Deglycosylated anti-HER2-PEG$_3$-LP1 (reduced) |

| Lane | Sample |
|---|---|
| 1 | Standards (Bench Mark 10 μL) |
| 2 | Anti-PRLR aglycosylated antibody |
| 4 | Anti-PRLR mAb + 5U MTG/mg mAb + 0 equiv. $H_2N$-$PEG_3$-$N_3$ |
| 5 | Anti-PRLR mAb + 5U MTG/mg mAb + 20 equiv. $H_2N$-$PEG_3$-$N_3$ |
| 6 | Anti-PRLR mAb + 5U MTG/mg mAb + 100 equiv. $H_2N$-$PEG_3$-$N_3$ |
| 7 | Anti-PRLR mAb + 5U MTG/mg mAb + 200 equiv. $H_2N$-$PEG_3$-$N_3$ |
| 8 | Anti-PRLR mAb + 5U MTG/mg mAb + 500 equiv. $H_2N$-$PEG_3$-$N_3$ |

| | | α-PRLR mAb/ADC captured (RU) | 40 nM hPRLR bound (RU) | $k_a$ (l/mol*s) | $k_d$ (1/s) | $K_D$ (mol/l) | $t_{1/2}$ (min) | $K_D$ ADC / $K_D$ Ab |
|---|---|---|---|---|---|---|---|---|
| PRLR monomer | | | | | | | | |
| Anti-PRLR | Parent Ab | 211 | 69 | 2.20E+06 | 3.17E-04 | 1.44E-10 | 36 | |
| | 4DAR ADC | 224 | 70 | 1.79E+06 | 3.13E-04 | 1.75E-10 | 37 | 1.2 |
| | | α-ErbB2 mAb/ADC captured (RU) | 50 nM hErbB2 bound (RU) | $k_a$ (l/mol*s) | $k_d$ (1/s) | $K_D$ (mol/l) | $t_{1/2}$ (min) | $K_D$ ADC / $K_D$ Ab |
| ErbB2 monomer | | | | | | | | |
| Anti-ErbB2 | Parent Ab | 126 | 52 | 1.22E+05 | 3.74E-04 | 3.07E-09 | 31 | |
| | 4DAR ADC | 124 | 43 | 1.43E+05 | 2.90E-04 | 2.03E-09 | 40 | 0.7 |

FIG. 7

| ADC/mAb/Payload | DAR | mAb conjugation site | Target | Linker-Payload* | % kill on T47D | EC50 (nM) on T47D |
|---|---|---|---|---|---|---|
| Site Specific ADC | 4 | PRLR mAb #1, N297Q | PRLR | 1 | 63 | 0.6 |
| Non-Site Specific ADC | 3.9 | PRLR mAb #1, Random | PRLR | 2 | 67 | 0.9 |
| Site Specific ADC | 4 | FelD1 mAb, Q295, Q297 | FelD1 | 1 | 4 | NA |
| Site Specific ADC | 2 | PRLR mAb #2, Q295 | PRLR | 1 | 45 | 0.6 |
| Non-Site Specific ADC | 1.9 | PRLR mAb #2, Random | PRLR | 2 | 50 | 1.2 |
| Non-Site Specific ADC | 2.2 | FelD1 mAb, Random | FelD1 | 2 | 4 | NA |
| Site Specific mAb | NA | PRLR mAb #1, N297Q | NA | NA | 1 | NA |
| Non-Site mAb | NA | PRLR mAb #2, Random | NA | NA | 1 | NA |
| MMAE | NA | NA | NA | NA | 78 | 0.2 |

*: Linker-Payload 1 : DIBACT-PEG$_4$-VC-pAB-MMAE; Linker-Payload 2 : MC-VC-pAB-MMAE

FIG. 9 (Cont.)

| Lane | Sample |
|---|---|
| 1 | Standards (Bench Mark 10 µL) |
| 2 | mAb |
| 3 | mAb + mTGase pH 7.97 |
| 4 | mAb + Azido + mTGase pH 5.87 |
| 5 | mAb + Azido + mTGase pH 6.07 |
| 6 | mAb + Azido + mTGase pH 6.35 |
| 7 | mAb + Azido + mTGase pH 6.92 |
| 8 | mAb + Azido + mTGase pH 7.51 |
| 9 | mAb + Azido + mTGase pH 7.88 |
| 10 | mAb + Azido + mTGase pH 8.56 |

~2 µg of reduced sample/lane.
Novex 4 - 20% 'WedgeWell' Tris-Glycine Gel;
1.0 mm x 10 well, 180 V, 300 mA, 70 min.
BenchMark Pre-Stained Protein Ladder, Invitrogen,
cat# 10748-010; L# 1803297.

| Amine-Substrate | Eq. to Ab | TG conc. (U/mg of Ab) | pH | Temp. (°C) | Rxn. Time (Hrs) | DAR | Cross-link product |
|---|---|---|---|---|---|---|---|
| Azido-dPEG₃-amine | 35 | 0.5 | 7.8 | 37 | 24 | 0.3 | |
| Azido-dPEG₃-amine | 35 | 1 | 7.8 | 37 | 24 | 0.6 | |
| Azido-dPEG₃-amine | 35 | 5 | 7.8 | 37 | 24 | | |
| Azido-dPEG₃-amine | 35 | 5 | 7.8 | 25 | 24 | 1.1 | |
| Azido-dPEG₃-amine | 35 | 5 | 7.8 | 37 | 24 | | |
| Azido-dPEG₃-amine | 10 | 5 | 7.8 | 37 | 24 | | |
| Azido-dPEG₃-amine | 20 | 5 | 7.8 | 37 | 24 | | |
| Azido-dPEG₃-amine | 35 | 5 | 7.8 | 37 | 24 | | |
| Azido-dPEG₃-amine | 85 | 5 | 7.8 | 37 | 24 | | |
| Azido-dPEG₃-amine | 85 | 5 | 7.2 | 37 | 24 | 1.7 | |
| Azido-dPEG₃-amine | 200 | 5 | 7.6 | 37 | 24 | | |
| Azido-dPEG₃-amine | 200 | 5 | 7.8 | 37 | 24 | | |
| Azido-dPEG₃-amine | 275 | 5 | 8 | 37 | 24 | 1.3 | |
| Azido-dPEG₃-amine | 200 | 5 | 7.8 | 37 | 24 | | |
| Azido-dPEG₃-amine | 200 | 5 | 7.8 | 37 | 24 | | |
| Azido-dPEG₁₁-amine | 200 | 5 | 7.8 | 37 | 24 | | |

FIG. 16

OPTIMIZED TRANSGLUTAMINASE SITE-SPECIFIC ANTIBODY CONJUGATION

CROSS-REFERENCE TO RELATED APPLICATIONS

This application is a National Stage filing under 35 USC § 371 of PCT/US2017/019537 filed Feb. 24, 2017, which claims priority to, and the benefit of U.S. Provisional Application No. 62/300,727, filed Feb. 26, 2016, the contents of all of which are incorporated herein by reference in their entireties.

FIELD

Provided herein are methods, antibody conjugates, and pharmaceutical compositions for use in therapy, for example, for the treatment of cancer. In certain embodiments, methods are provided for specific and efficient cross-linking of a linker and/or payload to one or more antibody glutamine side chain amide groups.

BACKGROUND

Antibody conjugates utilize the selective binding of an antibody to deliver a payload to targets within tissues of subjects. The payload can be a therapeutic moiety that is capable of taking action at the target. To date, at least three antibody-drug conjugates have been approved for use in humans in markets such as the United States and Europe. Brentuximab vedotin is an antibody with specificity for the cell-surface protein CD30 and conjugated to the cytotoxic drug monomethyl auristatin (MMAE). Brentuximab vedotin is approved in the U.S. and Europe for the treatment of Hodgkin lymphoma and refractory systemic anaplastic large cell lymphoma. Trastuzumab emtansine is an antibody with specificity for the HER2 receptor and conjugated to the cytotoxic maytansanoid drug DM1. Trastuzumab emtansine is approved in the U.S. and Europe for the treatment of HER2 positive metastatic breast cancer. As of the date of the present disclosure, over 45 unique antibody-drug conjugates (ADCs) are or have been in clinical trials (Rostami et al., 2014, *ADC Review*).

Several techniques for conjugating linkers and payloads to antibodies are available. Many conjugates are prepared by non-selective covalent linkage to cysteine or lysine residues in the antibody. This non-selective technique can result in a heterogeneous mixture of products with conjugations at different sites and with different numbers of conjugations per antibody. Additional techniques for site-specific modification of antibodies are in early development including site-directed mutagenesis of antibody chains (Axup et al., 2012, *Proc. Natl. Acad. Sci. USA* 109:16101-16106) and linking to glutamine side chains with the enzyme transglutaminase (Dennler et al., 2014, *Bioconjug. Chem.* 25:569-578). Since transglutaminase preferably recognizes a single wild-type antibody heavy chain residue, glutamine 295 (Gln295), transglutaminase conjugation should provide homogeneous products with site-specific linkers and high drug-to-antibody ratios (Dennler et al., supra). As certain antibodies have two heavy chains and two Gln295 residues, transglutaminase antibody conjugation is capable of providing an antibody with conjugates on each Gln295 residue with a drug to antibody ratio (DAR) of up to 2.0, the theoretical maximum (Dennler et al., supra). Higher DARs are possible in antibodies with additional glutamine residues. However, undesirable side products are described herein, likely cross-linking a Gln295 residue to another residue in another chain, with higher than expected molecular weights. It is believed that this side product forms from the cross-linking of a Gln295 to a lysine residue or to a terminal amine.

As promising as transglutaminase conjugation might be, the reaction is far from optimized. Any improvement in the reaction can result in increased purity and efficiency in the production of antibody-drug conjugates. In particular, reaction processes are needed that minimize or eliminate the high molecular weight side products.

SUMMARY

Provided herein are compositions and methods for site-specific conjugation of antibodies. In certain embodiments, the compositions and methods provide for efficient conjugation of antibodies. In certain embodiments, the compositions and methods provide antibody conjugate compositions with little or no side product.

In one aspect, provided herein are methods for the preparation of a glutaminyl-modified antibody. The methods comprise the step of contacting an antibody with a primary amine compound in the presence of transglutaminase at a pH between about 7.6 and about 7.8 under conditions sufficient for a reaction of the primary amine compound with the antibody. In certain embodiments, the antibody is not glycosylated. Generally, the antibody comprises at least one glutamine residue, for instance, heavy chain Gln295. In certain embodiments, the methods provide a product composition with little or no side product. The present disclosure is based, in part, on the discovery that a pH between about 7.6 and about 7.8 minimizes the amount of side product in the reaction. In additional embodiments, the methods further comprise reaction of the glutaminyl-modified antibody with a reactive linker-payload compound, reactive linker compound, or reactive payload compound to form an antibody-payload conjugate.

In another aspect, provided herein are methods for the preparation of a glutaminyl-modified antibody including the step of treating a deglycosylated or aglycosylated antibody with a primary amine in the presence of transglutaminase at a reaction pH between about 7.0 and about 8.0. In certain embodiments, the antibody is not glycosylated. Generally, the antibody comprises at least one glutamine residue, for instance, heavy chain Gln295. In certain embodiments, the methods provide a product composition with little or no side product. Certain embodiments are based, in part, on the discovery that a reaction pH of between about 7.0 and about 8.0 minimizes the amount of side product in the reaction. In additional embodiments, the methods further comprise reaction of the glutaminyl-modified antibody with a reactive linker-payload compound, reactive linker compound, or reactive payload compound to form an antibody-payload conjugate.

In another aspect, provided herein are compositions for the preparation of a glutaminyl-modified antibody. In certain embodiments, provided herein are the products of any of the methods of the present disclosure. In certain embodiments, provided herein are compositions comprising a glutaminyl-modified antibody and little or no side product. In certain embodiments, provided herein are compositions comprising an antibody-payload conjugate and little or no side product. In certain embodiments, provided herein are compositions comprising an antibody without glycosylation, transglutaminase, a primary amine compound, and a buffer providing a pH of about 7.6 to about 7.8.

The methods and compositions provided herein are useful for the preparation of antibody-payload conjugates linked through one or more glutamine residues. The conjugates can be used for any purpose known to those of skill in the art including for diagnostics and therapy, for example, the treatment of one or more cancers.

BRIEF DESCRIPTION OF THE FIGURES

FIG. 2A shows Coomassie-stained SDS-PAGE gel analysis of parent antibody, deglycosylated antibody, azido-functionalized antibody, and anti-HER2-LP1 (ADC) under non-reducing and reducing conditions. For example, FIG. 2B shows Coomassie-stained SDS-PAGE gel analysis of aglycosylated anti-PRLR-LP1 (ADC) and its intermediates.

FIG. 7 shows binding kinetics for antibodies and conjugates (LP1-ADCs) to human antigens (PRLR.mmh and ErbB2.mmh).

FIG. 16 shows a summary of conjugation results with optimized conditions.

DESCRIPTION OF EXEMPLARY EMBODIMENTS

Figure 1:
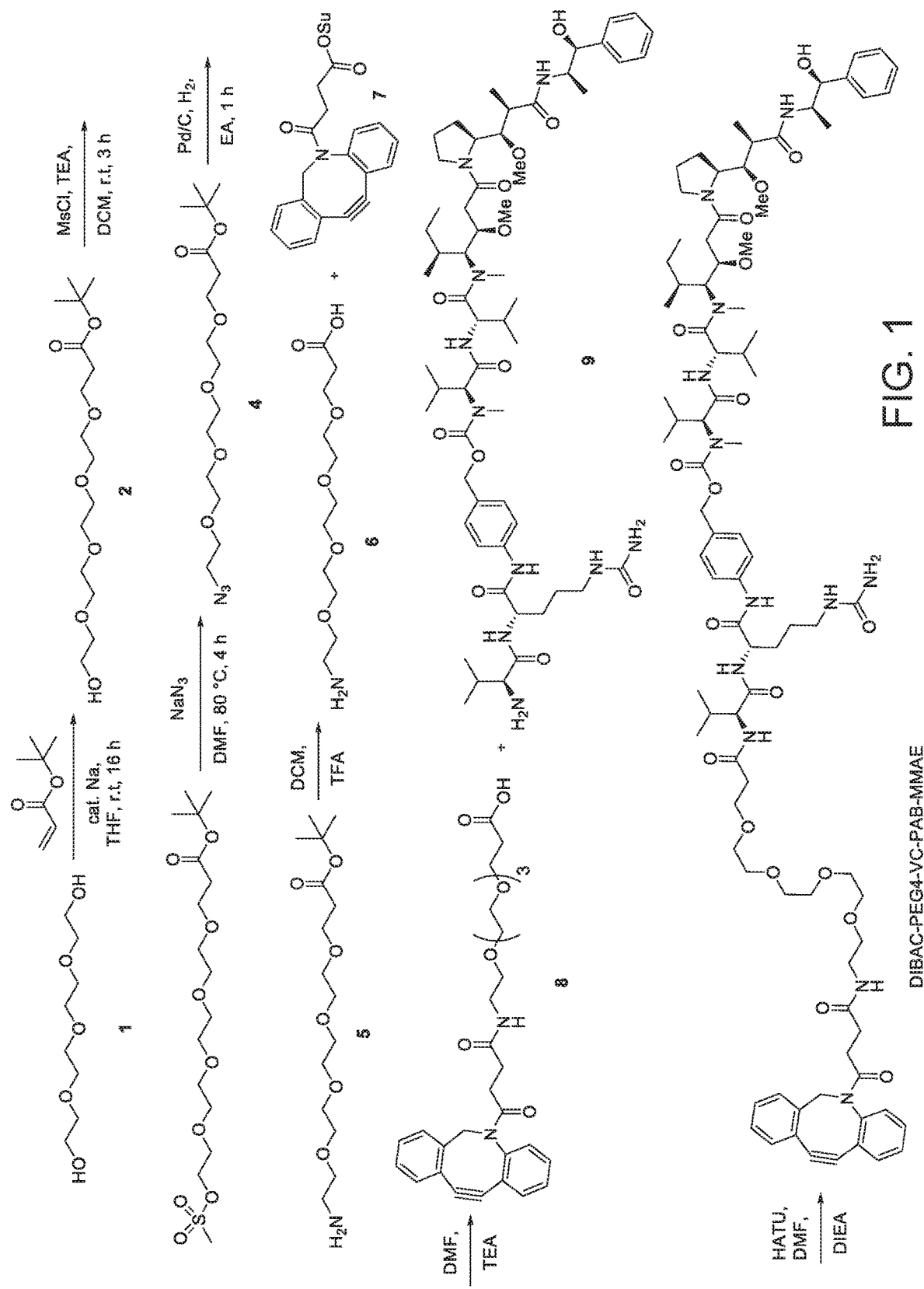
FIG. 1 shows a schematic depicting a synthetic route for producing DIBAC-Suc-PEG$_4$-VC-PAB-MMAE.

Provided herein are methods of making glutaminyl-modified antibodies and antibody conjugates, compositions for use in the methods, and compositions produced by the methods. The conjugates are useful for diagnostics and therapy, for instance, in the treatment of one or more cancers.

The references to certain embodiments made in the following description are considered illustrative only of the principles of the disclosure. Further, since numerous modifications and changes will readily be apparent to those skilled in the art, it is not intended to limit the disclosure to the exact construction and process shown as described herein. Accordingly, all suitable modifications and equivalents may be resorted to as falling within the scope of the disclosure and as defined by the claims that follow.

Definitions

When referring to the methods and compositions provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The words "comprise," "comprising," "include," and "including," when used in this specification and in the following claims are intended to specify the presence of the stated features, integers, components, or steps, but they do not preclude the presence or addition of one or more additional features, integers, components, or steps thereof.

The term "alkyl," as used herein, refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to, methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

The term "heteroalkyl," as used herein refers to an alkyl in which one or more carbon atoms are replaced by heteroatoms. Suitable heteroatoms include, but are not limited to, nitrogen, oxygen, and sulfur atoms.

The term "antibody," as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers.

Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present description include: (i) $V_H$—$C_H1$; (ii) $V_H$—$C_H2$; (iii) $V_H$—$C_H3$; (iv) $V_H$—$C_H1$—$C_H2$; (V) $V_H$—$C_H1$—$C_H2$—$C_H3$; (vi) $V_H$—$C_H2$—$C_H3$; (vii) $V_H$—$C_L$; (viii) $V_L$—$C_H1$; (ix) $V_L$—$C_H2$; (x) $V_L$—$C_H3$; (xi) $V_L$—$C_H1$—$C_H2$; (xii) $V_L$—$C_H1$—$C_H2$—$C_H3$; (xiii) $V_L$—$C_H2$—$C_H3$; and (xiv) $V_L$—$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids which result in a flexible or semi-flexible linkage between adjacent variable and/or constant domains in a single polypeptide molecule.

Moreover, an antigen-binding fragment of an antibody of the present description may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present description using routine techniques available in the art.

The antibodies of the present description may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the description in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) *Proc. Natl. Acad. Sci.* (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the antibodies of the description are human antibodies. The term "human antibody," as used herein, is intended to include antibodies having variable and constant regions derived from human germline immunoglobulin sequences. The human antibodies of the description may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies may, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (See, e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human lgG4 hinge can significantly reduce the appearance of the second form (Angal et al. (1993) Molecular Immunology 30: 105) to levels typically observed using a human lgG1 hinge. The instant description encompasses antibodies having one or more mutations in the hinge, $C_H2$ or $C_H3$ region which may be desirable, for example, in production, to improve the yield of the desired antibody form.

The antibodies of the description may be isolated or purified antibodies. An "isolated antibody" or "purified antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present description. For example, an antibody that has been purified from at least one component of a reaction or reaction sequence, is a "purified antibody" or results from purifying the antibody. An isolated antibody also includes an antibody in situ within a recombinant cell. Isolated antibodies are antibodies that have been subjected to at least one purification or isolation step. According to certain embodiments, an isolated antibody or purified antibody may be substantially free of other cellular material and/or chemicals.

The antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present description includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present description may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, improved drug-to-antibody ratio (DAR) for antibody-drug conjugates, etc. Antibodies and antigen-binding fragments obtained in this general manner are encompassed within the present description.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "aglycosylated antibody" refers to an antibody that does not comprise a glycosylation sequence that might interfere with a transglutamination reaction, for instance an antibody that does not have saccharide group at N297 on one or more heavy chains. In particular embodiments, an antibody heavy chain has an N297 mutation. In other words, the antibody is mutated to no longer have an asparagine residue at position 297 according to the EU numbering system as disclosed by Kabat et al. In particular embodiments, an antibody heavy chain has an N297Q or an N297D mutation. Such an antibody can be prepared by site-directed mutagenesis to remove or disable a glycosylation sequence or by site-directed mutagenesis to insert a glutamine residue at site apart from any interfering glycosylation site or any other interfering structure. Such an antibody also can be isolated from natural or artificial sources.

The term "deglyosylated antibody" refers to an antibody in which a saccharide group at N297 was removed, thereby opening Q295 to transglutamination. In particular embodiments, provided herein are processes that encompass an additional step of deglycosylating an antibody, for instance an N297 antibody.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "conjugated antibody" refers to an antibody covalently linked to one or more chemical moieties. The chemical moiety can include a linker, a reactive linker, a payload, a reactive payload, a reactive linker-payload, or combinations thereof. Linkers and payloads are described in detail herein. In particular embodiments, a conjugated antibody is an antibody-drug conjugate (ADC), an antibody-payload conjugate, or an antibody-linker-payload conjugate.

The term "glutaminyl-modified antibody" refers to an antibody with at least one covalent linkage from a glutamine side chain to a chemical moiety. The chemical moiety can be any moiety deemed suitable by the practitioner of skill. In particular embodiments, the chemical moiety is linked through an amide linkage on the glutamine side chain.

The phrase "pharmaceutically acceptable amount" refers to an amount effective or sufficient in treating, reducing, alleviating, or modulating the effects or symptoms of at least one health problem in a subject in need thereof. For example, a pharmaceutically acceptable amount of an antibody or antibody-drug conjugate is an amount effective for modulating a biological target using the antibody or antibody-drug-conjugates provided herein. Suitable pharmaceutically acceptable amounts include, but are not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of an antibody or antibody-drug-conjugate provided herein.

The phrase "initial pH" refers to the pH of a component or reactant for a reaction before the component or reactant is added to the reaction mixture. For example, the initial pH of a buffer solution is 7.74 before the buffer solution is added to a reaction mixture.

The phrase "reaction pH" refers to the pH of a reaction after all reaction components or reactants have been added.

The term "pharmaceutically acceptable" means approved by a regulatory agency of the United States Federal or State government or listed in the U.S. Pharmacopeia or other generally recognized pharmacopeia for use in animals, and more particularly in humans.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) *Science* 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the description to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

Methods

Provided herein are methods of making glutaminyl-modified antibodies, compositions useful in the methods, and compositions produced by the methods. Conjugated antibodies are useful in assays, diagnostics, and therapies, including the treatment of cancer in subjects in need thereof.

In certain embodiments, the methods comprise at least step (2) below.

The methods comprise a transglutaminase reaction at a glutamine residue of an antibody. The antibody can be any antibody known to those of skill in the art. Useful antibodies are described in a section below.

Those of skill will recognize that the antibody should comprise at least one glutamine residue. In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (See, e.g., Ausubel et al., *Current Protoc. Mol. Biol.*).

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra), and affect drug-to-antibody ratios (DARs). Accordingly, in advantageous embodiments, the antibody is not glycosylated. In certain embodiments, the antibody is deglycoslated or aglycosylated.

In a deglycosylation step, the antibody can be deglycosylated by any technique apparent to those of skill in the art. In particular embodiments, a deglyosylated antibody is prepared by removing one or more oligosaccharides from the antibody. The deglycosylation can be carried out by any technique apparent to those of skill. In certain embodiments, the antibody is deglycosylated chemically. In certain embodiments, the antibody is deglycosylated enzymatically. In certain embodiments, the antibody can be deglycosylated by expression in a system that does not glycosylate polypeptides. Useful expression systems include, for example, prokaryotic expression systems.

In certain embodiments, provided herein are methods comprising the following step:

(1) deglycosylating the antibody.

The antibody can be deglycosylated by any technique deemed suitable by those of skill in the art. In certain embodiments, the antibody is contacted with a reagent capable of cleaving a bond between the antibody and an oligosaccharide. The reagent can be any reagent known to those of skill in the art. In particular embodiments, the reagent is an enzyme capable of cleaving a bond between an asparagine side chain and an N-linked oligosaccharide. In preferred embodiments, the reagent is PNGase F, or peptide-N4—(N-acetyl-beta-glucosaminyl)asparagine amidase, or EC 3.5.1.52. Reagents such as PNGase F can be obtained from commercial sources. In certain embodiments, the reagent is Protein Deglycosylation Mix (New England Biolabs). The reagent is used in an amount suitable for the amount of glycosylated antibody and the reaction volume. In certain embodiments, about 10 units of reagent is used per about 1 μg of glycosylated antibody.

In step (1), the reaction is carried out under conditions suitable for cleaving the bond(s). The reaction is typically carried out in water or in buffered water. The pH of the reaction solution can be any pH deemed suitable for reaction. In certain embodiments, the reaction pH is from 7-8. In certain embodiments, the reaction pH is about 7.5, about. 7.6, about 7.7, about 7.8, about 7.9, or about 8.0. In particular embodiments, the reaction pH is about 7.8. The reaction can include any buffer capable of maintaining the desired pH. In certain embodiments, the reaction is in a solution of 50 mM ammonium bicarbonate buffer at a pH of about 7.8. In some embodiments, the reaction includes BupH buffer. The reaction can take place at any temperature deemed suitable by the practitioner of skill. Reaction volume is any volume deemed suitable by those of skill in the art. In useful embodiments, reaction volume is from about 10 μl to about 1 ml. In certain embodiments, the reaction takes place at room temperature or elevated temperatures. In particular embodiments, the reaction takes place at 37° C. The reaction can be carried out for any length of time necessary for the reaction to proceed to the desired level of completion. In certain embodiments, the reaction proceeds for 1-48 hours. In certain embodiments, the reaction proceeds for 1, 2, 3, 4, 5, 6, 7, 8, 9, 10, 15, 20, 25, 30, 35, 40, or 45 hours. The reaction can be monitored by standard techniques such as SDS-PAGE, western blotting, mass spectrometry, and the like.

In certain embodiments, the deglycosylated antibody is isolated from the reaction mixture. The deglycosylated antibody can be isolated by any technique deemed suitable by those of skill. In particular embodiments, the deglycosylated antibody can be isolated by size exclusion chromatography, affinity chromatography, filtration, centrifugal ultrafiltration, or any other technique deemed suitable.

The antibody without interfering glycosylation is then reacted with a primary amine compound. In certain embodiments, an aglycosylated antibody is reacted with a primary amine compound to produce a glutaminyl-modified antibody. In certain embodiments, a deglycosylated antibody is reacted with a primary amine compound to produce a glutaminyl-modified antibody. For the purposes of this description, the deglyosylated antibody can be obtained or produced from any source or by any technique deemed suitable by those of skill in the art. In certain embodiments, the antibody is deglycosylated according to step (1), above. In further embodiments, it is sufficient that the deglycosylated or aglycosylated antibody comprise at least one glutamine residue that is sufficiently free of interfering glycosylation, or other structures, to be available for reaction with transglutaminase, as described below.

The primary amine can be any primary amine that is capable of forming a covalent bond with a glutamine residue in the presence of a transglutaminase. Useful primary amines are described in a section below.

Accordingly, provided are methods of producing a glutaminyl-modified antibody comprising the step:
  (2) reacting an antibody with a sufficient amount of a primary amine compound in the presence of transglutaminase at a pH between about 7.6 and about 7.8 under conditions suitable for covalent coupling of the primary amine to a glutamine side chain in a polypeptide chain of the antibody. As discussed above, the antibody can be deglycosylated, aglycosylated, or otherwise free of interfering glycosylation.

In another embodiment, provided are methods for producing a glutaminyl-modified antibody comprising the step:
  (2a) treating an antibody with a sufficient amount of a primary amine compound in the presence of transglutaminase at a reaction pH between about 7.0 and about 8.0 under conditions suitable for covalent coupling of the primary amine to a glutamine side chain in a polypeptide chain of the antibody. As discussed above, the antibody can be deglycosylated, aglycosylated or otherwise free of interfering glycosylation.

In another embodiment, provided are methods for producing a glutaminyl-modified antibody comprising the steps of:
  (i) adding the deglycosylated antibody or aglycosylated antibody to a solvent;
  (ii) adding at least 25 molar equivalents of the primary amine compound;
  (iii) adding the transglutaminase at a pH such that the reaction pH is between about 7.0 and about 8.0; and
  (iv) mixing the final reaction mixture.

In another embodiment, step (iv) comprises mixing the final reaction mixture for at least 4 hours. In certain embodiments, step (iv) comprises stirring the final reaction mixture. In other embodiments, step (iv) comprises shaking the reaction mixture.

The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is a microbial transglutaminase. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In step (2) or step (2a), the reaction is typically carried out in a solvent. In certain embodiments, the solvent is selected from the group consisting of a water solution, such as a buffered solution or buffered water, saline water, buffered saline water, an organic solvent, water buffered with phosphate, HEPES, and MOPS. For example, in one embodiment, the solvent is BupH phosphate buffered saline. By way of further example, in one embodiment, the solvent is BupH phosphate buffered saline with an initial pH of 7.74. In certain embodiments, the pH of the reaction is determines the efficiency of the reaction (i.e., provides a useful DAR). For example, in certain embodiments, the final reaction pH determines the efficiency of the reaction (i.e., provides a useful DAR). The present disclosure is based, at least in part, on the discovery that a high molecular weight side product can contaminate tranglutaminase-catalyzed antibody reactions. Without being bound to any theory, it is believed that this high molecular weight side product comprises two or more antibody heavy chains, likely linked from a glutamine side chain on one heavy chain to an amine, for instance, a lysine side chain or a terminal amine, on the other heavy chain. In addition, without being bound to any particular theory, it is believed that a final reaction pH greater than 8.0 leads to cross-linking of two or more antibody heavy chains; and a final reaction pH less than 7.0 leads to stalling of the tranglutaminase-catalyzed antibody reactions. A person of skill in the art will appreciate that the transglutaminase is active within a wide pH range (pH 5-8). (See, e.g., *Appl. Microbiol. Biotechnol.* 2004, 64, 447-454). Transglutaminase (TG) catalyzes the formation of an isopeptide bond between the exposed glutamine on the antibody and a variety of primary amines. TG could also catalyze two side reactions: first—irreversible deamination to glutamic acid at higher pH; and second—if there is not enough amine substrate, covalent cross-linking of proteins could occur. As shown in the Examples below, reaction at a pH between about 7.0 and about 8.0 minimizes the amount of the high molecular weight side product while maintaining high ratios of conjugate to antibody, i.e., high drug to antibody ratios (DARs). As shown in the Examples below, reaction at a pH between about 7.6 and about 7.8 minimizes the amount of the high molecular weight side product while maintaining high ratios of conjugate to antibody, i.e., high drug to antibody ratios (DARs). In particular embodiments, the reaction pH is about 7.0. In particular embodiments, the reaction pH is 7.0. In particular embodiments, the reaction pH is 7.1. In particular embodiments, the reaction pH is 7.2. In particular embodiments, the reaction pH is 7.3. In particular embodiments, final reaction pH is 7.4. In particular embodiments, the reaction pH is 7.5. In particular embodiments, the reaction pH is 7.6. In particular embodiments, the reaction pH is 7.7. In particular embodiments, the reaction pH is between 7.6-7.8. In particular embodiments, the reaction pH is 7.8. In particular embodiments, the reaction pH is 7.9. In particular embodiments, the reaction pH is 8.0.

In particular embodiments, the pH of the reaction is about 7.6. In particular embodiments, the pH of the reaction is 7.6+/−0.05. In particular embodiments, the pH of the reaction is about 7.7. In particular embodiments, the pH of the reaction is 7.7+/−0.05. In particular embodiments, the pH of the reaction is about 7.8. In particular embodiments, the pH of the reaction is 7.8+/−0.05.

The pH buffer can be any buffer deemed suitable for maintaining a pH between about 7.6 and about 7.8, according to the person of skill. In certain embodiments, the buffer is selected from the group consisting of phosphate, phosphate buffered saline, HEPES (4-(2-hydroxyethyl)-1-piperazineethanesulfonic acid), and MOPS (3-(N-morpholino)propanesulfonic acid).

In the reaction of step (2) or step (2a), the antibody can be at any concentration deemed suitable to the practitioner of skill. In certain embodiments, the antibody is present at a concentration from 0.1 to 5 mg/ml. In particular embodiments, the antibody is present at a concentration of about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.5 mg/ml, about 3.0 mg/ml, about 3.5 mg/ml, about 4.0 mg/ml, about 4.5 mg/ml, or about 5.0 mg/ml.

The concentration of the primary amine compound can be any concentration deemed suitable by the practitioner of skill. In certain embodiments, the concentration of the primary amine compound is determines the efficiency of the reaction (i.e., provides a useful DAR).. As shown in the Examples below, the concentration of the primary amine compound can provide low amounts of high molecular weight side product and high DAR. In certain embodiments, the primary amine compound is at a concentration of at least about 34 molar equivalents, relative to the concentration of antibody. In certain embodiments, the primary amine compound is at a concentration of at least about 50 molar equivalents, relative to the concentration of antibody. In certain embodiments, the primary amine compound is at a concentration of at least about 75 molar equivalents, relative to the concentration of antibody. In certain embodiments, the primary amine compound is at a concentration of at least about 85 molar equivalents, relative to the concentration of antibody. In certain embodiments, the primary amine compound is at a concentration of at least about 100 molar equivalents, relative to the concentration of antibody. In certain embodiments, the primary amine compound is at a concentration of at least about 125 molar equivalents, relative to the concentration of antibody. In certain embodiments, the primary amine compound is at a concentration of at least about 150 molar equivalents, relative to the concentration of antibody. In certain embodiments, the primary amine compound is at a concentration of at least about 175 molar equivalents, relative to the concentration of antibody. In certain embodiments, the primary amine compound is at a concentration of at least about 200 molar equivalents, relative to the concentration of antibody. In certain embodiments, the primary amine compound is at a concentration of at least about 300 molar equivalents, relative to the concentration of antibody. In certain embodiments, the primary amine compound is at a concentration of at least about 400 molar equivalents, relative to the concentration of antibody. In certain embodiments, the primary amine compound is at a concentration of at least about 500 molar equivalents, relative to the concentration of antibody. In certain embodiments, the primary amine compound is at a concentration of at least about 600 molar equivalents, relative to the concentration of antibody. In certain embodiments, the primary amine compound is at a concentration of at least about 700 molar equivalents, relative to the concentration of antibody. In certain embodiments, the primary amine compound is at a concentration of at least about 800 molar equivalents, relative to the concentration of antibody. In certain embodiments, the primary amine compound is at a concentration of at least about 900 molar equivalents, relative to the concentration of antibody. In certain embodiments, the primary amine compound is at a concentration of at least about 1000 molar equivalents, relative to the concentration of antibody. Those of skill will recognize that the above ranges have an upper limit at the solubility of the primary amine compound. In certain embodiments, any of the above concentrations are less than about 500 molar equivalents or less than about 1000 molar equivalents.

The measure of U/mg deglycosylated antibody of transglutaminase can be any amount deemed suitable by the practitioner of skill. In certain embodiments, the transglutaminase is at about 0.5 to about 30 U/mg deglycosylated antibody. In certain embodiments, the transglutaminase is at about 0.5 to about 6 U/mg deglycosylated antibody. In certain embodiments, the transglutaminase is at about 1 to about 30 U/mg deglycosylated antibody. In certain embodiments, the transglutaminase is at least about 1.75 U/mg deglycosylated antibody. In certain embodiments, the transglutaminase is at about 2.2 U/mg deglycosylated antibody. In certain embodiments, the transglutaminase is at least about 2.5 U/mg deglycosylated antibody. In certain embodiments, the transglutaminase is at least about 3.5 U/mg deglycosylated antibody. In certain embodiments, the transglutaminase is at least about 5 U/mg deglycosylated antibody. In certain embodiments, the transglutaminase is at least about 10 U/mg deglycosylated antibody. In certain embodiments, the transglutaminase is at least about 25 U/mg deglycosylated antibody. In certain embodiments, the transglutaminase is at about 2.2 U/mg deglycosylated antibody for scale-up purposes.

The reaction of step (2) or step (2a) is carried out at any temperature deemed suitable by those of skill in the art. In particular embodiments, the reaction is conducted at any temperature from about 20° C. to about 40° C., from about 25° C. to about 40° C., or from about 25° C. to about 37° C. In particular embodiments, the reaction is at room temperature. In particular embodiments, the reaction is at about 25° C., about 30° C., about 35° C., or about 37° C.

The reaction of step (2) or step (2a) can be carried out in any volume deemed suitable by those of skill in the art and depends on the size of the reaction. In particular embodiments, the reaction volume is from about 10 µL to about 10 mL, from about 10 µL to about 5 mL, from about 10 µL to about 2.5 mL, from about 10 µL to about 1.0 mL, from about 10 µL to about 0.5 mL, from about 10 µL to about 250 µL, or from about 10 µL to about 100 µL.

The reaction of step (2) or step (2a) can proceed for any time deemed suitable for formation of the glutaminyl-modified antibody. In certain embodiments, the reaction proceeds for about 1 to about 48 hours. In particular embodiments, the reaction proceeds for about 1 hour, about 2 hours, about 3 hours, about 4 hours, about 5 hours, about 6 hours, about 6 hours, about 7 hours, about 8 hours, about 9 hours, about 10 hours, about 15 hours, about 20 hours, about 25 hours, about 30 hours, about 40 hours, or about 48 hours. In certain embodiments, the reaction proceeds for at least 4 hours, at least 18 hours, or at least 24 hours. Reaction progress can be monitored by standard techniques such as size-exclusion chromatography, mass spectrometry, MALDI, SDS-PAGE, Western blotting, and the like.

In certain embodiments, the glutaminyl-modified antibody is isolated or purified from the reaction mixture. The glutaminyl-modified antibody can be isolated or purified by any technique deemed suitable by those of skill. In particular embodiments, the glutaminyl-modified antibody can be isolated by chromatography, size-exclusion chromatography, affinity chromatography, or any other technique deemed suitable. For example, in one embodiment, the the glutaminyl-modified antibody is purified by affinity chromatography. By way of further example, in one embodiment, the glutaminyl-modified antibody is purified by protein A chromatography. By way of further example, in one embodiment, the glutaminyl-modified antibody is purified by affinity chromatography and protein A chromatography.

In certain embodiments, the reaction of step (2) or step (2a) provides little or no high molecular weight side product. The high molecular weight side product would be a high molecular weight species comprising two or more heavy chain groups covalently bonded in a reaction that depends on the transglutaminase and/or the final reaction pH. In certain embodiments, the reaction of step (2) or step (2a) provides a composition comprising no detectable side product based on inspection of a SDS-PAGE gel, via visual inspection, staining, and/or other detection methods. In certain embodiments, the reaction of step (2) or step (2a) provides a composition comprising less than 10% side product relative to desired glutaminyl-modified antibody. In certain embodiments, the reaction of step (2) or step (2a) provides a composition comprising less than 5% side product relative to glutaminyl-modified antibody. In certain embodiments, the reaction of step (2) or step (2a) provides a composition comprising less than 4% side product relative to glutaminyl-modified antibody. In certain embodiments, the reaction of step (2) or step (2a) provides a composition comprising less than 3% side product relative to glutaminyl-modified antibody. In certain embodiments, the reaction of step (2) or step (2a) provides a composition comprising less than 2% side product relative to glutaminyl-modified antibody. In certain embodiments, the reaction of step (2) or step (2a) provides a composition comprising less than 1% side product relative to glutaminyl-modified antibody. In certain embodiments, the reaction of step (2) or step (2a) provides a composition comprising less than 1% cross-linked antibody relative to glutaminyl-modified antibody. Relative amounts can be calculated on a mass or molar basis.

In certain embodiments, the primary amine compound comprises a reactive group capable of further reaction after transglutamination. In these embodiments, the glutaminyl-modified antibody can be reacted with a reactive payload compound or a reactive linker-payload compound to form an antibody-payload conjugate, or reacted with a reactive linker to form an antibody-linker conjugate, which can subsequently be transformed into an antibody-payload conjugate. The reactive payload compound, the reactive linker compound, or the reactive linker-payload compound should comprise a reactive group that is capable of reacting with the reactive group of the primary amine compound. In certain embodiments, the primary amine compound comprises an azide, and the reactive payload compound, the reactive linker compound, or the reactive linker-payload compound comprises an alkyne or cycloalkyne or other moiety that is capable of undergoing a 3+2 cycloaddtion reaction with an azide. In certain embodiments, the primary amine compound comprises an alkyne or cycloalkyne or other moiety that is capable of undergoing a 3+2 cycloaddition with an azide, and the reactive payload compound, the reactive linker compound, or the reactive linker-payload compound comprises an azide. In certain embodiments, the primary amine compound comprises a carboxyl, and the reactive payload compound, the reactive linker compound, or the reactive linker-payload compound comprises an amine. Examples of useful reactive payload compounds, reactive linker compounds, and reactive linker-payload compounds are described in a section below.

Accordingly, provided herein are methods comprising the following step:
(3) reacting or treating the glutaminyl-modified antibody with a reactive linker-payload compound to form an antibody-payload conjugate.

The reaction can proceed under conditions deemed suitable by those of skill in the art. In certain embodiments, the glutaminyl-modified antibody is contacted or treated with the reactive linker-payload compound under conditions suitable for forming a bond between the glutaminyl-modified antibody and the linker-payload compound. Suitable reaction conditions are well known to those in the art. Exemplary reactions are provided in the Examples below.

Additionally, provided herein are methods comprising the following step:
(3) reacting or treating the glutaminyl-modified antibody with a reactive payload compound to form an antibody-payload conjugate.

The reaction can proceed under conditions deemed suitable by those of skill in the art. In certain embodiments, the glutaminyl-modified antibody is contacted or treated with the reactive payload compound under conditions suitable for forming a bond between the glutaminyl-modified antibody and the payload. Suitable reaction conditions are well known to those in the art. Exemplary reactions are provided in the Examples below.

In certain embodiments, provided herein are methods comprising the following steps:
(3a) reacting or treating the glutaminyl-modified antibody with a reactive linker compound to form an antibody-linker conjugate; and
(3b) reacting or treating the antibody-linker conjugate with a reactive payload compound to form an antibody-payload conjugate.

The reaction can proceed under conditions deemed suitable by those of skill in the art. In certain embodiments, the glutaminyl-modified antibody is contacted or treated with the reactive linker compound under conditions suitable for forming a bond between the glutaminyl-modified antibody and the linker. In certain embodiments, the antibody-linker conjugate is contacted or treated with the reactive payload compound under conditions suitable for forming a bond between the antibody-linker conjugate and the payload. In certain embodiments, the reactive linker compound comprises a first reactive group that reacts with the reactive group of the primary amine compounds described herein, and a second reactive group that is capable of reacting with a reactive payload compound or reactive linker payload compound and is either (1) inert under the reaction conditions of step (3a) or (2) is protected with a protecting group to be inert under the reaction conditions of step (3a). Said protected second reactive group is deprotected and subjected to step (3b). Suitable reaction conditions and protecting group are well known to those in the art. Exemplary reactions are provided in the Examples below.

In certain embodiments, the antibody-payload conjugate is isolated or purified from the reaction mixture. The antibody-payload conjugate can be isolated or purified by any technique deemed suitable by those of skill. In particular embodiments, the antibody-payload conjugate can be isolated by size exclusion chromatography, affinity chromatography, filtration, or any other technique deemed suitable.

In certain embodiments, the reaction of step (3), (3a), or (3b) provides little or no side product. The side product would be a high molecular weight species comprising two or more heavy chain polypeptides covalently bonded to each other in a reaction that depends on the transglutaminase and/or the final reaction pH. In certain embodiments, the reaction of step (3), (3a), or (3b) provides a composition comprising less than 10% side product relative to antibody-payload conjugate. In certain embodiments, the reaction of step (3), (3a), or (3b) provides a composition comprising less than 5% side product relative to antibody-payload conjugate. In certain embodiments, the reaction of step (3), (3a), or (3b) provides a composition comprising less than 4% side product relative to antibody-payload conjugate. In certain embodiments, the reaction of step (3), (3a), or (3b) provides a composition comprising less than 3% side product relative to antibody-payload conjugate. In certain embodiments, the reaction of step (3), (3a), or (3b) provides a composition comprising less than 2% side product relative to antibody-payload conjugate. In certain embodiments, the reaction of step (3), (3a), or (3b) provides a composition comprising less than 1% side product relative to antibody-payload conjugate. Relative amounts can be calculated on a mass or molar basis.

Antibodies

In the present disclosure, the antibody can be any antibody deemed suitable to the practitioner of skill. In preferred embodiments, the antibody comprises at least one glutamine residue in at least one polypeptide chain sequence. In certain embodiments, the antibody comprises one or more Gln295 residues. In certain embodiments, the antibody comprises two heavy chain polypeptides, each with one Gln295 residue. In further embodiments, the antibody comprises one or more glutamine residues at a site other than a heavy chain 295. Such antibodies can be isolated from natural sources or engineered to comprise one or more glutamine residues. Techniques for engineering glutamine residues into an antibody polypeptide chain are within the skill of the practitioners in the art. In certain embodiments, the antibody is aglycosylated.

The antibody can be in any form known to those of skill in the art. In certain embodiments, the antibody comprises a light chain. In certain embodiments, the light chain is a kappa light chain. In certain embodiments, the light chain is a lambda light chain.

In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-1 and -II(IGF-I and IGF-II); des(I-3)-IGF-1 (brain IGF-1), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CDl8, an ICAM, VLA-4 and VCAM; a tumor associated antigen such as AFP, ALK, B7H4, BAGE proteins, β-catenin, brc-ab1, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides. In some embodiments, the antigen is a tumor antigens, including antigens specific for a type of tumor or antigens that are shared, overexpressed or modified on a particular type of tumor. Examples include, but are not limited to: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2. In some embodiments, the antigen is PRLR or HER2. In some embodiments, the antibody is an anti-PRLR or anti HER2 antibody.

Primary Amine Compounds

The primary amine compound can be any primary amine compound deemed useful by the practitioner for linking to the antibody. Generally, the primary amine compound has the formula H$_2$N—R, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. The reactive group and protected reactive group can be any group deemed suitable by the practitioner of skill. In certain embodiments, the reactive group is capable of forming a covalent bond in a reaction with a reactive payload compound, a reactive linker compound, or a reactive linker-payload compound, but inert in step (2) or step (2a) described herein. In certain embodiments, the protected reactive group is inert in step (2) or step (2a) described herein, and can be subsequently deprotected after performing step (2) or step (2a) to provide a reactive group suitable to react with the reactive group of the reactive linker-payload compound or reactive payload compounds described herein. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulthydryl, cycloalkyne, aldehyde, and carboxyl.

In certain embodiments, the primary amine compound is according to the formula H$_2$N-LL-X, where LL is a divalent spacer and X is a reactive group or protected reactive group.

In particular embodiments, LL is a divalent polyethylene glycol (PEG) group. In certain embodiments, X is selected from the group consisting of —SH, —N$_3$, alkyne, aldehyde, and tetrazole. In particular embodiments, X is —N$_3$.

In certain embodiments, the primary amine compound is according to one of the following formulas:

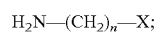

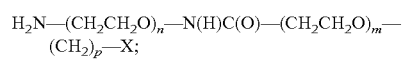

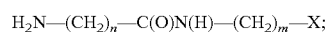

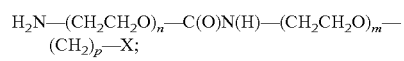

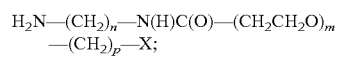

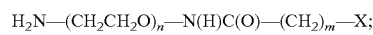

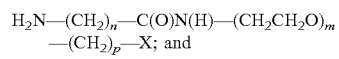

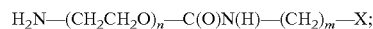

where n is an integer selected from 1 to 12;

m is an integer selected from 0 to 12;

p is an integer selected from 0 to 2;

and X is selected from the group consisting of —SH, —N$_3$, —C≡C$_H$, —C(O)H, tetrazole,

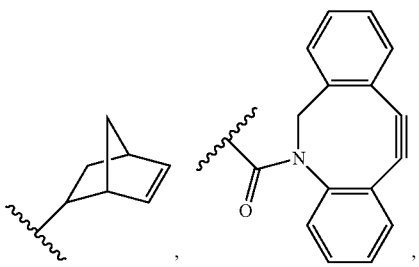

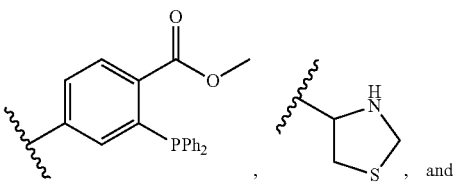

, and

23
-continued
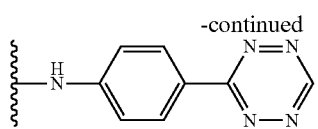
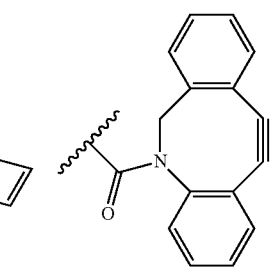
24
-continued
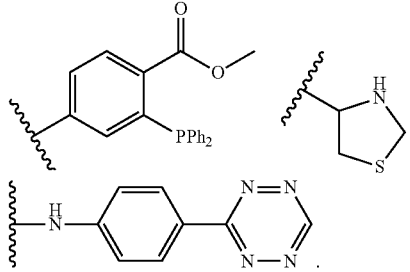
In the above, any of the alkyl (i.e., —CH$_2$—) groups can optionally be substituted, for example with C$_{1-8}$alkyl, methylformyl, or —SO$_3$H. In certain embodiments, the alkyl groups are unsubstituted.
In certain embodiments, the primary amine compound is selected from the group consisting of
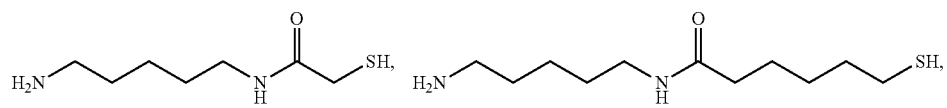
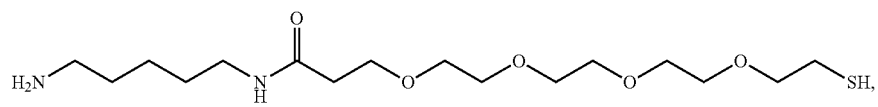
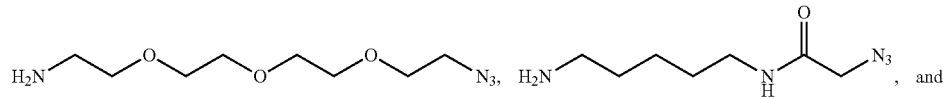
, and
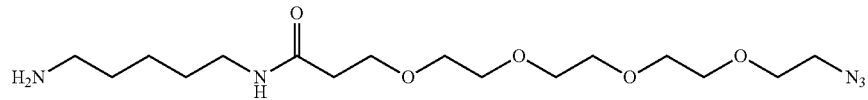
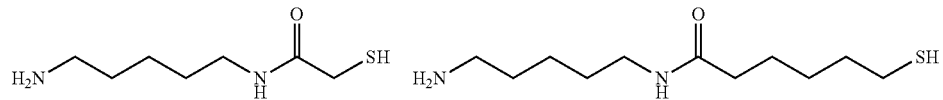
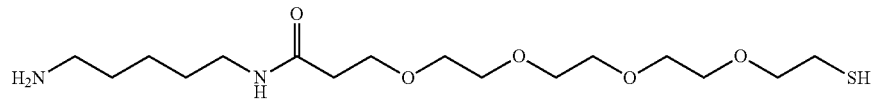
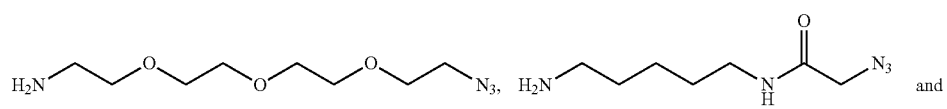 and
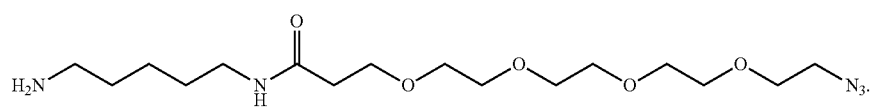

In particular embodiments, the primary amine compound is
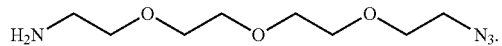
In certain embodiments, the primary amine compound is selected from the group consisting of
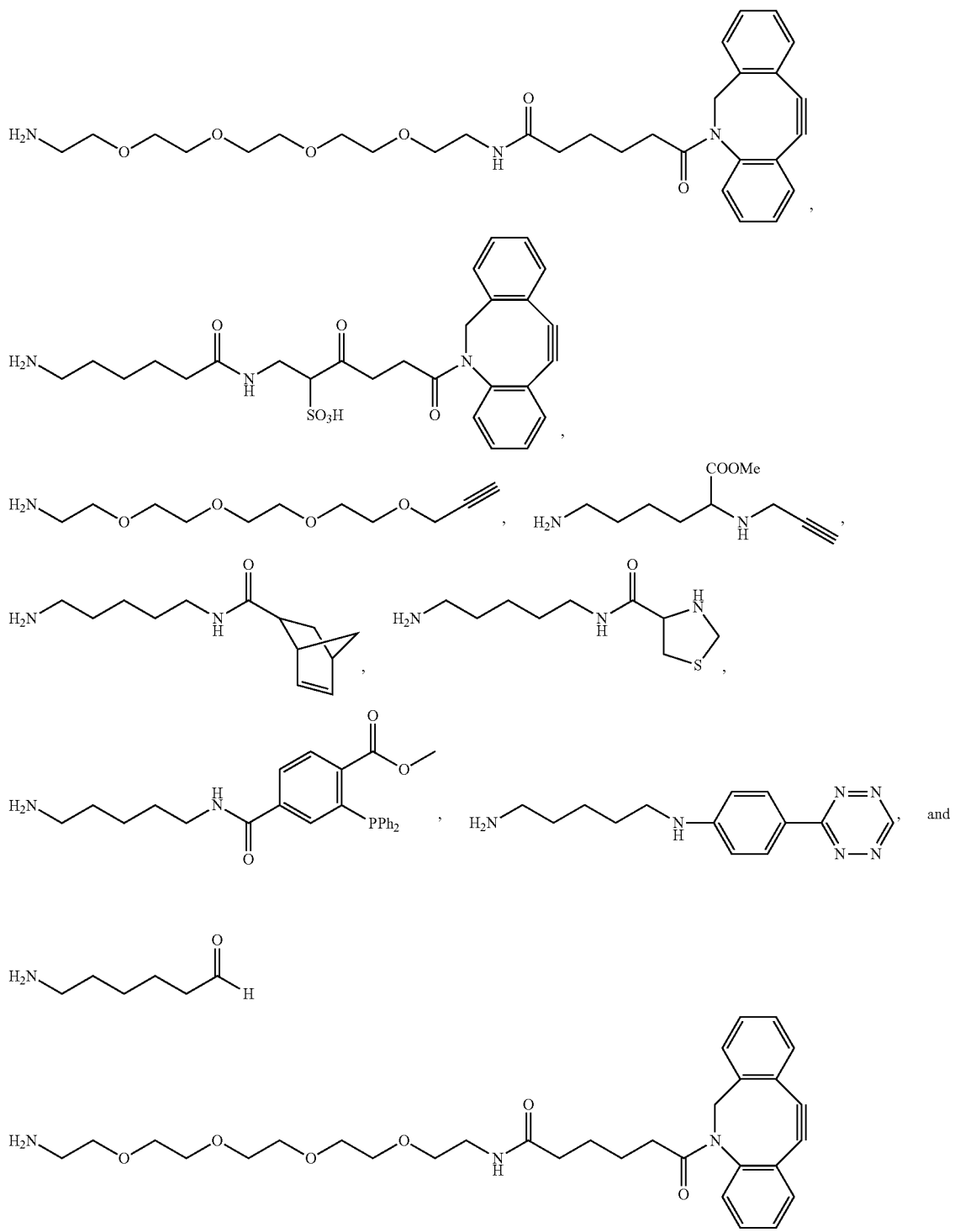

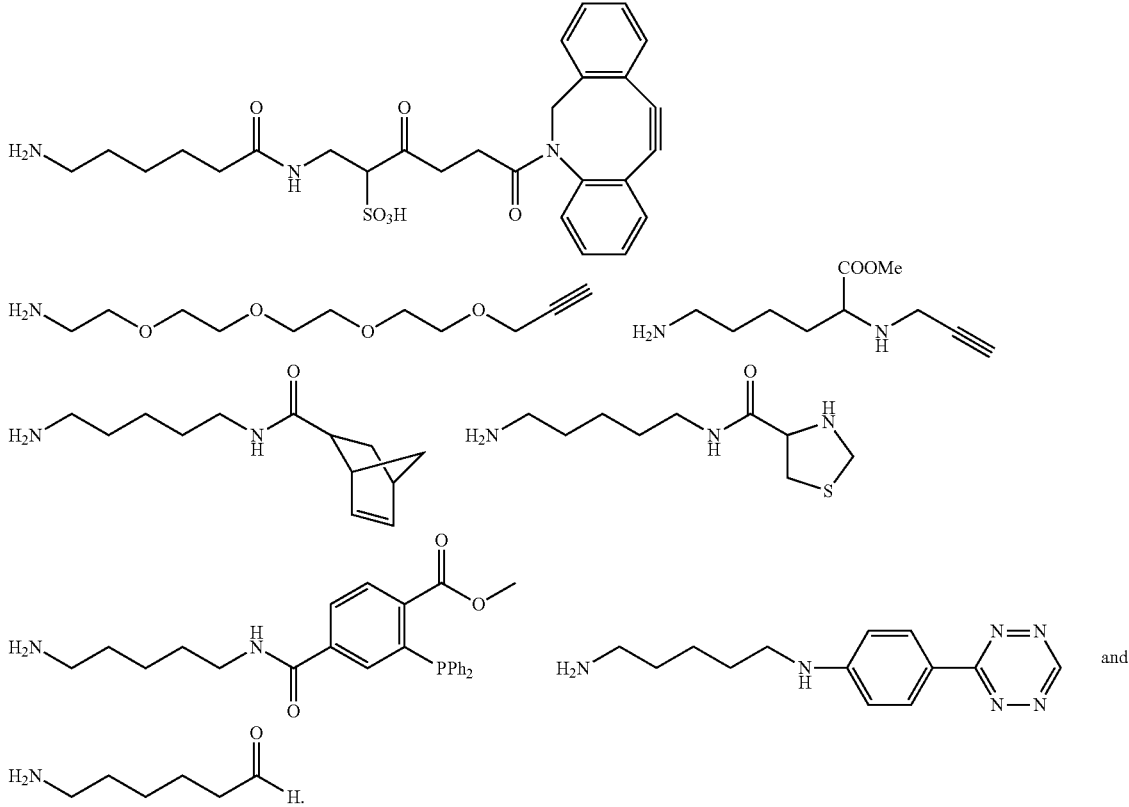

Reactive Linker-Payload Compounds

As discussed, included in the present disclosure are methods comprising the step of reacting a glutaminyl-modified antibody with a reactive linker payload compound. The reactive linker payload compounds comprise a divalent linker flanked by a reactive group, which is capable of reacting with the reactive group of the primary amine compounds described herein, and a payload.

In some embodiments, the reactive linker-payload compound is a compound according to formula XX-L-Pay, wherein XX is a reactive group capable of reacting with the reactive group of the primary amine compound, L is a divalent linker, and Pay is a payload.

In certain embodiments, the reactive group of the primary amine compound is —$N_3$, and XX is a monovalent moiety capable of undergoing a 3+2 cycloaddition reaction with the —$N_3$ group of said primary amine. In some embodiments, XX is an alkyne or cycloalkyne moiety capable of undergoing an azide-alkyne cycloaddition reaction. In some embodiments, XX is capable of undergoing a 3+2 cycloaddition reaction in the absence of copper. In some embodiments, the cycloalkyne moiety is a cyclooctyne, substituted cyclooctyne, or derivative thereof.

In some embodiments, the reactive group of the primary amine compound is —$N_3$, and XX is a cycloalkyne, substituted cycloalkyne, fluorinated cyclooctyne, e.g., DIFO, DIFO2, and DIFO3; a cyclooctyne fused to aryl groups, e.g., dibenzocyclooctyne, DIBO; azadibenzocyclooctyne, e.g., DIBAC,; azadimethoxycyclooctyne, e.g., DIMAC, or derivative thereof.

In some embodiments, the reactive group of the primary amine compound is —$N_3$, and XX is:

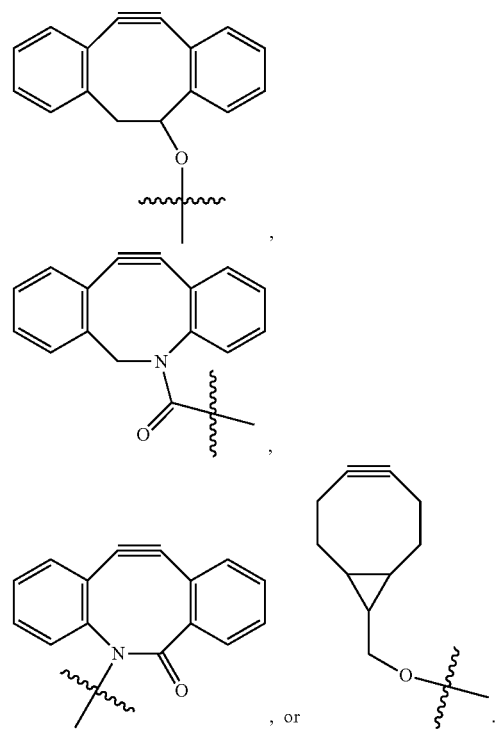

In certain embodiments, the glutaminyl-modified antibody is linked to the payload via a divalent linker. The divalent linker can be any divalent linker deemed suitable by the practitioner of skill. Useful divalent linkers include alkylene and heteroalkylene groups. In certain embodiments, the linker is —(CH$_2$)$_n$—, where n is an integer from 1 to 12. In certain embodiments, the linker is —(O—CH$_2$—CH$_2$)$_m$—, where m is an integer from 1 to 12. In certain embodiments, the linker is —(CH$_2$)$_n$—(O—CH$_2$—CH$_2$)$_m$—, where n is an integer from 1 to 12 and m is independently an integer from 1 to 12. In certain embodiments, the linker is —(CH$_2$)$_n$—(O—CH$_2$—CH$_2$)$_m$—(CH$_2$)$_n$—, where n is an integer from 1 to 12 and m is independently an integer from 1 to 12.

In some embodiments, the reactive group of the primary amine compound is —N$_3$, and the reactive linker-payload compound comprises:

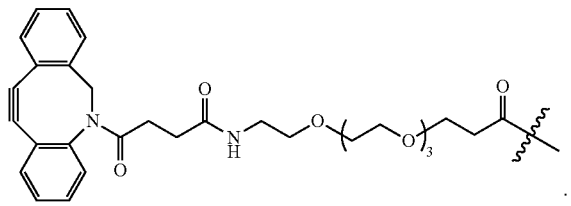

Useful divalent linkers can comprise or further comprise any linker used for antibody-drug conjugates. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015. In certain embodiments, the linker can comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), 4-(N-maleimidomethyl)cyclohexanecarboxylic acid (MCC), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present description are disclosed, e.g., in U.S. Pat. No. 7,754,681 and in Ducry, *Bioconjugate Chem.*, 2010, 27:5-13, and the references cited therein.

In some embodiments, the linker comprises -val-cit-PAB-.

In some embodiments, the reactive linker-payload compound is according to the following formula:

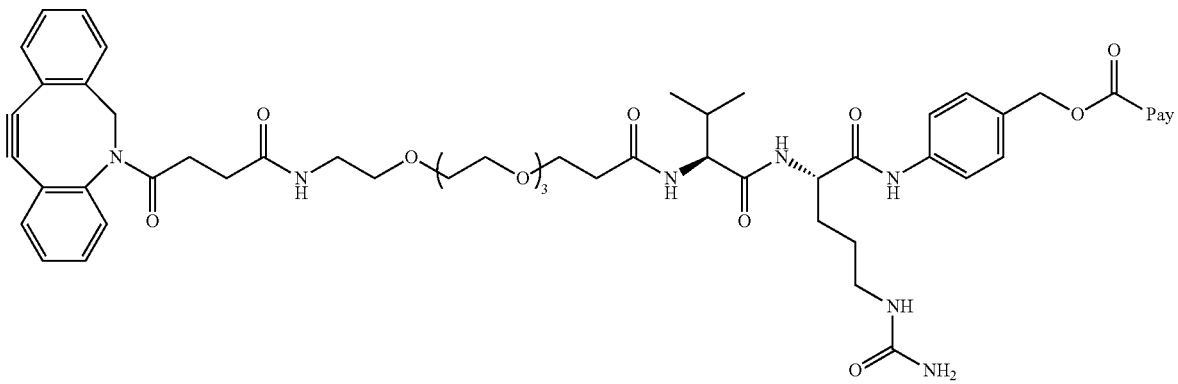

wherein Pay is a payload.

The payload of the reactive linker-payload compounds described herein can be any payload deemed suitable to those of skill in the art. In particular embodiments, the payload is provided in the form of a reactive payload compound comprising a reactive group capable of forming a covalent bond with a reactive group on the primary amine compound. Useful reactive groups for the reactive payload compounds include azides, alkynes, cycloalkynes, thiols, alcohols, ketones, aldehydes, acids, esters, hydrozides, analines, and amines. Reactive payload compounds can be prepared or obtained from sources known to those of skill in the art.

In certain embodiments, the payload comprises a cytotoxic agent. Cytotoxic agents include any agent that is detrimental to the growth, viability or propagation of cells. Examples of suitable cytotoxic agents and chemotherapeutic agents include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing.

According to certain embodiments, the cytotoxic agent is a maytansinoid such as DM1 or DM4, a tomaymycin derivative, or a dolastatin derivative. According to certain embodiments, the cytotoxic agent is an auristatin such as MMAE, MMAF, or derivatives thereof. Other cytotoxic agents known in the art are contemplated within the scope of the present disclosure, including, e.g., protein toxins such ricin, *C. difficile* toxin, *pseudomonas* exotoxin, ricin, diphtheria toxin, *botulinum* toxin, bryodin, saporin, pokeweed toxins (i.e., phytolaccatoxin and phytolaccigenin), and others such as those set forth in Sapra et al., Pharmacol. & Therapeutics, 2013, 138:452-469. In certain embodiments, the payload is MMAE.

The payload can also comprise a radionuclide. Exemplary radionuclides that can be used include, but are not limited to, e.g., $^{225}$Ac, $^{212}$Bi, $^{213}$Bi, $^{131}$I, $^{186}$Re, $^{227}$Th, $^{222}$Rn $^{223}$Ra, $^{224}$Ra, and $^{90}$Y.

Pharmaceutical Compositions and Methods of Administration

Provided herein are pharmaceutical compositions comprising the glutaminyl-modified antibodies and/or antibody-payload conjugates. The pharmaceutical compositions of the description are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of antibody or conjugate administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present description normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the description, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present description can be delivered subcutaneously or intravenously with a standard needle and syringe. In addition, with respect to subcutaneous delivery, a pen delivery device readily has applications in delivering a pharmaceutical composition of the present description. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present description. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present description include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, *CRC Crit. Ref. Biomed. Eng.* 14:201). In another embodiment, polymeric materials can be used; see, *Medical Applications of Controlled Release*, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Also provided are methods comprising administering to a subject in need thereof a therapeutic composition comprising an antibody or antibody conjugate disclosed herein. The therapeutic composition can comprise any of the antibodies, antibody fragments, or conjugates, and a pharmaceutically acceptable carrier or diluent.

The antibodies and conjugates of the description are useful, inter alia, for the treatment, prevention and/or amelioration of any disease or disorder associated with or mediated by their cognate antigen expression or activity, or treatable by blocking the interaction between their cognate antigen and receptor or ligand or otherwise inhibiting antigen activity and/or signalling, and/or promoting receptor internalization and/or decreasing cell surface receptor number. For example, antibodies and conjugates of the present description can be useful for the treatment of tumors that express their cognate antigens and/or that respond to antigen-mediated signalling. The antibodies and conjugates fragments provided herein may also be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and conjugates of the description are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma.

In the context of the methods of treatment described herein, the antibodies and conjugates may be administered as a monotherapy (i.e., as the only therapeutic agent) or in combination with one or more additional therapeutic agents (examples of which are described elsewhere herein).

Diagnostic Uses of the Antibodies

The antibodies and conjugates described herein may also be used to detect and/or measure a target antigen, or target antigen-expressing cells in a sample, e.g., for diagnostic purposes. For example, an antibody, or conjugate thereof, may be used to diagnose a condition or disease characterized by aberrant expression (e.g., over-expression, under-expression, lack of expression, etc.) of the target antigen. Exemplary diagnostic assays for the target antigen may comprise, e.g., contacting a sample, obtained from a patient, with an antibody or conjugate, wherein the antibody is labelled with a detectable label or reporter molecule.

Alternatively, an unlabelled antibody or conjugate can be used in diagnostic applications in combination with a secondary antibody which is itself detectably labelled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure target antigen in a sample include enzyme-linked immunosorbent assay (ELISA), radioimmunoassay (RIA), immuno-PET (e.g., $^{89}Zr$, $^{64}Cu$, etc.), and fluorescence-activated cell sorting (FACS).

Samples that can be used in diagnostic assays according to the present description include any tissue or fluid sample obtainable from a patient which contains detectable quantities of target antigen, or fragments thereof, under normal or pathological conditions. Generally, levels of target antigen in a particular sample obtained from a healthy patient (e.g., a patient not afflicted with a disease or condition associated with abnormal target antigen levels or activity) will be measured to initially establish a baseline, or standard, level of target antigen. This baseline level of target antigen can then be compared against the levels of target antigen measured in samples obtained from individuals suspected of having a target antigen related disease or condition.

EXAMPLES

As used herein, the symbols and conventions used in these processes, schemes and Examples, regardless of whether a particular abbreviation is specifically defined, are consistent with those used in the contemporary scientific literature, for example, the Journal of the American Chemical Society or the Journal of Biological Chemistry.

Specifically, but without limitation, the following abbreviations may be used in the Examples and throughout the specification:

| Abbreviation | Term |
| --- | --- |
| ADC | Antibody-drug conjugate |
| Aglycosylated antibody | Antibody does not have any glycan |
| API | Atmospheric pressure ionization |
| aq | Aqueous |
| Boc | N-tert-butoxycarbonyl |

-continued

| Abbreviation | Term |
| --- | --- |
| BupH | Thermo Scientific Prod# 28372, containing 100 mM sodium phosphate and 150 mM sodium chloride, potassium free, pH was adjusted from 7.2 to 7.6-7.8 Milli-Q water, unless otherwise noted. |
| CD | Cyclodextrin |
| CHO | Chinese hamster ovary |
| COT | Cyclooctynol |
| Da | Dalton |
| DAD | Diode array detector |
| DAR | Drug to antibody ratio |
| DAR (MALDI) | DAR as determined based on intact mass analysis by MALDI-TOF |
| DCM | Dichloromethane |
| Deglycosylated antibody | Antibody N297-linked glycan was removed |
| DIBAC | Dibenz[b,f]azocine, 11,12-didehydro-5,6-dihydro- |
| DIBAC-Suc | Dibenz[b,f]azocine-5(6H)-butanoic acid, 11,12-didehydro |
| DIBACT | 3H-Benzo[c]-1,2,3-triazolo[4,5-e][1]benzazocine, 8,9-dihydro- |
| DIPEA | Diisopropylethylamine |
| DMF | N,N-dimethylformamide |
| DMSO | Dimethylsulfoxide |
| EC | Enzyme commission |
| ELSD | Evaporating light scattering detector |
| ESI | Electrospray ionization |
| g | Gram |
| HATU | N-[(Dimethylamino)-1H-1,2,3-triazolo-[4,5-b]pyridin-1-ylmethylene]-N-methylmethanaminium hexafluorophosphate N-oxide |
| HC | Heavy chain of immunoglobulin |
| HEK | Human embryonic kidney cells |
| HPLC | High performance liquid chromatography |
| h, hr, or hrs | Hours |
| LC | Light chain of immunoglobulin |
| LCh | Liquid chromatography |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| μL | microliters |
| mM | millimolar |
| μM | micromolar |
| MMAE | Monomethyl auristatin E |
| MS | Mass spectrometry |
| MsCl | Methanesulfonyl chloride |
| MSD | Mass-selective detector |
| MTG | Microbial transglutaminase (MTG EC 2.3.2.13, Zedira, Darmstadt, Germany) |
| MW | Molecular weight |
| NHS | N-hydroxy succinimide |
| nM | nanomolar |
| NMR | Nuclear magnetic resonance |
| PAB | Para-aminobenzyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| PNGase F | N-glycosidase F (10000 Units/mg of antibody) from *Flavobacterium meningosepticum* (PNGase F, New England Biolabs, MA) |
| ppm | Parts per million (chemical shift; δ) |
| RP | Reversed phase |
| RT or rt | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VC | Valine-citrulline |

For all of the following Examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1: Antibody Deglycosylation

Deglycosylation of a purified CHO-derived human IgG1 antibody, such as anti-HER2, and anti-PRLR at a concentration of 0.5-2 mg/mL in BupH (100 mM sodium phosphate buffer and 150 mM NaCl, initial pH 7.6-7.8) was conducted by incubation with N-glycosidase F (10000 Units/mg of antibody) from *Flavobacterium meningosepticum* (PNGase F, New England Biolabs, MA) at 37° C. overnight without rotation. Upon completion of the deglycosylation, the PNGase F was removed by centrifugal ultrafiltration (Amicon Ultra-4, MWCO 50K, Millipore, Ireland) using BupH (initial pH 7.6-7.8).

Completion of the deglycosylation was demonstrated by molecular weight reduction of the intact antibody observed on SDS-PAGE performed under non-reducing and reducing conditions.

Example 2: Optimization of Conjugation Conditions

To minimize the formation of undesired side product and achieve a maximum DAR of the ADC conjugates, several variables were examined in the enzymatic conjugation process, including reaction temperature, time, initial buffer pH, molar equivalents of the amine reagent to the antibody, unit of MTG per mg antibody, and different primary amine reagents. The mixture from each step was directly analyzed using SDS-PAGE, MALDI-MS and/or ESI-MS, and SEC. Detailed analysis is provided in Example 8.

Optimizing Transglutaminase Units to Antibody

Three units of microbial transglutaminase (MTG, EC 2.3.2.13; protein-glutamine-γ-glutamyltransferase) per deglycosylated anti-PRLR antibody (0.5 U/mg/mL, 1 U/mg/mL, and 5 U/mg/mL) in BupH (initial pH 7.6-7.8) were examined in the presence of 35 molar equivalents azido-dPEG$_3$-amine (MW 218.26; H$_2$N—(CH$_2$—CH$_2$O)$_3$—CH$_2$—CH$_2$—N$_3$) to the antibody, and the conjugations were executed overnight at 37° C. The gel results indicated that although a lower concentration of MTG (0.5 U/mg) reduced the appearance of the side product, the DAR (MALDI) value of the conjugates at Q295 of the delycosylated antibody were also reduced from a maximum of 2 (with 5 U/mg MTG) to 0.3.

Optimizing Molar Ratio of Azido-dPEG$_3$-Amine to Antibody

Figure 2A:
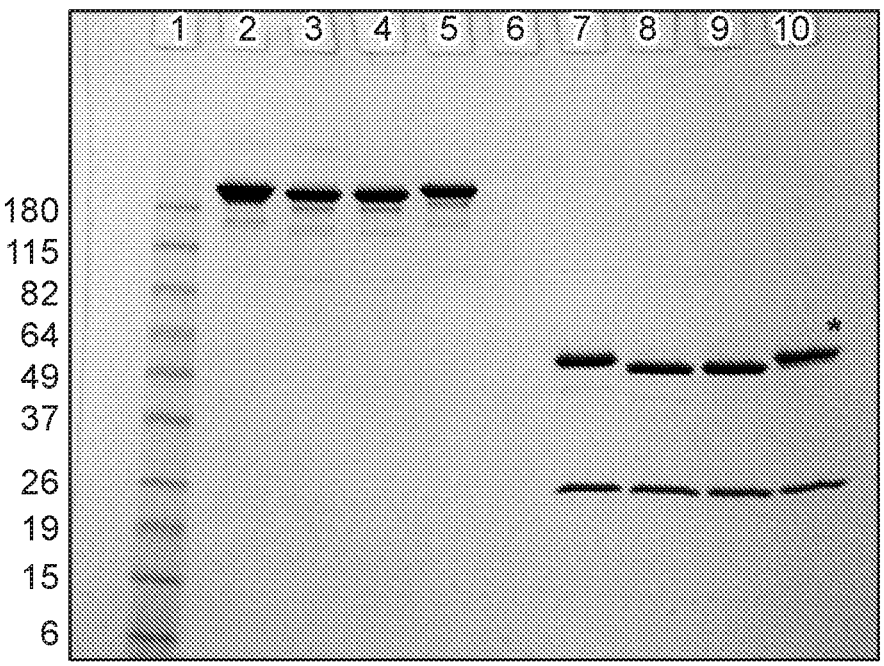
FIGS. 2A and 2B show SDS-PAGE gels demonstrating molecular weight changes from naked antibody to deglycosylated antibody, and/or to azido-functionalized deglycosylated antibody and/or antibody linker drug conjugate performed under non-reducing and reducing conditions. For example.
Figure 2B:
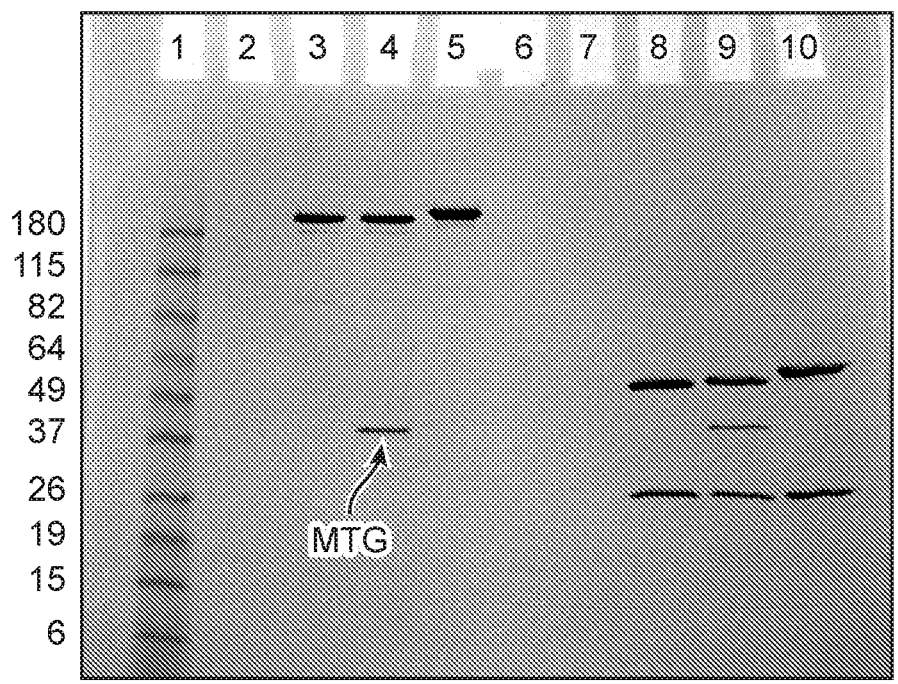
Figure 2C:
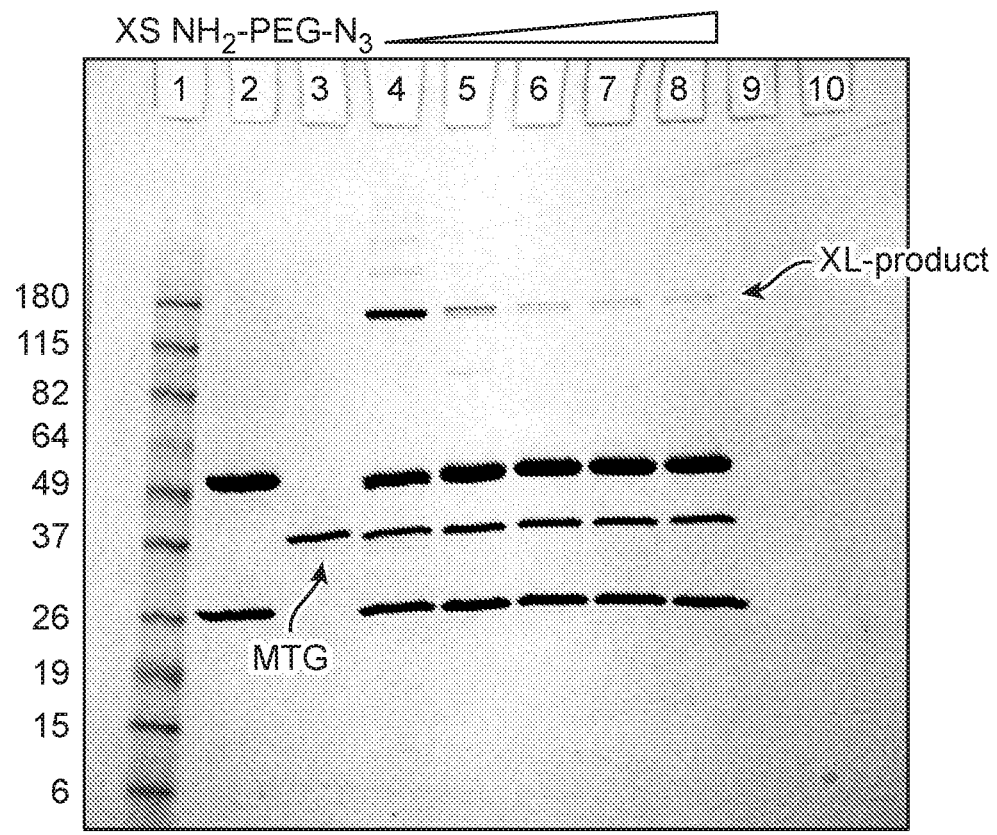
FIG. 2C shows an SDS-PAGE gel demonstrating minimization of cross-link antibody site product with increasing equivalents of primary amine compound.

Different molar equivalents of azido-dPEG$_3$-amine (0, 20, 100, 200, 500 equiv.) were examined with an objective to achieve a DAR of 4. An aglycosylated antibody (0.5 mg/mL in BupH (initial pH 7.6-7.8)) was mixed with azido-dPEG$_3$-'amine and MTG (5 U MTG/mg), followed by incubation overnight at 37° C. It was found that over 20-fold molar excess of azido-dPEG$_3$-amine could achieve a DAR of 4 under these conditions. However, a prominent side product was also observed using these conditions. The conjugated products (without further purification) were analyzed on a reducing SDS-PAGE gel to estimate the ratio of the side product to the conjugated products. The gel results indicated that the side product decreased as the molar ratio of azido-dPEG$_3$-amine to the antibody increased (FIG. 2C).

Optimizing Buffer pH (Initial pH 7.2-8.2) at 24° C. and 37° C.

A time-course study for a deglycosylated antibody conjugation with azido-dPEG$_3$-amine (35 equiv.) in combination with different BupH pHs (initial pH 7.2 to 8.2) and temperatures (25° C. and 37° C.) was conducted to identify optimized conditions to suppress the side product. It was found that higher pH (pH 8.2) or lower temperature (24° C.) suppressed the formation of the side product. However, the conjugation efficiency at Q295 of the antibody was also significantly reduced, resulting in a DAR (MALDI)≤1.1. An overnight reaction time (over 16 hours) at an initial pH 7.6-7.8 and 37° C. was necessary to reach a completion of the antibody conjugation with azido-dPEG$_3$-amine having a maximum DAR (MALDI) of 2.

The conjugation results with optimized conditions were summarized in FIG. 16. The results indicated that improved site-specific conjugation conditions included high molar excess of the primary amine azide (>200 equiv.), MTG concentration of 5 U/mg of antibody, initial pH 7.6-7.8, reaction temperature of 37° C., and reaction times. The conditions were also suitable for the antibody conjugations with different primary amine reagents.

Example 2A: Optimization of Reaction pH Conditions

Optimizing Reaction pH at 37° C.

This example provides evaluations and results for reaction pH in transglutaminase catalyzed addition of amines to antibodies.

In a time course study for an aglycosylated antibody conjugation with azido-dPEG$_3$-amine (at least 25 equiv.), different final reaction pHs were screened at 37° C. using the following procedure. BupH phosphate buffered saline (Thermo Scientific, potassium-free) in Milli-Q water (500 mL) was measured for an initial pH value of pH 6.98. The pH of the initial pH 6.98 BupH phosphate buffered saline solution was adjusted using aqueous HCl or NaOH to obtain an additional three solutions with pHs of 6.46, 7.75, and 7.94, respectively—for a total of four different pH solutions (pH 6.46, 6.98, 7.75, and 7.94, respectively). Each of the adjusted pH solutions were independently added to four separate 1.2 mL vials. Then, the following reagents were added in the following order:
  (i) aglycosylated antibody (1 mg, 6.8 nmol);
  (ii) azido-dPEG$_3$-amine (0.3 mg, 1374.5 nmol, 202 equiv.); and
  (iii) mTGase (0.125 mg, 5 U)
where the reaction pHs were 6.42, 6.98, 7.62, and 7.76, respectively. Each vial was then allowed to incubate at 37° C. while mixing, shaking, or stirring. Each reaction was monitored and assessed by ESI-MS at 1, 2, 4, and 8 h after the addition of Milli-Q water (100 µL) at each of the aforementioned time points.

In another time course study for an anti-HER2 (hIgG1, N180Q) mAb conjugation with azido-dPEG$_3$-amine (at least 25 equiv.), different final reaction pHs were screened at 37° C. using the following procedure. BupH phosphate buffered saline (Thermo Scientific, potassium-free) in Milli-Q water (500 mL) was measured for an initial pH value of pH 6.98. The pH of the initial pH 6.98 BupH phosphate buffered saline solution was adjusted using aqueous HCl or NaOH to obtain an additional six solutions with pHs of 5.71, 5.87, 6.31, 7.74, 8.61, and 9.22, respectively—for a total of seven different pH solutions (pH 5.71, 5.87, 6.31, 6.98, 7.74, 8.61, and 9.22, respectively). Each of the adjusted pH solutions was independently added to seven separate 1.2 mL vials. Then, the following reagents were added in the following order:
(i) anti-HER mAb (1 mg, 6.8 nmol);
(ii) azido-dPEG$_3$-amine (0.3 mg, 1374.5 nmol, 202 equiv.); and
(iii) mTGase (0.125 mg, 5 U)
where the reaction pHs were 5.87, 6.07, 6.35, 6.92, 7.51, 7.88, and 8.56, respectively. Each vial was then allowed to incubate at 37° C. while mixing, shaking, or stirring. Each reaction was assessed by ESI-MS at 8 h after the addition of Milli-Q water (100 µL).

Additional molar equivalents of azido-dPEG$_3$-amine (0, 25, 50, 100, and 200 equiv.) were screened under different final reaction pHs at 37° C. using the following procedure. BupH phosphate buffered saline (Thermo Scientific, potassium-free) in Milli-Q water (500 mL) was measured for an initial pH value of pH 6.98. The pH of the initial pH 6.98 BupH phosphate buffered saline solution was adjusted using aqueous HCl or NaOH analogous to the procedures described above. Each of the adjusted pH solutions were independently added to five separate 1.2 mL vials. Then, the following reagents were added in the following order:
(i) anti-HER mAb (1 mg, 6.8 nmol);
(ii) azido-dPEG$_3$-amine (0.3 mg, 1374.5 nmol, 202 equiv.); and
(iii) mTGase (0.125 mg, 5 U)
where the reaction pHs were 7.51, 7.46, 7.46, 7.45, and 7.44, respectively. Each vial was then allowed to incubate at 37° C. while mixing, shaking, or stirring. After incubating for 4 h, 3 µL of each reaction mixture was diluted with Milli-Q water containing 0.1% formic acid (100 µL), and the equivalent of about 2 µg of antibody (or <50 µL) of each sample was assessed by ESI-MS.

The conjugation results with optimized conditions were summarized in Table 1. The results indicated that improved site-specific conjugation conditions included high molar excess of the primary amine azide (>200 equiv.) and a reaction pH 7-8. The conditions were also suitable for the antibody conjugations with different primary amine reagents.

TABLE 1

| Amine-Substrate | Equiv. to Ab | TG conc. (U/mg of Ab) | pH | Temp. (° C.) | Rxn. Time (Hrs) | DAR |
|---|---|---|---|---|---|---|
| Azido-dPEG$_3$-amine | 202 | 5 | 5.87 | 37 | 8 | 3.3 |
| Azido-dPEG$_3$-amine | 202 | 5 | 6.07 | 37 | 8 | 3.5 |
| Azido-dPEG$_3$-amine | 202 | 5 | 6.35 | 37 | 8 | 3.7 |
| Azido-dPEG$_3$-amine | 202 | 5 | 6.92 | 37 | 8 | 3.9 |
| Azido-dPEG$_3$-amine | 202 | 5 | 7.51 | 37 | 8 | 4 |
| Azido-dPEG$_3$-amine | 202 | 5 | 7.88 | 37 | 8 | 4 |
| Azido-dPEG$_3$-amine | 202 | 5 | 8.56 | 37 | 8 | 3.2 |
| Azido-dPEG$_3$-amine | 0 | 5 | 7.51 | 37 | 4 | 0 |
| Azido-dPEG$_3$-amine | 25 | 5 | 7.46 | 37 | 4 | 3.4 |
| Azido-dPEG$_3$-amine | 50 | 5 | 7.46 | 37 | 4 | 3.5 |
| Azido-dPEG$_3$-amine | 100 | 5 | 7.45 | 37 | 4 | 3.9 |
| Azido-dPEG$_3$-amine | 200 | 5 | 7.44 | 37 | 4 | 3.9 |

Table 1 indicates that reaction pH at 7.51 or 7.88 provided an optimal DAR of 4. In addition, a molar excess of at least 200 equiv. of the azido-dPEG$_3$-amine, with respect to the amount of antibody, provided an optimal DAR of at least 3.9.

Figure 11:
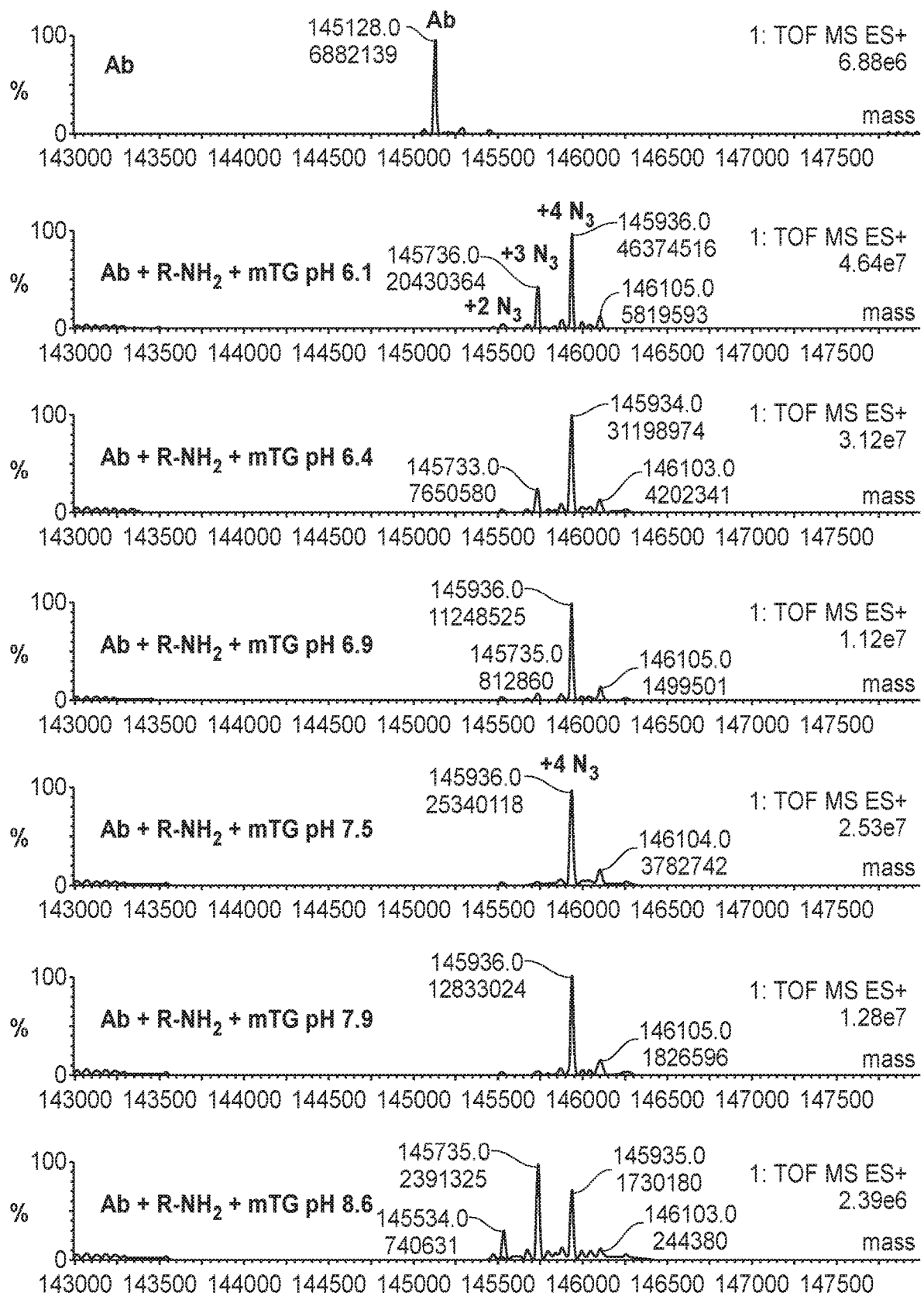
FIG. 11 shows ESI-MS data for mTGase-mediated azido-functionalization of a deglycosylated antibody at different reaction pHs after 8 h.

As shown in FIG. 11, the first ESI-MS spectrum shows the corresponding mass for an unreacted antibody, for example, when no azido-dPEG$_3$-amine nor transglutaminase is present. The following ESI-MS spectra correspond to reaction pHs of 5.87, 6.07, 6.35, 6.92, 7.51, 7.88, and 8.56, respectively, taken at the 8 h time point. Reaction pHs of 6.92, 7.51, and 7.88 show optimal conjugation of the azido-dPEG$_3$-amine to the antibody using the transglutaminase. Alternatively stated, the ESI-MS spectra for reaction pHs of 6.92, 7.51, and 7.88 show a DAR of about 4 with minimal side reaction products.

Figure 12:
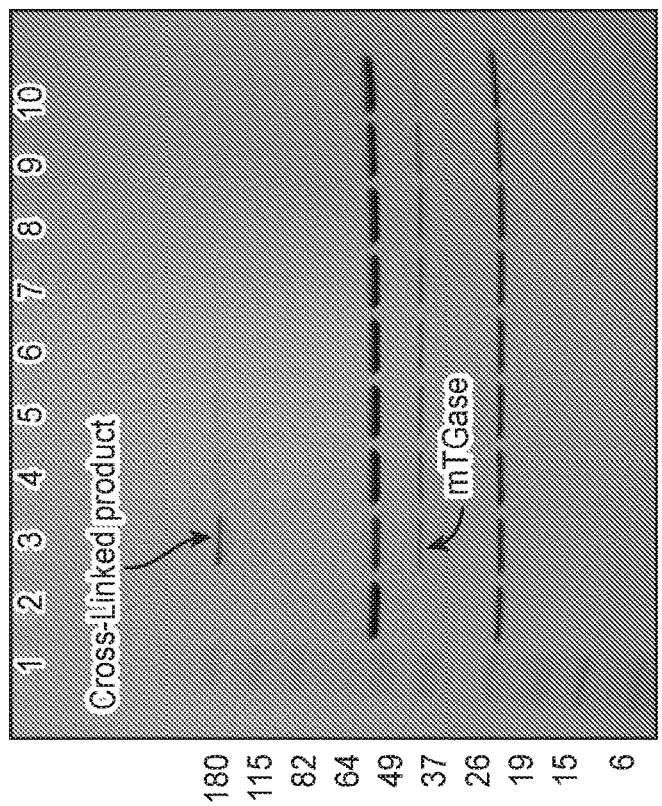
FIG. 12 shows a Coomassie-stained SDS-PAGE gel demonstrating the effect of pH on molecular weight changes for mTGase-mediated azido-functionalization of a mAb (H1H21234N; hIgG1 N180Q).

As shown in FIG. 12, SDS-PAGE gel experiments performed under reducing conditions indicated reductions in the amount of cross-linked side products from the transglutaminase-mediated antibody conjugations at optimal reaction pHs (e.g. 7.51, 7.88).

Figure 13:
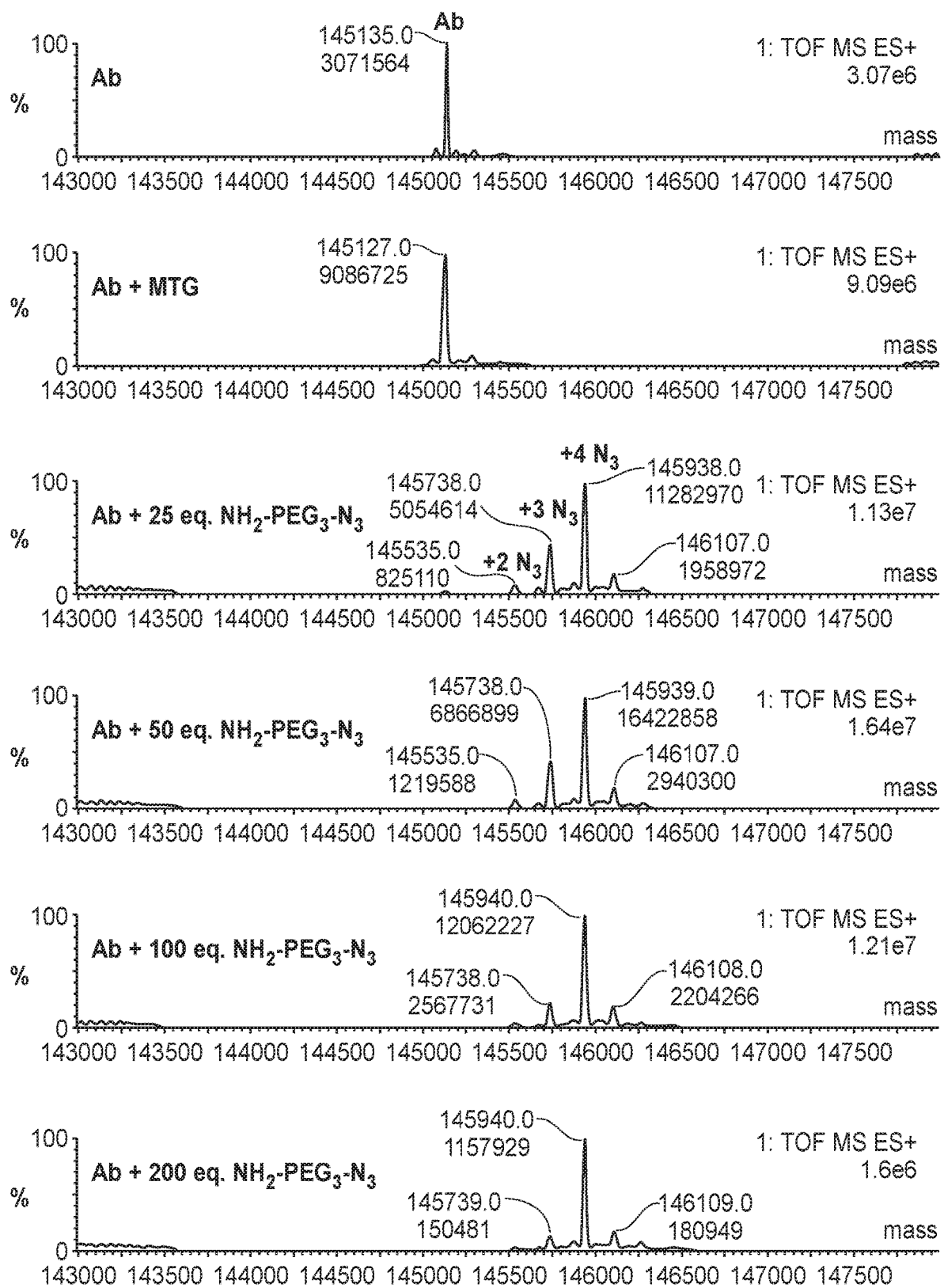
FIG. 13 shows the effects of different equivalents of azido-dPEG$_3$-amine at different reaction pHs as monitored by ESI-MS.

As shown in FIG. 13, at least 200 molar equivalents of azido-dPEG$_3$-amine provided an optimal DAR of 3.9 for the transglutaminase-meditated antibody conjugations. More specifically, the first ESI-MS spectrum shows a mass for the antibody in the absence of transglutaminase and azido-dPEG$_3$-amine. The second ESI-MS spectrum shows a mass for the antibody in the presence of transglutaminase, but without azido-dPEG$_3$-amine. The following four ESI-MS spectra show the effects of increasing molar equivalents of azido-dPEG$_3$-amine at an optimal pH for the reaction of about 7.4 (see also, Table 1, above). Reactions with less than 200 molar equivalents of azido-dPEG$_3$-amine provided increased amounts of side reaction products.

Figure 14:
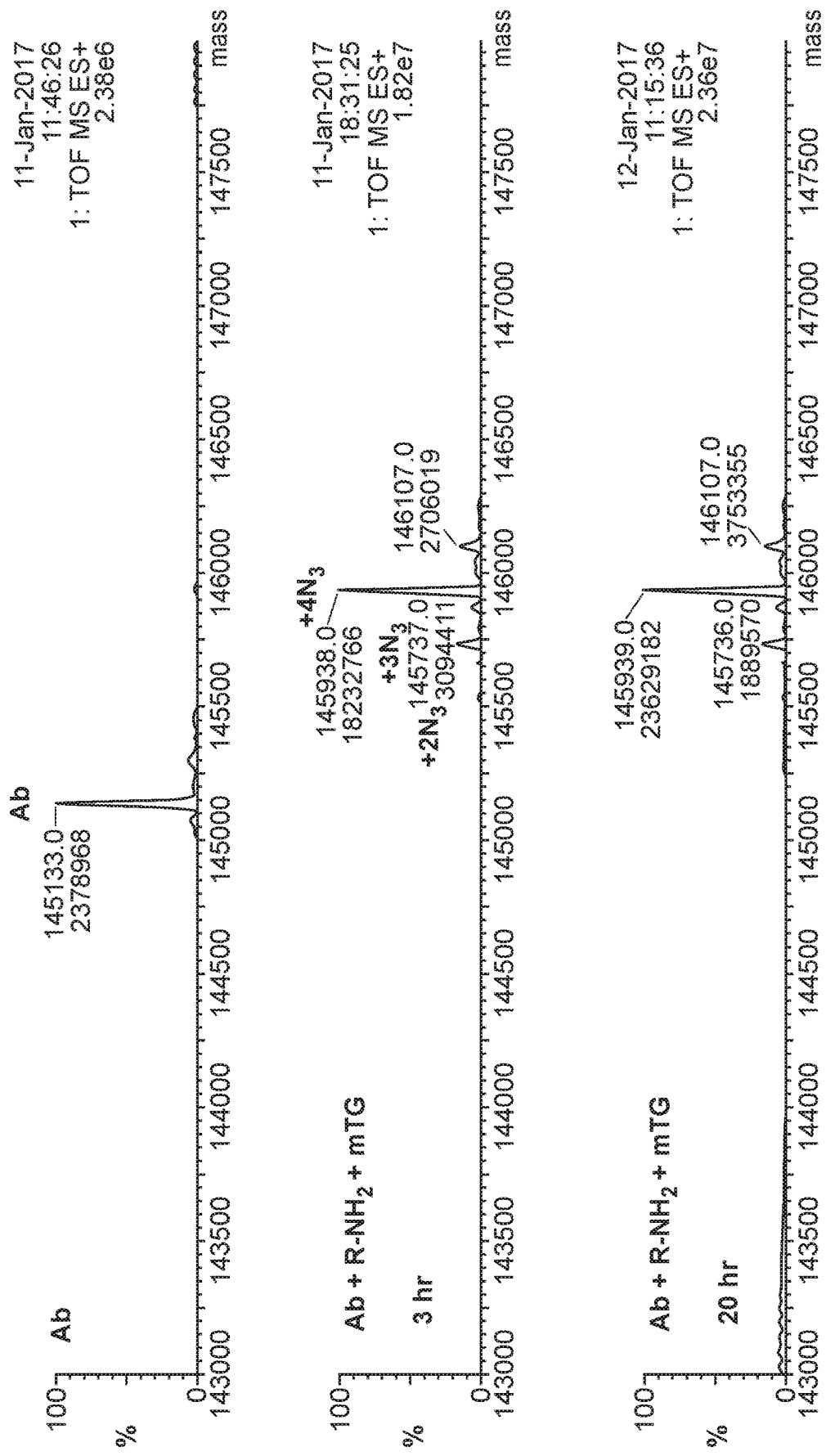
FIG. 14 shows the effects of the order of addition for azido-dPEG$_3$-amine and mTGase, and for mTGase and azido-dPEG$_3$-amine as monitored by ESI-MS..
Figure 14:
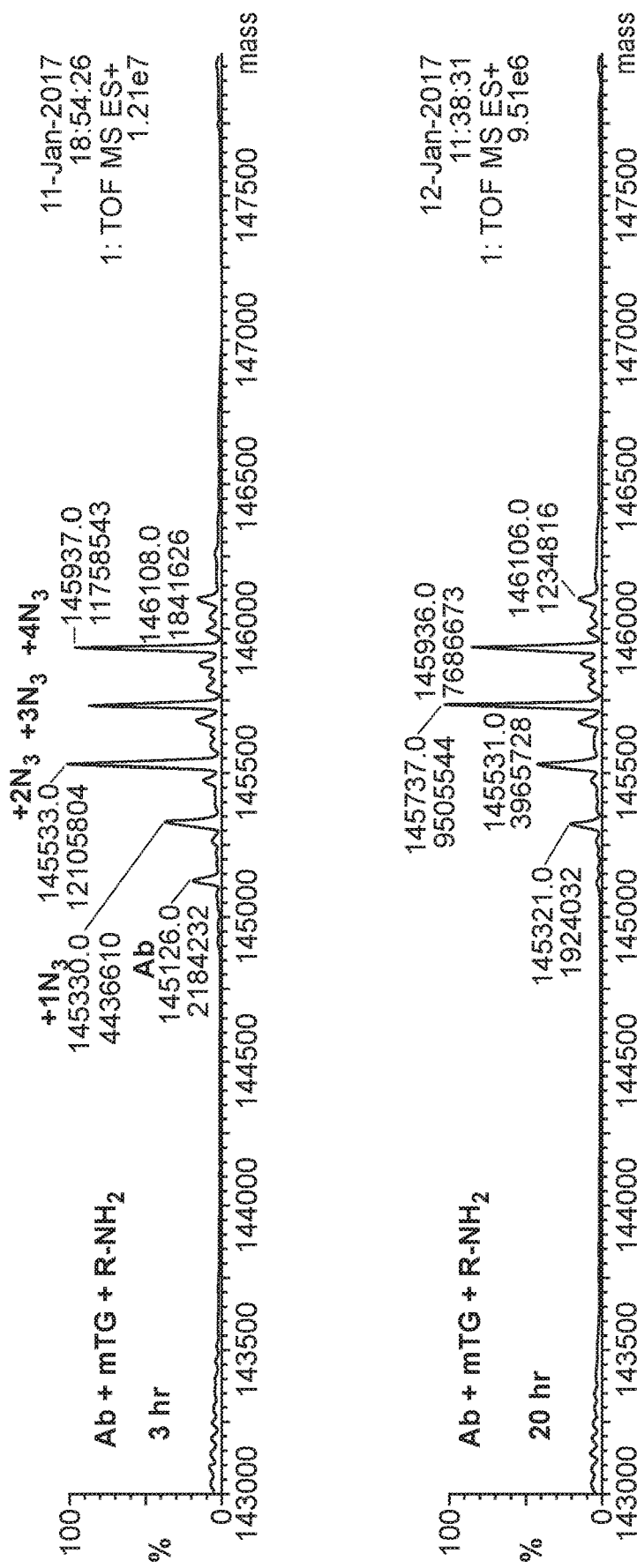
Figure 15:
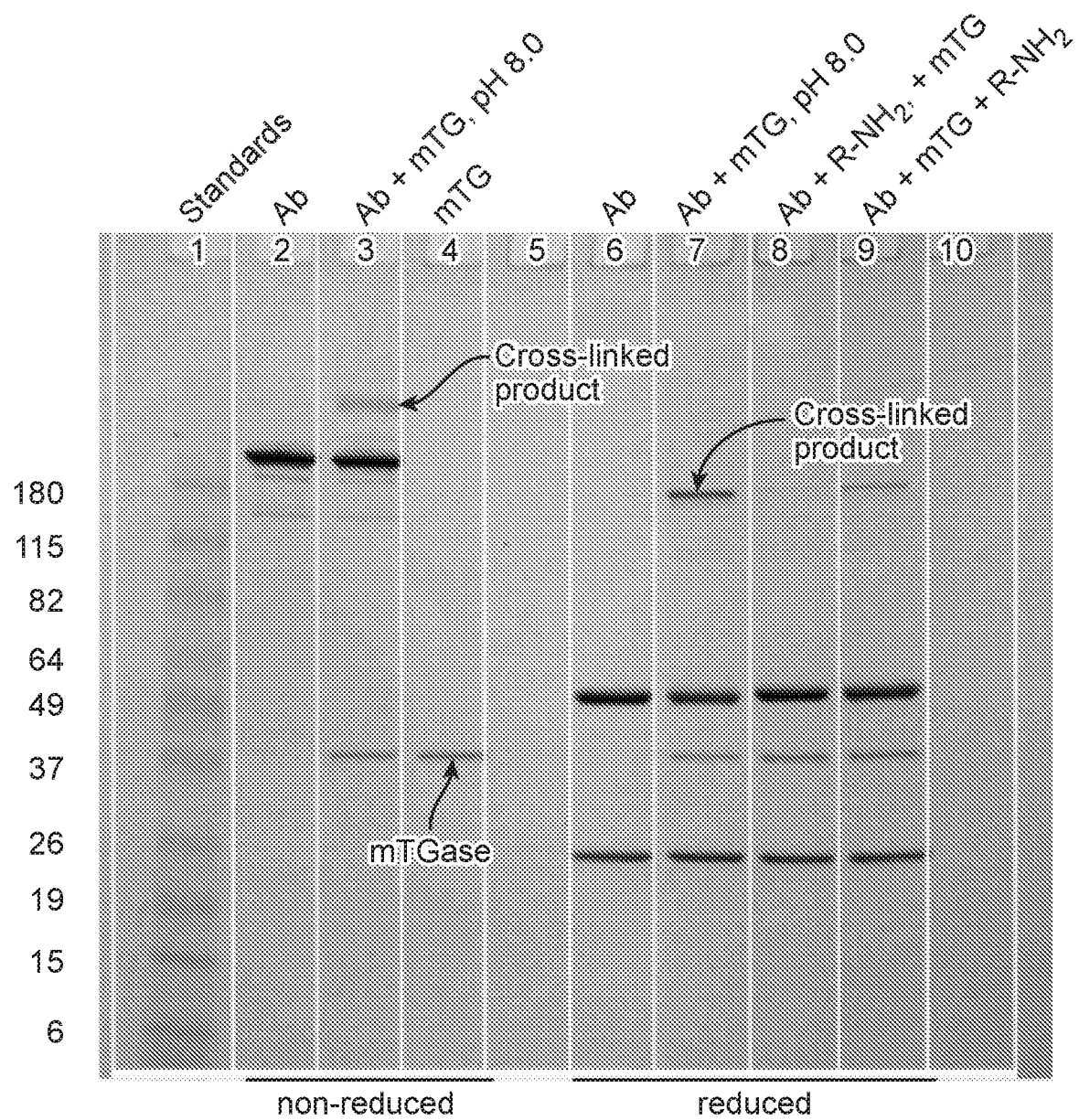
FIG. 15 shows an SDS-PAGE gel indicating a dependence on the order of addition for the azido-dPEG$_3$-amine and mTGase for the amounts of cross-linked products or side reaction products produced.

As shown in FIG. 14, the ESI-MS spectra show the corresponding mass for (1) an unreacted antibody; (2) the reaction in the addition order of antibody fist, followed with azido-dPEG$_3$-amine, and finally with transglutaminase, at the 3 h and 20 h time points; (3) the reaction in the addition order of antibody fist, followed with transglutaminase, and finally with azido-dPEG$_3$-amine, at the 3 h and 20 h time points. The results indicated that the reaction (2) was near completion (with a high DAR), and the reaction (3) was not completed after 20 h, and also showed side reaction products by SDS-PAGE (see FIG. 15).

Example 3: Conjugation of Deglycosylated (Q295) and Aglycosylated (N$_{297}$Q) Antibodies With Primary Amine Azide The deglycosylated Q295-antibody from Example 1 or aglycosylated N$_{297}$Q-antibody was diluted in BupH (initial pH 7.6-7.8) to a concentration of 2-3 mg/mL and then mixed with ≥200 molar equivalents of azido-dPEG$_3$-amine (MW 218.26; H$_2$N—(CH$_2$—CH$_2$O)$_3$-CH$_2$—CH$_2$—N$_3$ in DMSO (0.5 g/mL) The resulting solution was mixed with MTG (25 U/mL in BupH; 5 U/mg of antibody). The final concentrations of the antibodies were 0.5-3 mg/mL. The solution was incubated at 37° C. for 4-24 hours while gently shaking. The reactions were monitored by SEC, SDS-PAGE, and/or ESI-MS.

Specifically, a deglycosylated Q295-antibody (4.7 mg/2.3 mL) in BupH (initial pH 7.6) was mixed with 200 molar equivalents of the azido-dPEG$_3$-amine (MW 218.26) and then incubated with MTG 25 U/mL in BupH (initial pH 7.6) at 37° C. for 24 hours while gently shaking. An aglycosylated antibody (3.5 mg/2.8 mL) in BupH (initial pH 7.6) was incubated with 200 molar equivalents of the azido-dPEG$_3$-amine (MW 218.26) and MTG 25 U/mL in BupH (initial pH 7.6). The reaction was incubated at 37° C. for 24 hours while gently shaking.

Upon reaction completion, the excess amine and MTG were removed by SEC (AKTA explorer, Superdex 200 PG, 1.6×60 cm, GE Healthcare, flow rate 1 mg/mL, PBSg, pH 7.4) to generate an azido-functionalized glutaminyl-modified antibody. For preparation of a large batch of azido-functionalized antibodies, the reaction mixture was loaded onto a Protein A column (Protein A FF, Hi Trap™, 1 mL or 5 mL, GE healthcare), and washed with 50 mM Tris, 150 mM NaCl, pH 7.5, to remove unreacted MTG and unreacted azido amine. Subsequently the azido-functionalized antibody was eluted with IgG elution buffer (Thermo Scientific) at a flow rate of 0.5 mL/min, and the eluted solution pH was adjusted using 1M Tris-HCl to pH 8.5 (0.10 mL 1M Tris-HCl, pH 8.5 for 1 mL of IgG elution buffer). The azido-functionalized glutaminyl-modified antibodies were obtained in about 70% yields.

The resulting purified conjugates were further analyzed by SDS-PAGE and MALDI-MS and/or ESI-MS, and showed DAR (MALDI)≥1.9 for deglycosylated antibody conjugations and DAR (MALDI)≥3.95 for aglycosylated antibody conjugations with azido-dPEG$_3$-amine, indicating near-stoichiometric conjugations.

All mass additions to the antibodies were confirmed by intact ESI-MS (see details in Example 8). For a deglycosylated antibody, addition of azido-dPEG$_3$-amine to two Q295-sites resulted in a 402 Da increase in its total molecular weight. For an aglycosylated antibody, addition of azido-dPEG$_3$-amine to two Q295- and two N297Q-sites resulted in an 804 Da increase in its total molecular weight. The final product was formulated in PBSg (10 mM phosphate, 150 mM sodium chloride, 5% glycerol, pH 7.4) in 1-10 mg/mL, and stored in a −80° C. freezer.

Example 4: Synthesis of DIBAC-Suc-PEG$_4$-VC-PAB-MMAE ("LP1"; FIG. 1)

Synthesis of tert-butyl 1-hydroxy-3,6,9,12-tetraoxapentadecan-15-oate (2): To a solution of tetraethylene glycol 1 (58.3 g, 300 mmol) in dry THF (200 mL) was added sodium (115 mg), and the mixture was stirred until sodium was consumed. To the resulting solution was then added tert-butyl acrylate (12.8 g, 100 mmol) in dry THF (50 mL) dropwise, and the resulting mixture was stirred overnight. The reaction was quenched with AcOH (0.1 mL) and water (0.5 mL) and stirred for 0.5 h, and was then extracted with ethyl acetate (200 mL×3). The combined organics were worked up by a standard procedure to give a clear oil product 2 (26 g, 81%). ESI m/z: 340 (M+18)$^+$.

Synthesis of tert-butyl 1-(methanesulfonyloxy)-3,6,9,12-tetraoxapentadecan-15-oate (3): To a solution of tert-butyl-1-hydroxy-3,6,9,12-tetraoxapentadecan-15-oate 2 (26.2 g, 81.3 mmol), TEA (12.4 mL, 89.4 mmol) in DCM (150 mL) in an ice-water bath was added a solution of MSCl (10.24 g, 89.4 mmol) in DCM (50 mL) dropwise. The mixture was stirred for 3 hours and was then concentrated. The residue was worked up by a standard procedure to give a light yellow oil product 3 (31 g, 95%). ESI m/z: 418 (M+18)$^+$.

Synthesis of tert-butyl 1-azido-3,6,9,12-tetraoxapentadecan-15-oate (4): To a solution of 3 (27 g, 67.4 mmol) in DMF (70 mL) was added NaN$_3$ (6.57 g, 101.1 mmol), and the mixture was heated at 80° C. for 4 h. After the reaction was cooled to room temperature, the mixture was diluted with ethyl acetate (150 mL) and washed with water (30 mL). The organics were worked up by a standard procedure and purified by silica gel column chromatography (petroleum ether/ethyl acetate with 1% to 2% methanol=4/1) to give a colorless oil product 4 (18 g, 67%). ESI m/z: 365 (M+18)$^+$.

Synthesis of tert-butyl 1-amino-3,6,9,12-tetraoxapentadecan-15-oate (5): To a solution of 4 (18 g, 51.8 mmol) in MeOH (100 mL) was added Pd/C (10%, 300 mg) and the mixture was purged with H$_2$ and stirred under an H$_2$ balloon at room temperature for 1 hour. The mixture was then filtered through Celite and washed with MeOH (20 mL). The filtrate was concentrated, resulting in a yellow oil product 5 (16 g, 96%). ESI m/z: 322 (M+H)$^+$.

Synthesis of 1-amino-3,6,9,12-tetraoxapentadecan-15-oic acid (6): To a solution of 5 (321 mg, 1.0 mmol) in DCM (5 mL) was added TFA (5 mL). The mixture was stirred at room temperature for one hour, and then was concentrated to remove DCM and TFA, resulting in a yellow oil crude product 6 (265 mg). ESI m/z: 266 (M+H)$^+$.

Synthesis of 1-(4-{2-azatricyclo[10.4.0.0.4,9]hexadeca-1 (12),4(9),5,7,13,15-hexaen-10-yn-2-yl}-4-oxobutanamido)-3,6,9,12-tetraoxapentadecan-15-oic acid (8): To a mixture of 7 (1.0 g, 2.48 mmol) and 1-amino-3,6,9,12-tetraoxapentadecan-15-oic acid 6 (659 mg, 2.48 mmol) in DMF (10 mL) was added triethylamine (502 mg, 4.98 mmol). The mixture was stirred at room temperature overnight followed by standard workup. The mixture was directly purified by reversed phase flash chromatography (0-100% acetonitrile in water (NH$_4$HCO$_3$, 10 mM) to give a brown oil product 8 (1.0 g, 73%). ESI m/z: 553.3 (M+1). $^1$H NMR (400 MHz, CDCl$_3$) δ 7.65 (d, J=7.2 Hz, 1H), 7.60 (m, 1H), 7.46 (m, 3H), 7.35 (m, 2H), 7.26 (m, 1H), 5.12 (d, J=13.6 Hz, 1H), 3.72 (m, 3H), 3.57 (m, 12H), 3.44 (m, 2H), 3.32-3.25 (m, 2H), 2.73 (m, 1H), 2.53 (m, 2H), 2.40-1.94 (m, 4H).

Synthesis of {4-[(2S)-2-[(2S)-2-[1-(4-{2-azatricyclo[10.4.0.04,9]Hexadeca-1 (12),4 (9), 5,7,13, 15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N—[(1 S)— 1-{[(1 S)—1{[(3R,4S,5S)-1-[(2 S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (LP1): A mixture of 8 (5.09 mg, 9.2 μmol), VC-MMAE (6.9 mg, 6.14 μmol), HATU (3.5 mg, 9.2 μmol) in DMF (1 mL) mixed with DIPEA (1.7 mg, 13.4 μmop. The mixture was stirred at room temperature overnight and purified by prep-HPLC (NH$_4$HCO$_3$ as buffer) to give a white solid product (2.0 mg, 19.6%). ESI m/z: 829.7 (M/2+H). $^1$H NMR (500 MHz, DMSO-d$_6$) δ 9.98 (s, 1H), 8.29 (s, 1H), 8.11 (d, J=7.3 Hz, 1H), 8.04 (s, 1H), 7.92-7.82 (m, 2H), 7.75 (t, J=5.1 Hz, 1H), 7.68 (d, J=7.2 Hz, 1H), 7.65-7.53 (m, 3H), 7.53-7.42 (m, 3H), 7.41-7.22 (m, 9H), 7.22-7.10 (m, 1H), 6.06-5.91 (m, 1H), 5.75 (s, 1H), 5.40 (s, 2H), 5.33 (d, J=4.8 Hz, 1H), 5.15-4.91 (m, 3H), 4.79-4.57 (m, 1H), 4.54-4.46 (m, 1H), 4.46-4.32 (m, 2H), 4.32-4.17 (m, 2H), 4.08-3.88 (m, 2H), 3.67-3.53 (m, 4H), 3.50-3.40 (m, 12H), 3.27-3.15 (m, 8H), 3.14-2.91 (m, 8H), 2.91-2.80 (m, 3H), 2.62-2.53 (m, 1H), 2.41-2.33 (m, 2H), 2.32-2.19 (m, 2H), 2.17-2.05 (m, 2H), 2.05-1.90 (m, 4H), 1.86-1.65 (m, 5H), 1.64-1.52 (m, 2H), 1.52-1.40 (m, 2H), 1.39-1.27 (m, 2H), 1.07-0.95 (m, 6H), 0.90-0.67 (m, 26H).

Example 5: General Procedure for Analyzing Small Molecules

Reagents and solvents used can be obtained from commercial sources such as Sinopharm Chemical Reagent Co. (SCRC), Sigma-Aldrich, Alfa, or other vendors.

$^1$H NMR and other NMR spectra were recorded on Bruker AVIII 400 or Bruker AVIII 500. The data were processed with Nuts software or MestReNova software, measuring proton shifts in parts per million (ppm) downfield from an internal standard tetramethyl silane.

HPLC-MS measurement were run on an Agilent 1200 HPLC/6100 SQ System using the follow conditions:

Method A: Mobile Phase: A: Water (0.01% TFA), B: acetonitrile (0.01% TFA); Gradient Phase: 5% of B increase to 95% of B within 15 min; Flow Rate: 1.0 mL/min; Column: SunFire C18, 4.6×50 mm, 3.5 μm; Column Temperature: 50° C. Detectors: ADC ELSD, DAD (214 nm and 254 nm), ES-API.

Method B: Mobile Phase: A: Water (10 mM NH$_4$HCO$_3$), B: acetonitrile; Gradient Phase: 5% to 95% of B within 15 min; Flow Rate: 1.0 mL/min; Column: XBridge C18, 4.6×50 mm, 3.5 μm; Column Temperature: 50° C. Detectors: ADC ELSD, DAD (214 nm and 254 nm), MSD (ES-API).

LC-MS measurement was run on an Agilent 1200 HPLC/6100 SQ System using the follow conditions:

Method A: Instrument: WATERS 2767; column: Shimadzu Shim-Pack, PRC-ODS, 20×250 mm, 15 μm, two connected in series; Mobile Phase: A: Water (0.01% TFA), B: acetonitrile (0.01% TFA); Gradient Phase: 5% of B increase to 95% of B within 3 min; Flow Rate: 1.8-2.3 mL/min; Column: SunFire C18, 4.6×50 mm, 3.5 μm; Column Temperature: 50° C. Detectors: ADC ELSD, DAD (214 nm and 254 nm), ES-API.

Method B: Instrument: Gilson GX-281; column: Xbridge Prep C18 10 um OBD, 19×250 mm; Mobile Phase: A: Water (10 mM NH$_4$HCO$_3$), B: Acetonitrile; Gradient Phase: 5% to 95% of B within 3 min; Flow Rate: 1.8-2.3 mL/min; Column: XBridge C18, 4.6×50 mm, 3.5 μm; Column Temperature: 50° C. Detectors: ADC ELSD, DAD (214 nm and 254 nm), MSD (ES-API).

Preparative high-pressure liquid chromatography (Prep-HPLC) in an acidic system was operated on a Gilson GX-281. Two solvent systems were commonly used. Acidic solvent system used a Waters SunFire 10 μm C18 column (100 Å, 250×19 mm); and solvent A for prep-HPLC was water/0.05% TFA and solvent B was acetonitrile. The elution conditions were a linear gradient increase of solvent B from 5% to 100% over a time period of 20 minutes at a flow rate of 30 mL/min. A basic solvent system used a Waters Xbridge 10 μm C18 column (100 Å, 250×19 mm), and solvent A used for prep-HPLC was water/10 mM ammonium bicarbonate (NH$_4$HCO$_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed-phase flash chromatography was performed on a Biotage instrument, with Boston ODS or Agela C18 cartridges.

Example 6: Synthesis of Site-Specific Conjugated ADC Via Click Reactions

The azido-functionalized glutaminyl-modified antibodies of Example 3 were treated with linker-payload compounds. The azido-functionalized antibody at 0.5-2 mg/mL in PBSg (PBS, 5% glycerol, pH 7.4) was treated with 3-4 molar equivalents of DIBAC-Suc-PEG$_4$-VC-PABC-MMAE (Example 4, LP1, MW 1658.07; conc. 5 mg/mL in DMSO) at 24° C. for 5-8 hours to make 2DAR ADCs, or 4-6 molar equivalents of LP1 (MW 1658.07; 5 mg/mL in DMSO) to make 4DAR ADCs. The excess amount of linker-payload (Example 4) was removed by SEC (AKTA explorer, Superdex 200 PG, 1.6×60 cm, GE Healthcare, flow rate: 1 mg/mL, PBSg, pH 7.4) eluting with PBSg. The products were analyzed by SEC, SDS-PAGE, and ESI-MS/MALDI-MS.

A summary of the ADCs with 2DAR are listed below. A specific preparation of the azido functionalized deglycosylated antibody-LP1 conjugation was conducted from the incubation of azido-functionalized glutaminyl-modified antibody (3.7 mg/6.8 mL) in PBSg with 3.5 molar equivalents of LP1 (5 mg/mL in DMSO, 0.03 mL) at 24° C. for 6 hours.

| Deglycosylated ADCs | Antigen Target | DAR (MALDI) |
|---|---|---|
| Ab$_{Q295}$-PEG$_3$-DIBACT-PEG$_4$-VC-pAB-MMAE | HER2 | 1.96 |
| Ab$_{Q295}$-PEG$_3$-DIBACT-PEG$_4$-VC-pAB-MMAE | PRLR | 1.90 |

A summary of the ADCs with 4DAR are listed below. A specific preparation of the azido-functionalized aglycosylated antibody-LP1 conjugation was conducted from azido-functionalized glutaminyl-modified antibody (3.1 mg/12 mL) in PBSg with 4.2 molar equivalents of LP1 (5 mg/mL in DMSO, 0.03 mL) at 24° C. for 6 hours.

| Aglyosylated ADCs | Antigen Target | DAR (MALDI) |
|---|---|---|
| Ab$_{Q295/Q297}$-PEG$_3$-DIBACT-PEG$_4$-VC-pAB-MMAE | HER2 | 4.00 |
| Ab$_{Q295/Q297}$-PEG$_3$-DIBACT-PEG$_4$-VC-pAB-MMAE | PRLR | 4.00 |
| Ab$_{Q295/Q297}$-PEG$_3$-DIBACT-PEG$_4$-VC-pAB-MMAE | STEAP2 | 4.00 |

Example 7: Synthesis of Non Site-Specific ADC Conjugates Via Conventional Thiol-Maleimides Antibody conjugation via disulfide linkages was performed in two steps using methods similar to those for making Adcetris®-like ADCs. Briefly, a test monoclonal antibody of Fc isotype IgG1 (mAb, 10 mg/ml in 50 mM HEPES, 150 mM NaCl) at pH 7.5 was reduced with 1 mM dithiothreitol (0.006 mg per mg of antibody) or TCEP (2.5 molar equivalents to antibody) at 37° C. for 30 min. After gel filtration (G-25, pH 4.5 sodium acetate), MC-VC-pAB-MMAE in DMSO (10 mg/ml) was added to the reduced antibody, the mixture was adjusted to pH 7.0 with 1 M HEPES (pH 7.4), and allowed to react for 3-14 h. The conjugate was purified by SEC.

A summary of non site-specific ADCs via conventional thio-maleimide conjugation are listed below. The DAR (UV) values were determined using the measured absorbances of the ADC and the extinction coefficients of the antibody and the drug-linker.

| ADCs | Antigen Target | DAR (UV) |
|---|---|---|
| Ab$_1$-MC-VC-pAB-MMAE | FelD1 | 2.2 |
| Ab$_2$-MC-VC-pAB-MMAE | HER2 | 2.2 |
| Ab$_3$-MC-VC-pAB-MMAE | PRLR | 1.93 |

| ADCs | Antigen Target | DAR (UV) |
|---|---|---|
| Ab$_1$-MC-VC-pAB-MMAE | FelD1 | 3.8 |
| Ab$_3$-MC-VC-pAB-MMAE | PRLR | 3.7 |
| Ab$_4$-MC-VC-pAB-MMAE | STEAP2 | 3.3 |

Example 8: Analysis of Antibodies, Azido-functionalized Antibodies, and ADCs

Antibodies and ADCs were characterized by SEC, SDS-PAGE, MS (MALDI) and/or MS (ESI). An example of an anti-HER2 ADC from a naked antibody was characterized by SDS-PAGE performed under non-reducing and reducing conditions (FIG. 2A), SEC (FIGS. 3A-3D), and ESI-MS (FIG. 5A); and demonstrated complete deglycosylation, complete azido-functionalized antibody conjugation, and complete ADC formation via a 2+3 click cyclization. The conjugation sites were determined using NanoLC-MS/MS analysis for peptide sequence mapping (FIGS. 6A-6B).

Analysis of ADC Integrity and Purity by SDS-PAGE

SDS-PAGE conditions: non-reduced/reduced samples (2-4 µg) were loaded per lane (1.0 mm×10 well) in Novex 4-20% Tris-Glycine Gel, using 180V at 300 mA for 80 min. BenchMark Pre-Stained Protein Ladder was from Invitrogen. An analytic sample was prepared using Novex Tris-Glycine SDS buffer (2×) (Cat. No. LC2676, Invitrogen) and the reducing SDS sample buffer (2×) contained 10% 2-mercaptoethanol. The presence of a single band indicates a successful conjugation with no detectable aggregation and/or side product.

Alternatively, SDS-PAGE running conditions were at a constant 180V for 40 minutes. The gel was fixed with 50% MeOH, 8% acetic acid for 15 min and rinsed with water for 5 min prior to staining with Coomassie. Coomassie Stain was completed in <2 hrs and the gel was destained with water. Shown in FIGS. 2A and 2B were molecular weights of the antibodies on SDS-PAGE performed under non-reducing and reducing conditions. The mass shifts were not obvious under non-reducing conditions due to relatively small percentages of mass changes. However, the mass of the heavy chains were decreased from the naked antibodies to deglycosylated antibodies, and increased from the deglycosylated antibodies to the azido-functionalized antibodies, and further to the ADC conjugates.

Analysis of ADC Purity by SEC

Figure 3A:
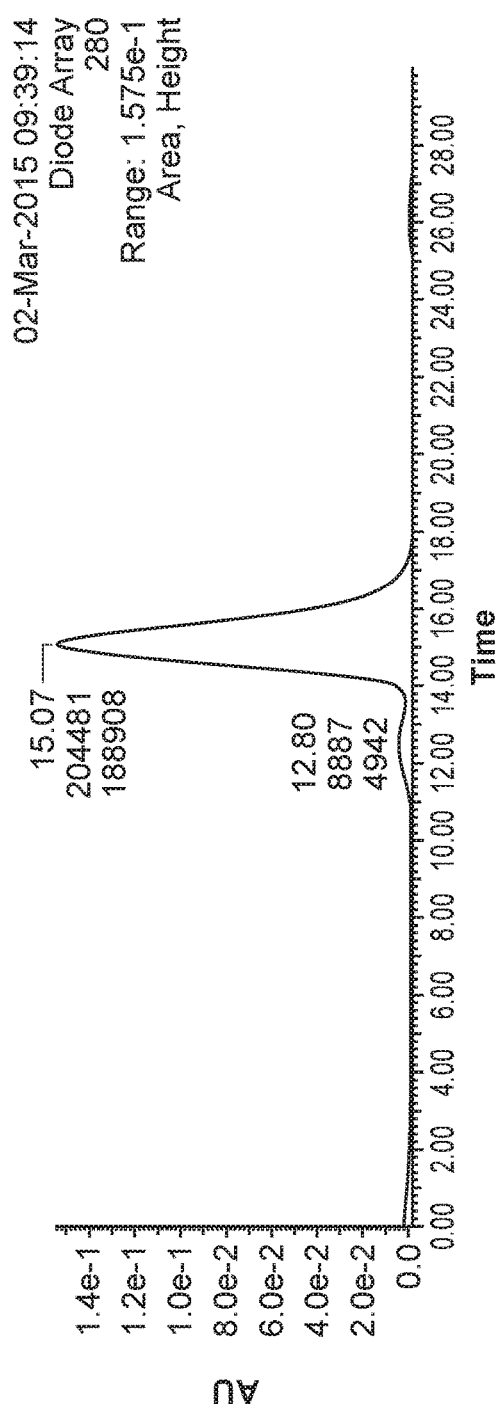
FIGS. 3A-3D show SEC results from the naked antibody to the corresponding azido-functionalized antibody and antibody linker drug conjugate, demonstrating no additional aggregation from the MTG-based conjugation.
Figure 3B:
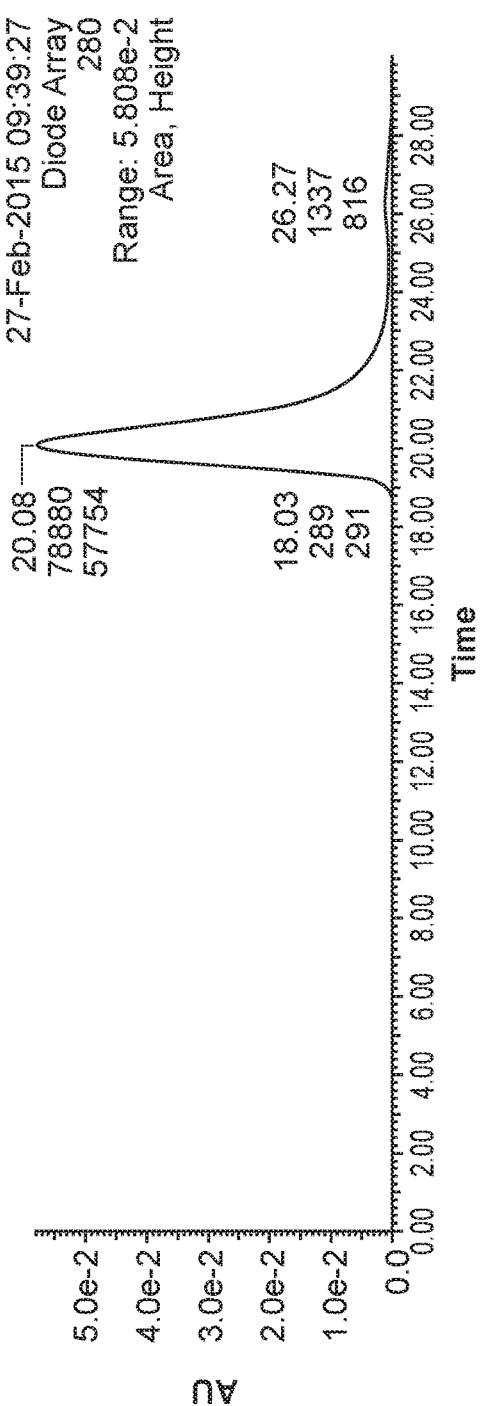
Figure 3C:
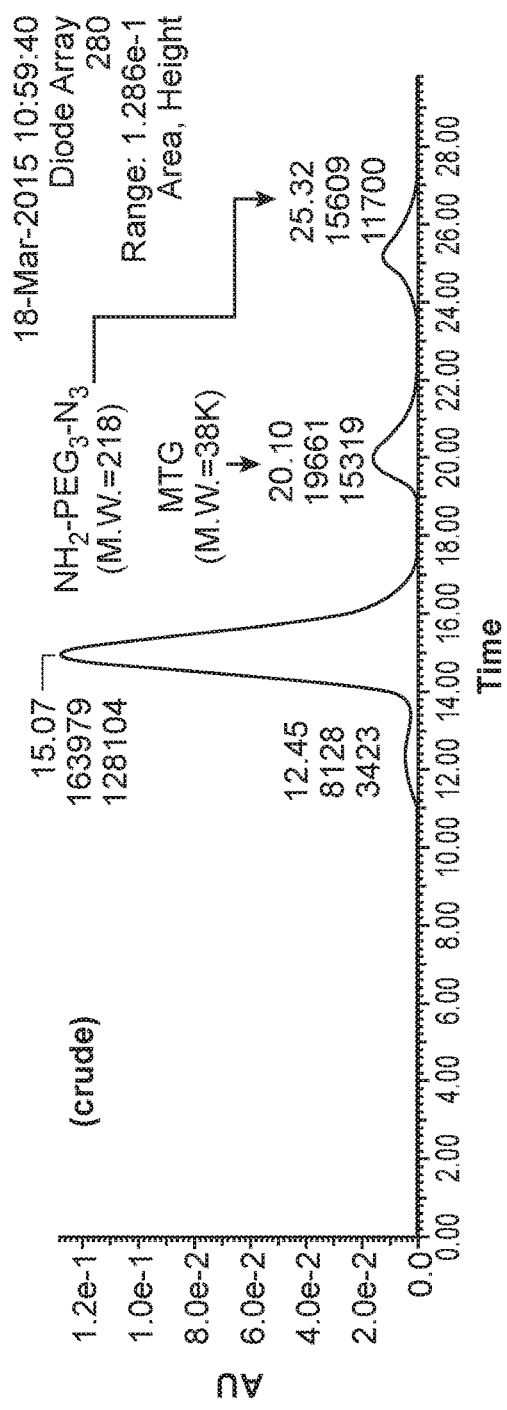
Figure 3D:
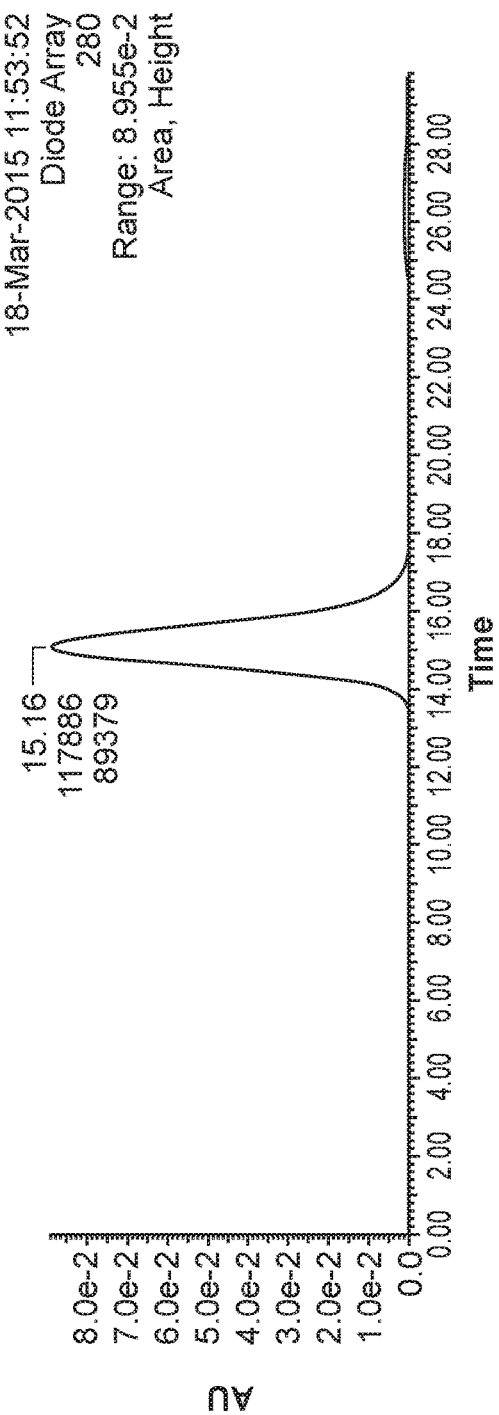

SECs were run on a Waters 600 Controller over a Superdex 200 1.0×30 cm, HR column at flow rate of 0.80 mL/min, using PBS pH 7.4; and monitored at λ 280 nm using a Waters 2998 PDA. An analytic sample was composed of 200 µL PBS (pH 7.4) with 30-100 µL of test sample. Preparative SEC purifications were performed using AKTA, GE Health-Care, Superdex 200 PG, 2.6×60 cm at a flow rate of 2 mL/min, eluting with PBSg at pH 7.4, and monitored at λ 280 nm. Shown in FIG. 3A is naked anti-HER2 mAb with 4% aggregate; 3B is MTG, 3C is a crude mixture with 4% aggregate after MTG-based conjugation; 3D is final SEC purified ADC with <0.5% aggregate, indicating the MTG-based conjugation did not cause any additional aggregation.

Intact Mass Analysis by MALDI-TOF

A MALDI-TOF instrument was used for intact protein analysis. Each protein/conjugate (13 µL, 1 mg/mL) was desalted by passing through a Zeba Micro Spin desalting column that was pre-equilibrated with 0.1% TFA. Each desalted protein/conjugate sample (5 µL) was mixed with 5 µL matrix (sinapinic acid in 70% $C_H3CN$; 0.1% TFA; 10 mg/mL) and 2 µL was spotted in duplicate on a steel MALDI plate. The protein spots were analyzed on a Bruker Ultraflex II MALDI-TOF instrument (Bruker Daltonics, Bremen, Germany).

Intact Mass Analysis of Antibody and ADC by LC-ESI-MS

Measurements for intact mass of ADC samples by LCh-ESI-MS was performed to determine a drug-payload distribution profile and to calculate average DARs for intact ADC forms. Each testing sample (20-300 ng, 5 µL) was loaded onto an Acquity UPLC Protein BEH C4 column (10K psi, 300 Å, 1.7 µm, 75 µm×100 mm; Cat. No. 186003810). After desalting on a Thermo Fisher Easy Nano LC1000 (S/N: LC-011302) with RP buffer (0.1% formic acid in 2%-70% acetonitrile in water), the protein was eluted and acquired by a Qexactive mass spectrometer (Xcalibur 3.0.63, Thermo Scientific). The ESI mass spectra were deconvoluted using Protein Deconvolution 3.0 (Thermo Scientific). Alternatively, the eluted protein was acquired by a Waters Synapt 2-Si mass spectrometer (Waters) and the ESI Q-TOF mass spectra were deconvoluted to zero charge mass spectra using a Maximum Entropy algorithm (MassLynx). The resulting mass spectra demonstrated the distribution of each drug(s) conjugated as ADC. The area percentage of a peak represents the relative distribution of the particular drug-loaded ADC species. The average DAR was calculated using the percentage peak area information and the drug load numbers on the antibody.

Figure 4:
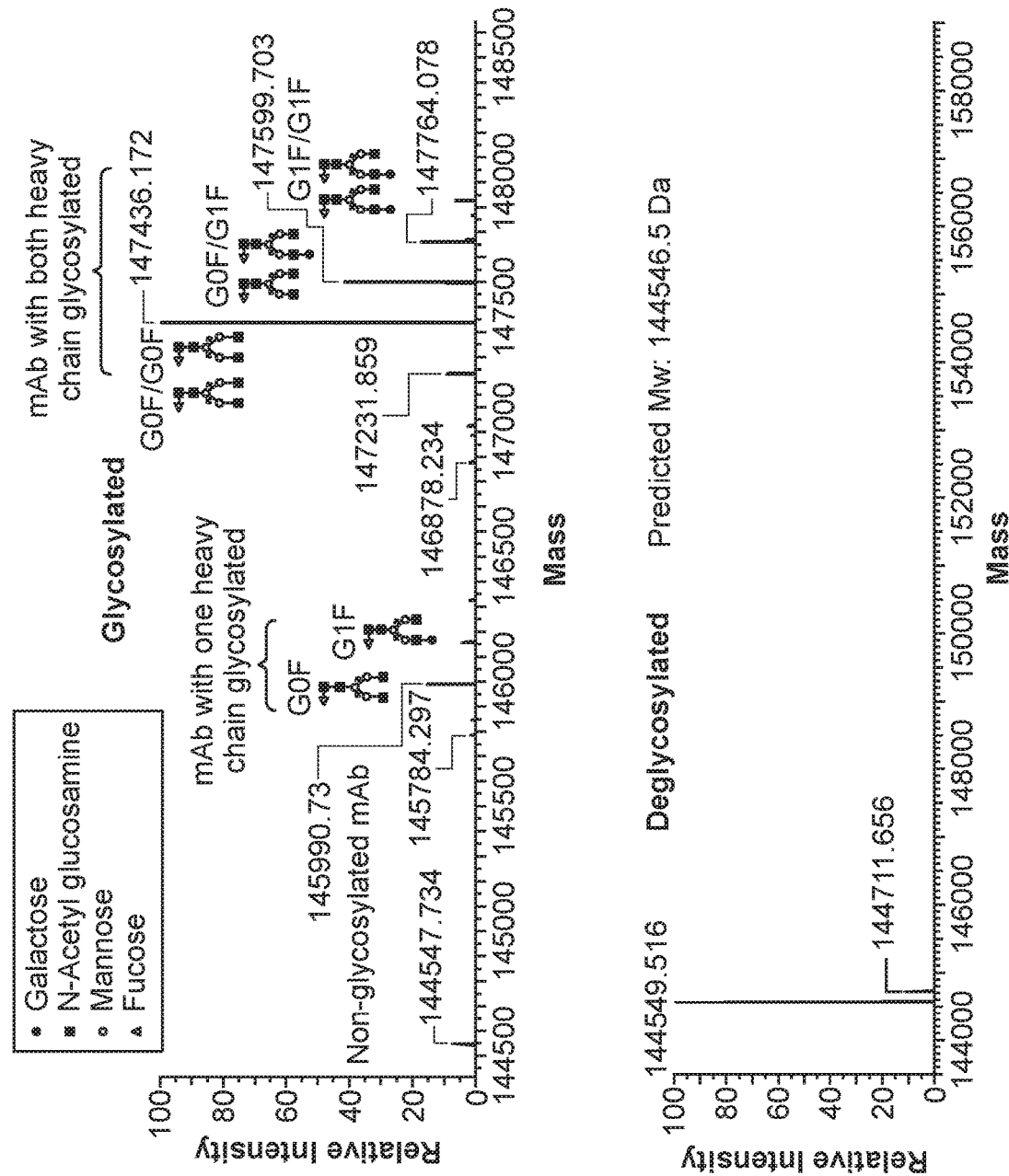
FIG. 4 shows ESI-MS data demonstrating complete deglycosylation and indicating the average molecular weight of the glycans were ~3000 Da.

The intact mass measurements of the naked anti-PRLR antibody and its deglycosylated antibody were performed to confirm complete deglycosylation by matching the molecular weight of the deglycosylated antibody with the predicted molecular weight based on the cDNA-derived amino acid sequence, assuming removal of the C-terminal $Lys^{450}$ from each HC, formation of 16 disulfide bonds, and conversion of $Asn^{300}$ to $Asp^{300}$ on the HC due to the deglycosylation. As shown in FIG. 4, the deconvoluted mass spectrum exhibited a predominant peak, indicating the molecular weight of the deglycosylated anti-PRLR antibody was 144549.5 Da. This experimental mass matched well with the predicted protein mass 144546.5 Da (≤20 ppm). There were several forms of the naked antibody and the molecular weight of the most abundant mass was 147436.1 Da, indicating the molecular weight of the abundant glycan was about 2886 Da.

The intact mass measurement for the deglycosylated anti-HER2 antibody and its LP1-ADC (FIG. 5A) and aglycosylated anti-HER2 antibody as well as azido-functionalized antibody and its LP1-ADC (FIG. 5B) were performed to confirm complete azido-functionalized antibody conjugation and ADC click-cyclization to determine a drug-payload distribution profile and to calculate an average DAR for the intact ADC forms.

Figure 5A:
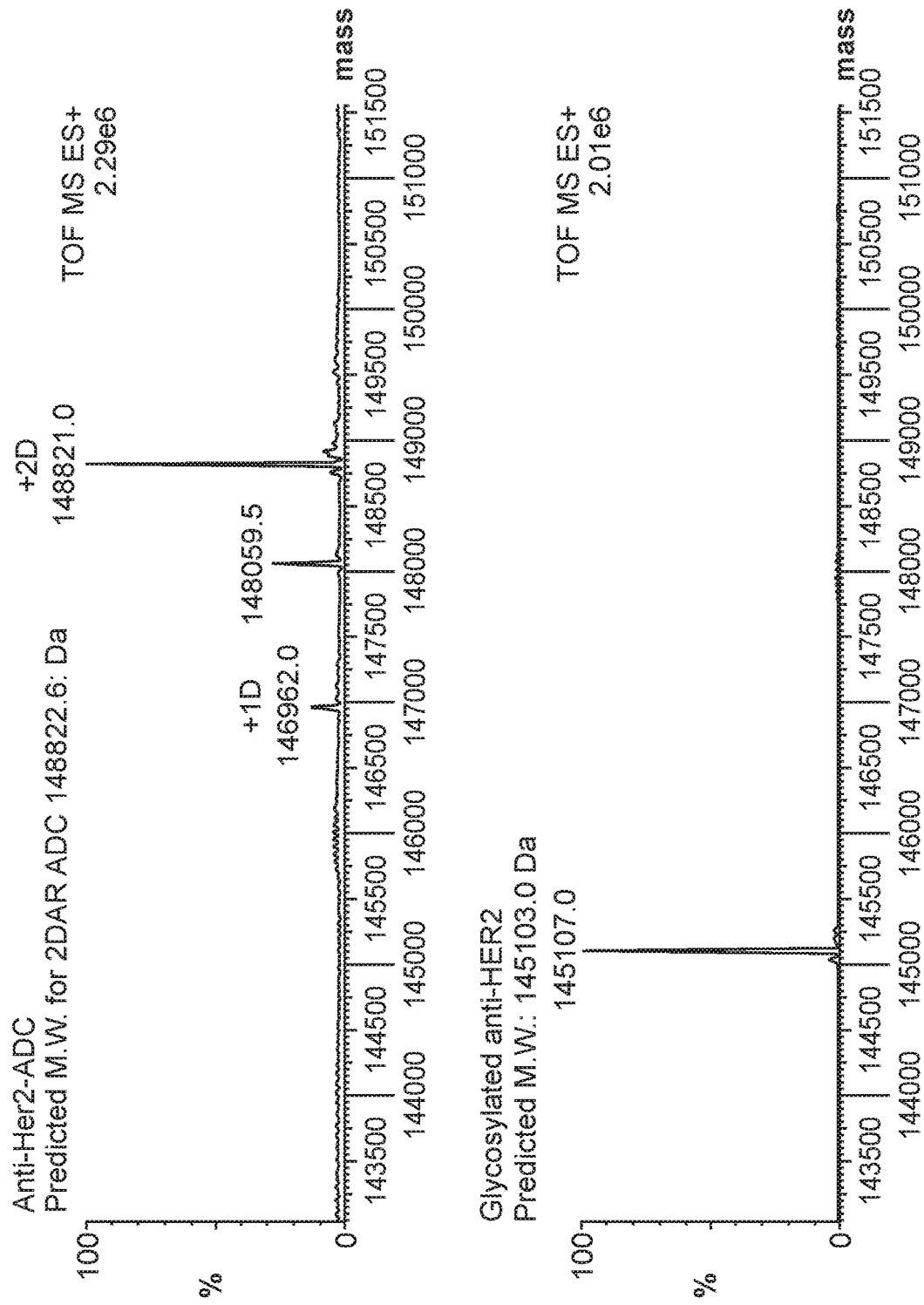
FIGS. 5A and 5B show ESI-MS data demonstrating the molecular weight change from the naked antibody to the antibody linker drug conjugate.
Figure 6A:
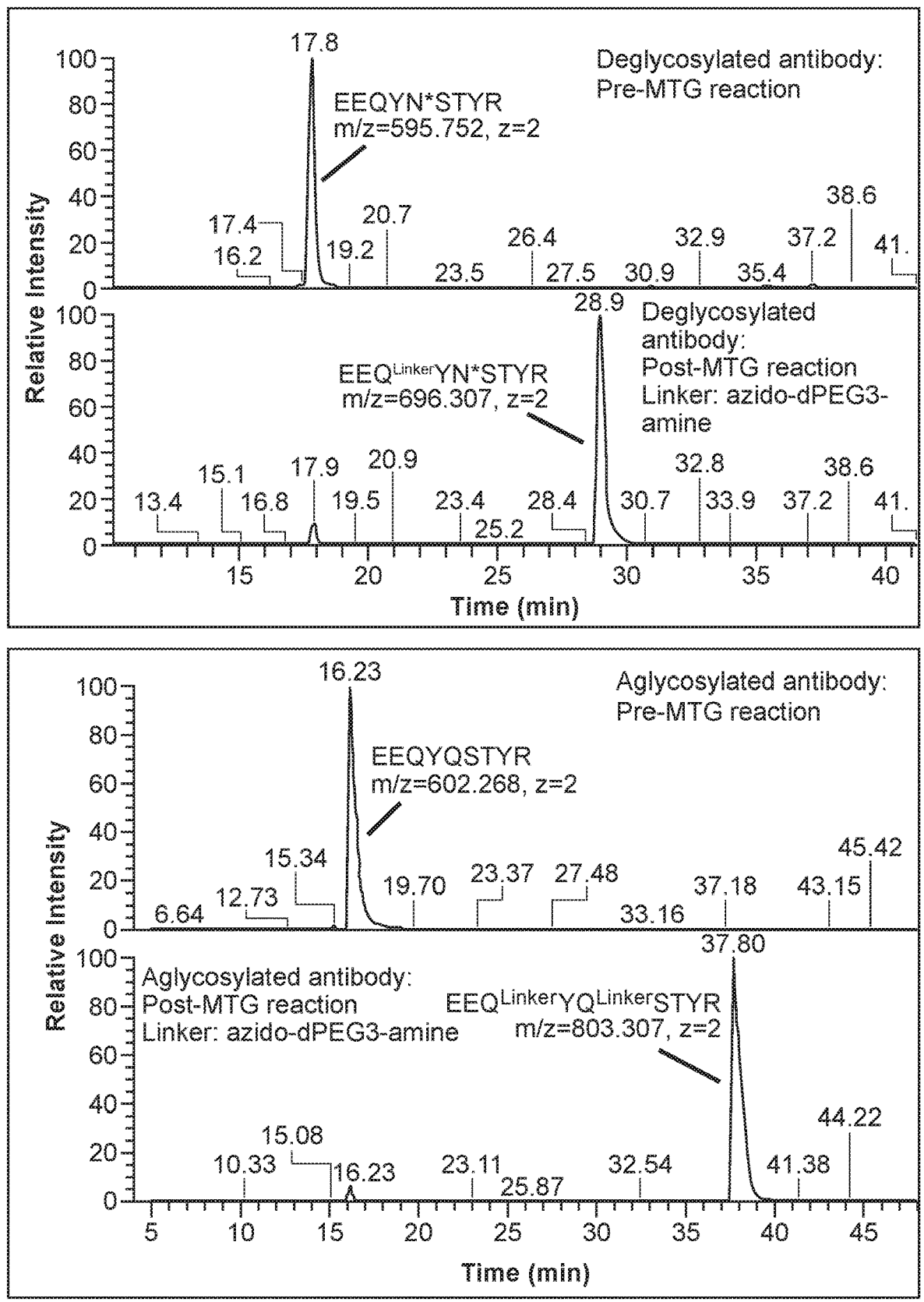
FIGS. 6A and 6B provide nano-LC-MS/MS analysis to identify and confirm the conjugation sites.
Figure 6B:
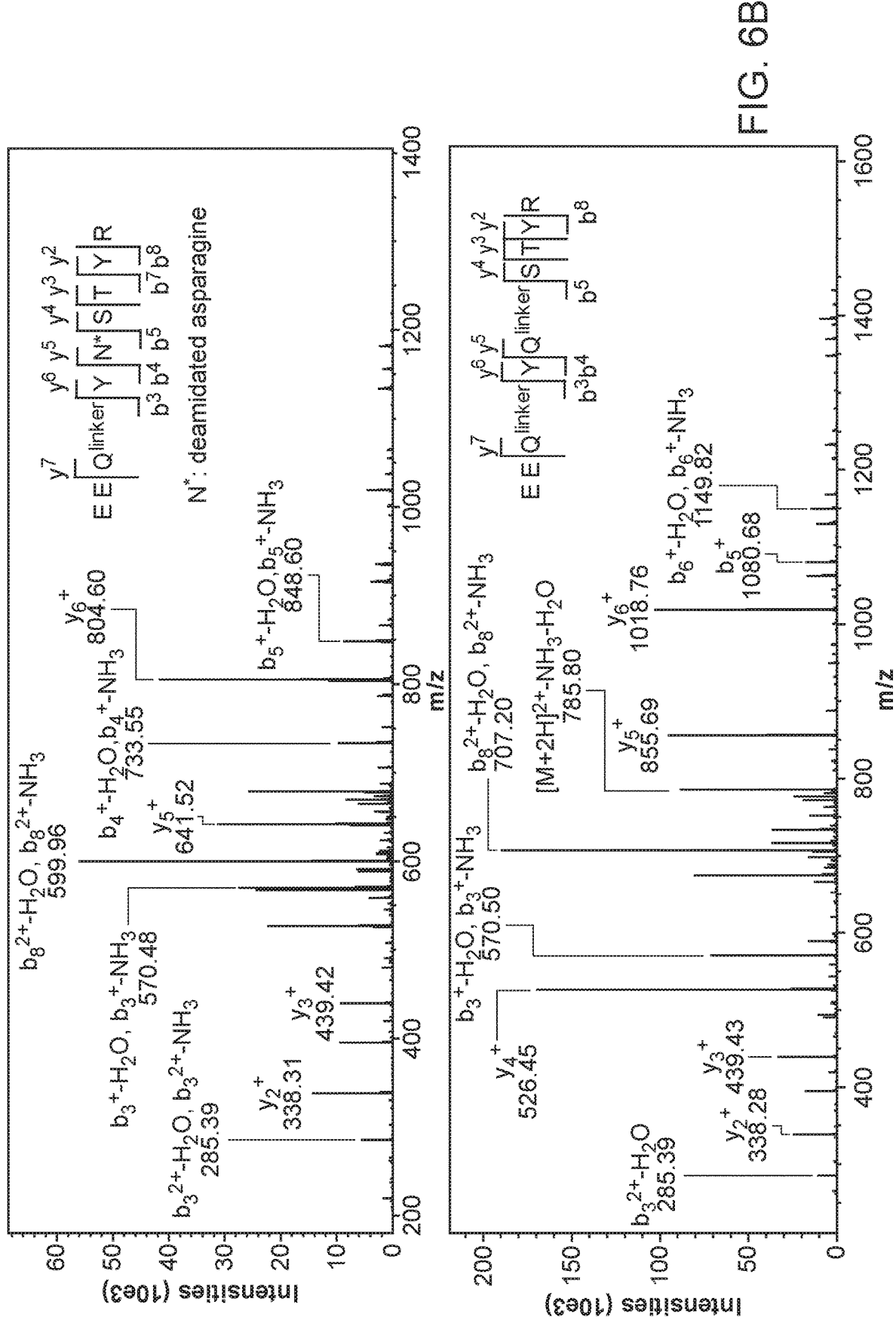

As shown in FIG. 5A, the deconvoluted mass spectrum for deglycosylated anti-HER2-LP1 (ADC) exhibited three peaks corresponding to molecular weights ranging from 146,500 to 149,500 Da. The first mass peak with a mass of 148,821.0 Da was the most abundant species. The mass difference between the first mass (148,821.0 Da) and the antibody (145103.0 Da) was approximately 3718.0 Da, corresponding to the mass of two linker-payloads (MW 1859.0 Da) added to one antibody. The mass difference between the third mass (146962.0 Da) and the antibody (145103.0 Da) was approximately 1859.0 Da, corresponding to the mass of one linker-payload (MW 1859.0 Da) added to one antibody. The second mass peak with a mass of 148,059.5 Da was 761.5 Da lower compared to the most abundant first mass peak and less than the mass of the linker-payload (1859.0 Da), suggesting in-source fragments of the ADC in the ion source of the ESI mass spectrometer. The average DAR (ESI) for the anti-HER2-LP1 was 1.91.

Figure 5B:
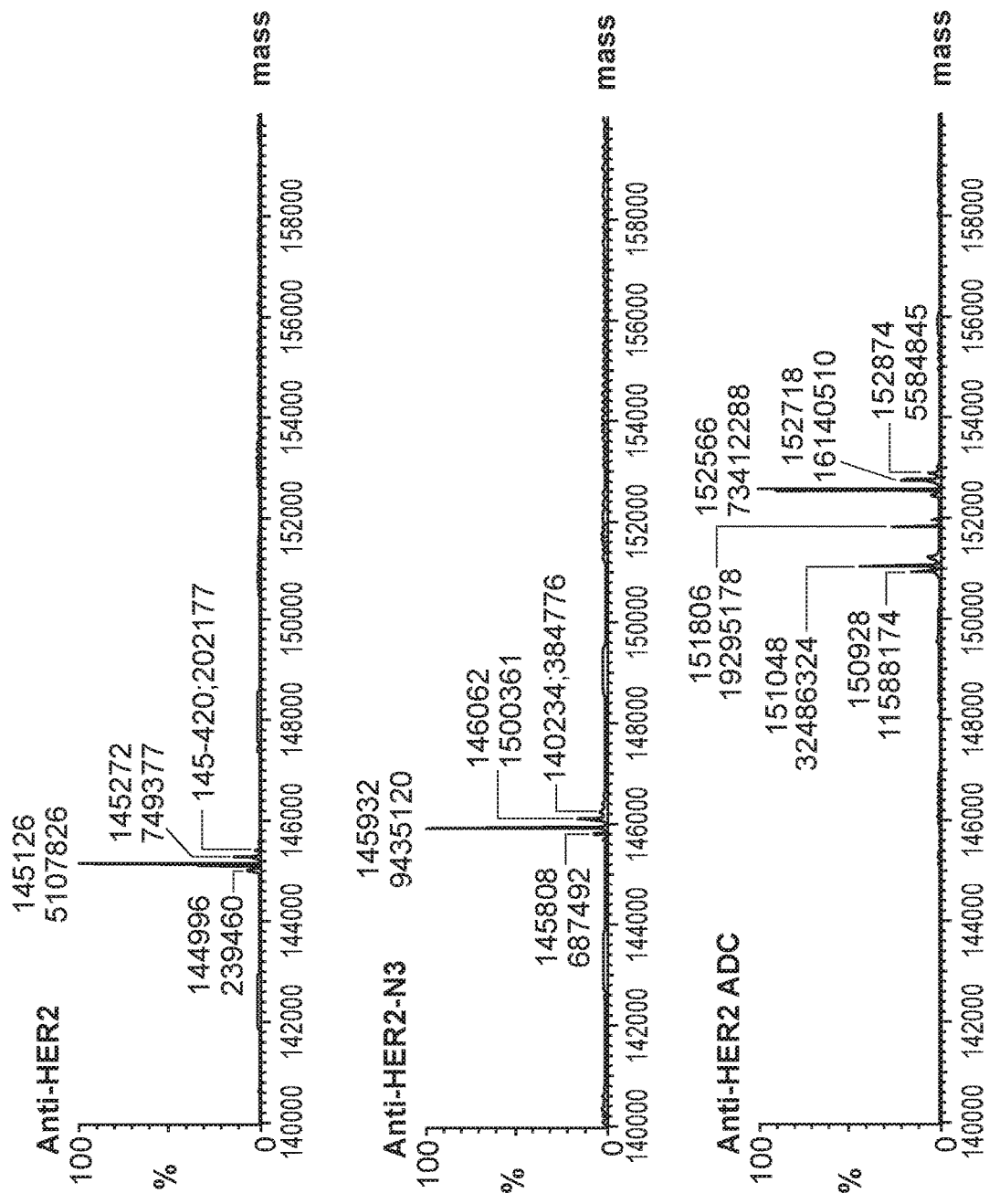

As shown in FIG. 5B (top and middle), the deconvoluted mass spectra exhibited a predominant peak for the aglycosylated anti-HER2 antibody with molecular weight of 145126.0 Da, and a predominant peak for its azido-functionalized anti-HER2 antibody with molecular weight of 1455932.0 Da, indicating a 806.0 Da increase compared to its aglycosylated antibody (corresponding to 4 amino-$PEG_3$-azide conjugations to each aglycosylated antibody). As also shown in FIG. 5B (bottom), the anti-HER2-LP1 (ADC) exhibited three peaks corresponding to the molecular weights of 152566.0, 151504.0, and 151050.0 Da. The first mass peak with a mass of 152566.0 Da was the most abundant species. The mass difference between the first mass peak (152566.0 Da) and the antibody (145126.0 Da) was approximately 7440.0 Da, corresponding to the mass of four linker-payloads (MW 1858.0 Da) added to one antibody. The mass difference between the first mass peak (152566.0 Da) and the third mass peak (151050.0 Da) was 1516.0 Da, and the mass difference between the first mass peak (152566.0 Da) and the second mass peak (151504.0 Da) was 762 Da, which were less than the mass of the linker-payload (1858.0 Da) and were also less abundant than the first mass peak, representing in-source fragments of the ADC in the ion source of the ESI mass spectrometer. The average DAR (ESI) for the anti-HER2-LP1 was 4.0.

MALDI-MS Analysis for DAR Value Measurement

The DAR values of the azido-functionalized antibody from MTG-catalyzed conjugation were assessed by antibody in-gel digestion followed by MALDI-MS analysis. The azido-functionalized antibody and native antibody (2 µg) were reduced by 2-mercaptoethanol and separated on a homemade Tris-Glycine SDS-PAGE gel. After the gel was stained with Simply Blue SafeStain (Life Technologies, Carlsbad, Calif.), the heavy and light chain bands of the antibodies and ADCs were excised. The gel pieces were destained with 50% acetonitrile/50% 50 mM ammonium bicarbonate for 30 min at 37° C. The gel pieces were dehydrated with 100% acetonitrile followed by rehydrating in 100 µL of freshly prepared 65 mM dithiothreitol (DTT) in 50 mM $NH_4HCO_3$ for 30 min at 37° C. The DTT solutions were discarded and the pieces were incubated in 100 µL of freshly prepared 135 mM iodoacetamide (IAM) in 50 mM $NH_4HCO_3$ at room temperature in the dark for 30 min. The gel pieces were washed with 50% acetonitrile/50% 50 mM $NH_4HCO_3$, and then with 100% acetonitrile. The acetonitrile was discarded and the dried gel pieces were rehydrated in modified trypsin (Promega, Madison, Wis.)/50 mM $NH_4HCO_3$ and incubated at 37° C. overnight. The digested peptides were spotted on a Bruker Anchorchip MALDI plate with matrix (α-cyano-4-hydroxycinnamic acid, Protea Biosciences). The peptide spots were analyzed on a Bruker Ultraflex II MALDI-TOF instrument (Bruker Daltonics, Bremen, Germany). The heavy chain of a native antibody digested by trypsin produced two well-resolved peaks at m/z 1186.574 and 1190.496. The 1190.496 peak represents the target peptide EEQ295YNSTYR (SEQ ID NO:1), whereas the 1186.574 peak represents peptide LSCGASGFTFR (SEQ ID NO:2). Peptide LSCGASGFTFR (SEQ ID NO:2) is not susceptible to any modification during the MTG reaction. Therefore, this peptide was selected as an internal standard peptide to calculate the conjugation yields. The intensities of the 1186 and 1190 peaks in unmodified heavy chains were denoted as $P_1$ and $P_2$; the intensities of these peaks in linker-modified heavy chain were denoted as $P_1'$ and $P_2'$, respectively. The DAR was calculated as $2 \times (1 - P_2' \cdot P_1 / P_2 \cdot P_1')$. This method was used to calculate the DARs for Q295 site-specific modifications with various linkers to an antibody.

NanoLC-MS/MS Analysis for Peptide Sequence Mapping

Nano-LC-MS/MS analysis was exploited to identify site-specific modification of glutamine residues in ADCs. The azido-functionalized antibodies (2 µg) or native antibody were digested as described in MALDI-MS analysis for DAR measurements. After the digestion was complete, the peptides were extracted with 50% acetonitrile/5% formic acid solution. The extracts were pooled and dried to completion in SpeedVac. The dried peptides were reconstituted in 0.1% TFA prior to NanoLC-MS/MS analysis.

Each sample was analyzed by an Elite mass spectrometer (Thermo Fisher Scientific, San Jose, Calif.) with an Easy NanoLC-1000 system. Peptides were trapped on a 75 um inner diameter "Acclaim PepMap 100" column packed with C18 resin (3 µm, 100 Å, Thermo Fisher), and then separated on a 75 µm inner diameter "PepMap RSLC" column (25 cm, C18, 2 µm, 100 Å, Thermo Fisher). Peptides were separated using a 60 min gradient of 2-45% acetonitrile in 0.1% formic acid with a flow rate of 250 nl/min. The eluted peptides were analyzed using data-dependent acquisition of one MS scan followed by MS/MS scans for the ten most abundant ions.

Following data acquisition, ThermoFisher RAW data files were processed using Proteome Discoverer 1.4 and searched against an antibody sequence database using a Mascot search algorithm (Matrix Science, Boston, USA). All searches assumed trypsin digestion with up to 1 miscleavage site, and considered carboxymethylation of cysteine as a fixed modification, and oxidation of methionine and deamidation of glutamine and asparagine as variable modifications. In addition, glutamine modification by azido-$dPEG_3$-amine was uploaded into the database and searched as a variable modification, and mass spectra for drug peptides conjugates were manually inspected to identify drug-peptide conjugates.

The MS results of the deglycosylated antibodies (FIG. 6A, top) showed a complete conversion of EEQYN*STYR (SEQ ID NO: 5) to $EEQ^{Linker}YN^*STYR$ (SEQ ID NO: 6) for 2DAR ADC (N* represents deamidated asparagine) or EEQYQSTYR (SEQ ID NO: 8) to $EEQ^{Linker}YQ^{Linker}STYR$ (SEQ ID NO: 7) for 4DAR ADC (FIG. 7, bottom), while the light chains remained unmodified as no mass changes were found in peptides from the light chains based on LC-MS analyses. The conjugation sites were identified by MS/MS peptide sequencing at Q295 for 2DAR ADC (FIG. 6B, top) and Q295 and Q297 for 4DAR ADC (FIG. 6B, bottom).

Peptide mappings of final ADC products confirmed that azido-antibody intermediates were completely converted to drug-conjugated antibodies at Q295 sites for 2DAR ADC and at Q295/297 sites for 4DAR ADC.

Example 9: Biacore Binding Kinetics

To determine respective binding kinetics of the ADCs and antibodies to their corresponding antigens at 25° C. Equilibrium dissociation constants (Ku) for antigen binding to ADCs and their respective unmodified parent monoclonal antibody were determined using a real-time surface plasmon resonance biosensor assay on a Biacore 2000 or 3000 instrument. The Biacore sensor surface was derivatized by amine coupling with a monoclonal mouse anti-human Fc antibody (GE Healthcare, Cat. No. BR-1008-39) to capture the ADC and parent mAb expressed with human Fc constant regions. Biacore binding studies were performed in HBS-ET running buffer (0.01 M HEPES pH 7.4, 0.15 M NaCl, 3 mM EDTA, 0.05% v/v Surfactant P20). Human antigens were produced in-house expressing a C-terminal myc-myc-hexa-histidine tag (subsequently referred to as antigen-mmh). Different concentrations of human PRLR.mmh (SEQ ID NO:3) ranging from 600 nM to 150 nM in 2-fold dilutions; and human antigen ErbB2.mmh (SEQ ID NO: 4) ranging from 50 nM to 3.12 nM in 4-fold dilutions prepared in HBS-ET running buffer were injected over the respective ADC or parent mAb captured surface at a flow rate of 50 µL/min. Association of all the antigen reagents to each of the captured ADCs or mAbs were monitored for 4 min and their dissociation in HBST running buffer was monitored for 6 to 8 min. All the binding kinetics experiments were performed at 25° C. Kinetic association ($k_a$) and dissociation ($k_d$) rate constants were determined by fitting the real-time sensor-grams to a 1:1 binding model using Scrubber 2.0c curve fitting software. Binding equilibrium constants ($K_a$) and dissociative half-lives ($t_{1/2}$) were calculated from the kinetic rate constants as:

$$K_D(M) = k_d/k_a, \text{ and } t\frac{1}{2}(\min) = \ln 2/(60 \times k_d)$$

Shown in FIG. 7 are binding kinetic parameters for human PRLR.mmh binding to anti-PRLR mAb, azido-functionalized antibody, and ADC at 25° C.; and binding kinetic parameters for human ErbB2·mmh binding to anti-ErbB2 parent mAb and ADC at 25° C. The results indicated that all ADCs showed similar binding to the antigens compared to the corresponding parental antibodies.

Example 10: Anti-HER2-ADC Cytotoxicity Assay

The ability of the site-specific anti-HER2 ADC to induce target-specific cytotoxicity was evaluated in SKBR3 and HEK293 cells. High HER2 cell surface expression is known in SKBR3 cells (see, e.g., Phillips et al., 2008, *Cancer Research* 68:9280-9290; Diessner J, et al., 2014, *Cell Death and Disease* 5(3):e1149).

Figure 8:
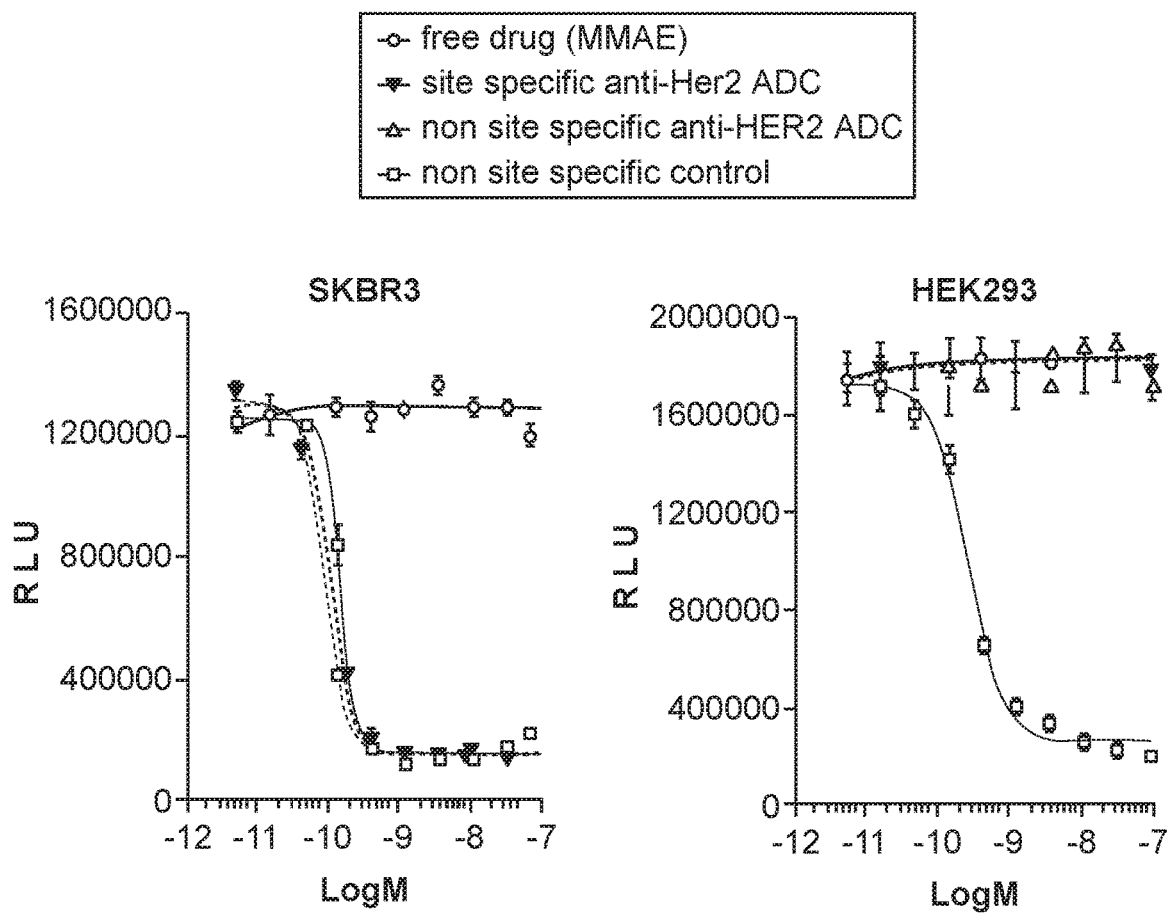
FIG. 8 shows cell killing data for site specific ADCs and controls on SK-Br-3 Her2$^+$ breast cancer cells.

In vitro cytotoxicity of anti-HER2 site-specific ADCs or anti-HER2 conventional thio-maleimide conjugated ADCs (Example 7) were evaluated using the CellTiter-Glo Assay Kit (Promega), in which the quantity of ATP present is used to determine the number of viable cells in culture. HEK293 and SKBR3 cells were seeded at 1000 cells/well in complete growth medium and grown overnight at 37° C., 5% $CO_2$ in Nunclon (Nunc) white 96-well plates. For cell viability curves, 1:3 serially diluted conjugates or free representative payloads were added to the cells at final concentrations ranging from 100 nM to 0.015 nM including a no treatment control and incubated for 3 days. Cells were incubated at room temperature with 100 ul of CellTiter-Glo reagents for 5 minutes and relative luminescence was determined on a Victor plate reader (PerkinElmer). The $IC_{50}$ values were determined from a four-parameter logistic equation over a 10-point response curve (GraphPad Prism). All curves and $IC_{50}$ values were corrected for payload equivalents. All $IC_{50}$s were expressed as nM and % kill was reported for the highest dose. As summarized in FIG. 8, the anti-HER2 site-specific ADC demonstrated cytotoxicity on SKBR3 cells comparable to the conventional thio-maleimide conjugated ADCs (Example 7) with an $IC_{50}$ of 0.11 nM and 0.09 nM, respectively. As expected, the anti-HER2 ADCs had little to no impact on HEK293 viability, and the non-binding control ADCs did not kill either cell line.

Example 11. Anti-PRLR-ADC Cytotoxicity Assay

Figure 9:
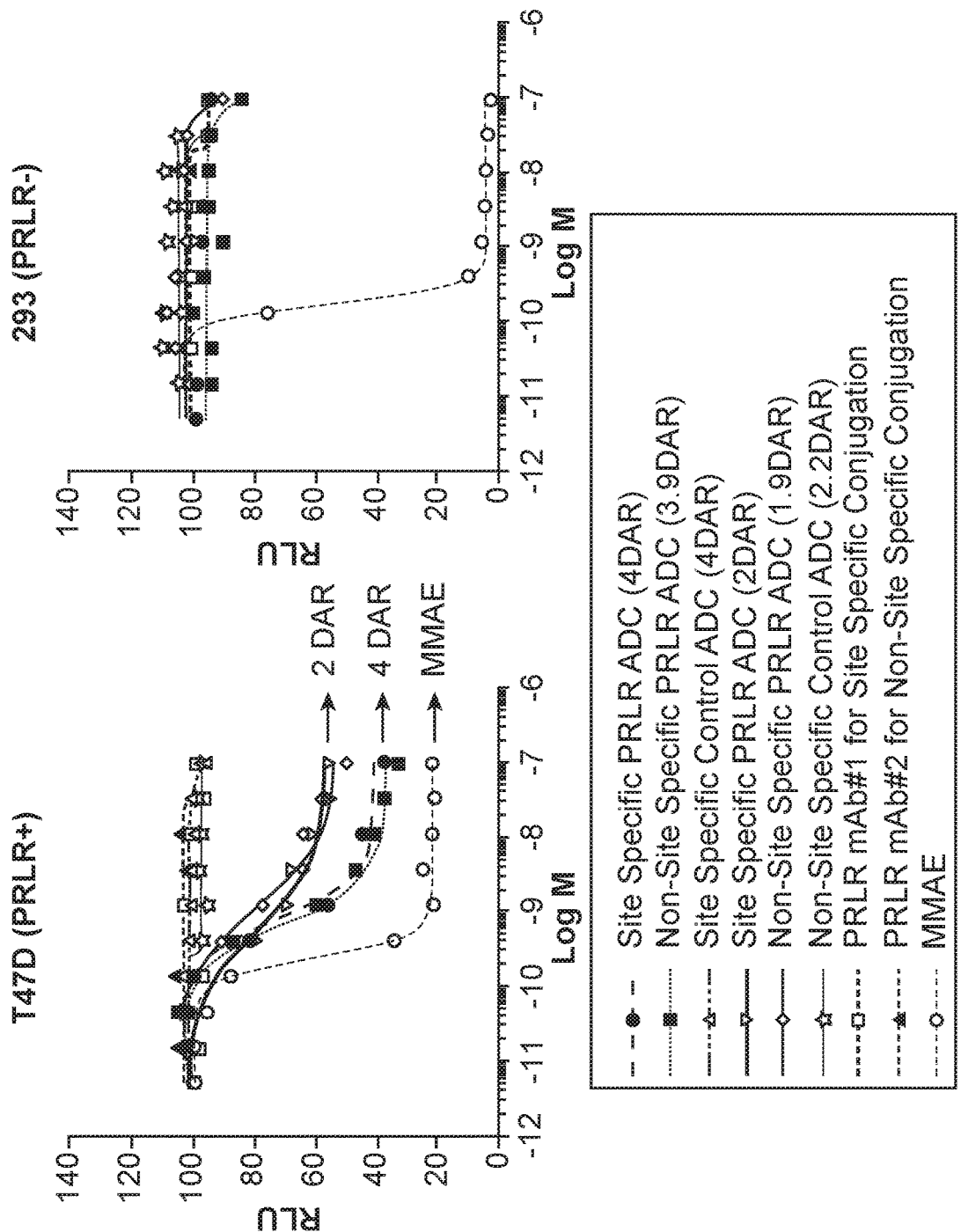
FIG. 9 shows cell killing data for ADCS and controls on T47D cells.
Figure 10A:
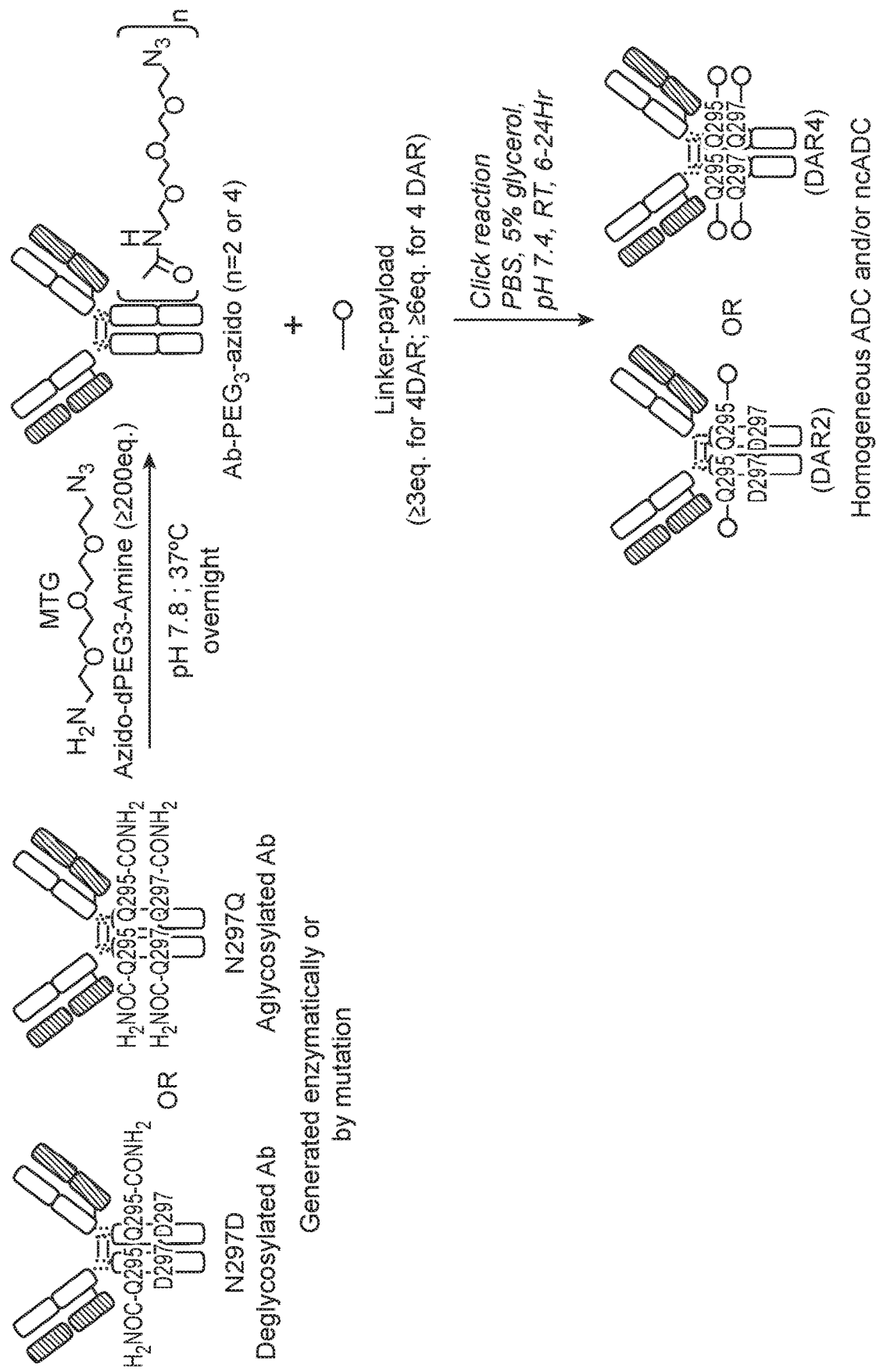
FIGS. 10A and 10B show reaction sequences for transglutaminase-catalyzed formation of a glutaminyl-modified antibody followed by subsequent reaction with a reactive linker-payload compound.
Figure 10B:
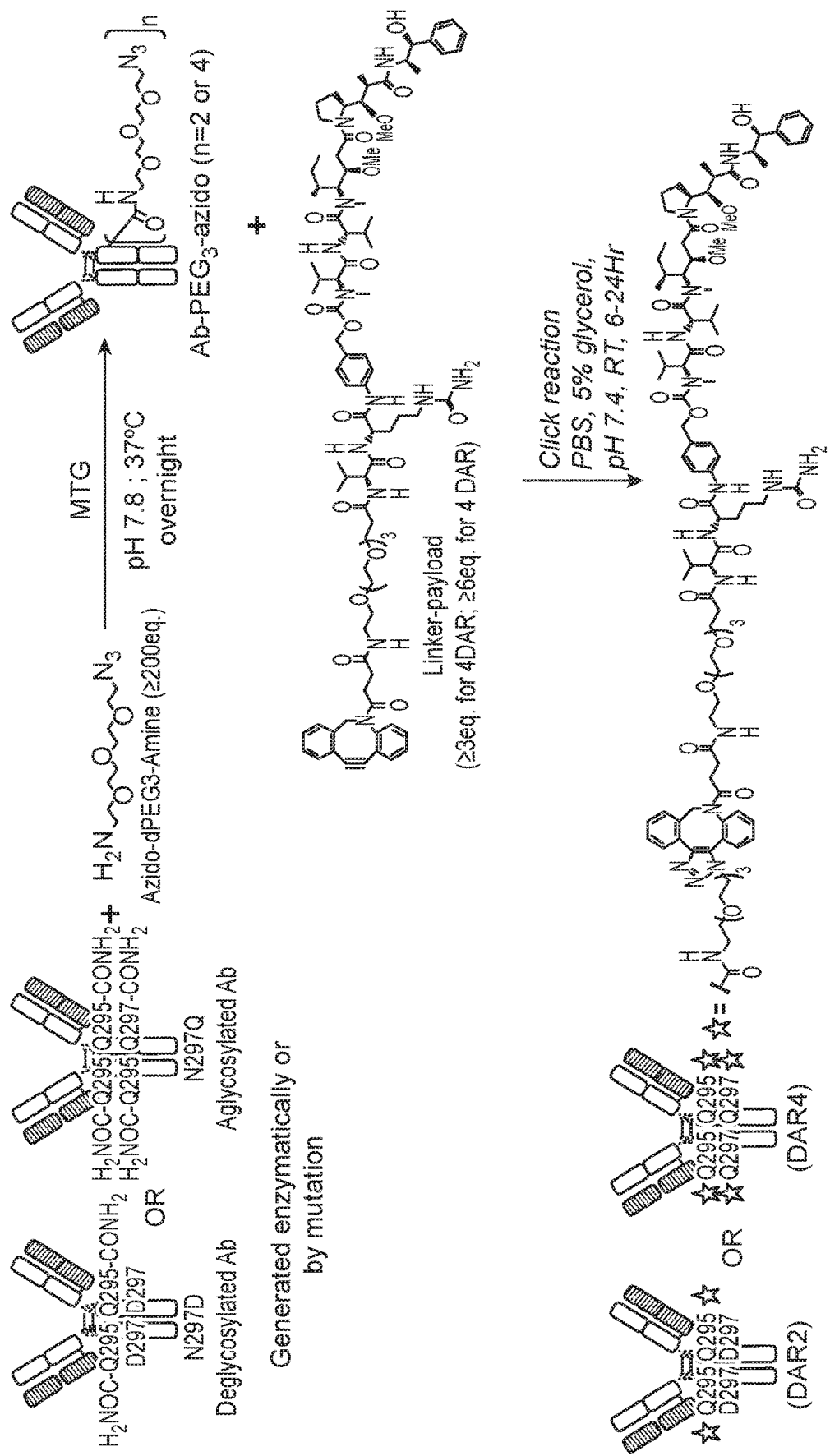

In vitro cytotoxicity of anti-PRLR site-specific ADCs or anti-PRLR conventional thio-maleimide conjugated ADCs were evaluated using the CellTiter-Glo Assay Kit (Promega), which determines the number of viable cells in culture. Cells were seeded in Nunclon (Nunc) white 96-well plates at 1000 (HEK293) or 3000 (T47D) cells/well in complete growth media and grown overnight at 37° C., 5% $CO_2$. For cell viability curves, serially diluted conjugates, naked mAbs, or free payloads were added to the cells at final concentrations ranging from 100 nM to 0.01 nM and incubated for 5 days. Cells were incubated with CellTiter-Glo reagents for 5 min and luminescence was determined on a Victor plate reader (PerkinElmer). $IC_{50}$ values were determined from a four-parameter logistic equation over a 10-point response curve (GraphPad Prism). All curves and $IC_{50}$ values were corrected for payload equivalents. All $IC_{50}$s were expressed as nM and % kill was reported for the highest dose. As summarized in FIG. 9, the anti-PRLR site-specific ADC demonstrated cytotoxicity on T47D cells comparable to the conventional thio-maleimide conjugated ADCs (Example 7) with an $IC_{50}$ of 0.6 nM and 0.9 nM, respectively at DAR=4; with an $IC_{50}$ of 0.6 nM and 1.2 nM, respectively at DAR=2. As expected, the anti-PRLR ADCs had little to no impact on HEK293 viability, and the non-binding control ADCs did not kill either cell line.

All patents, patent application publications, and non-patent literature cited in this specification are herein incorporated by reference as if each individual patent, patent application publication, or non-patent literature document were specifically and individually indicated to be incorporated by reference. While the claimed subject matter has been described in terms of various embodiments, the skilled artisan will appreciate that various modifications, substitutions, omissions, and changes may be made without departing from the scope and spirit thereof.

| SEQUENCE LISTING | |
|---|---|
| <110> | Willian Olson |
| | Amy Han |
| <120> | OPTIMIZED TRANSGLUTAMINASE SITE-SPECIFIC ANTIBODY CONJUGATION |
| <130> | 10179P1 |
| <160> | 4 |
| <170> | FastSEQ for Windows Version 4.0 |
| <210> | 1 |
| <211> | 9 |

SEQUENCE LISTING

<212> PRT

<213> Artificial Sequence

<220>

<223> synthetic

<400> 1

Glu Glu Gln Tyr Asn Ser Thr Tyr Arg
1               5

<210> 2

<211> 11

<212> PRT

<213> Artificial Sequence

<220>

<223> synthetic

<400> 2

Leu Ser Cys Gly Ala Ser Gly Phe Thr Phe Arg
1               5                   10

<210> 3

<211> 238

<212> PRT

<213> Artificial Sequence

<220>

<223> synthetic

<400> 3

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
                20                  25                  30

Pro Thr Asn Tyr Ser Leu Thr Tyr His Arg Glu Gly Glu Thr Leu Met
            35                  40                  45

His Glu Cys Pro Asp Tyr Ile Thr Gly Gly Pro Asn Ser Cys His Phe
        50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

```
Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Glu Gln Lys Leu Ile Ser Glu Glu Asp Leu Gly Gly Glu Gln
    210                 215                 220

Lys Leu Ile Ser Glu Glu Asp Leu His His His His His His
225                 230                 235

<210>   4

<211>   658

<212>   PRT

<213>   Artificial Sequence

<220>

<223>   synthetic

<400>   4

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
            85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
            165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
            245                 250                 255

Phe Glu Ser Met Pro Asn Pro Glu Gly Arg Tyr Thr Phe Gly Ala Ser
            260                 265                 270
```

SEQUENCE LISTING

```
Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
        290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Glu Gln Lys Leu Ile Ser Glu Glu Asp Leu
625                 630                 635                 640

Gly Gly Glu Gln Lys Leu Ile Ser Glu Glu Asp Leu His His His His
                645                 650                 655

His His
```

SEQUENCE LISTING

<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Glu Glu Gln Tyr Asn Ser Thr Tyr Arg
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Leu Ser Cys Gly Ala Ser Gly Phe Thr Phe Arg
1               5                   10

<210> SEQ ID NO 3
<211> LENGTH: 238
<212> TYPE: PRT
<213> ORGANISM: Artificial Sequence
<220> FEATURE:
<223> OTHER INFORMATION: Synthetic

<400> SEQUENCE: 3

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
            20                  25                  30

Pro Thr Asn Tyr Ser Leu Thr Tyr His Arg Glu Gly Glu Thr Leu Met
        35                  40                  45

His Glu Cys Pro Asp Tyr Ile Thr Gly Gly Pro Asn Ser Cys His Phe
    50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Glu Gln Lys Leu Ile Ser Glu Glu Asp Leu Gly Gly Glu Gln
    210                 215                 220

```
Lys Leu Ile Ser Glu Glu Asp Leu His His His His His
225                 230                 235

<210> SEQ ID NO 4
<211> LENGTH: 658
<212> TYPE: PRT
<213> ORGANISM: Artificial Sequence
<220> FEATURE:
<223> OTHER INFORMATION: Synthetic

<400> SEQUENCE: 4

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350
```

```
Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Glu Gln Lys Leu Ile Ser Glu Glu Asp Leu
625                 630                 635                 640

Gly Gly Glu Gln Lys Leu Ile Ser Glu Glu Asp Leu His His His
                645                 650                 655

His His
```

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Deamidated asparagine

<400> SEQUENCE: 5

```
Glu Glu Gln Tyr Asn Ser Thr Tyr Arg
1               5
```

<210> SEQ ID NO 6

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Linker
<220> FEATURE:
<221> NAME/KEY: MOD_RES
<222> LOCATION: (5)..(5)
<223> OTHER INFORMATION: Deamidated asparagine

<400> SEQUENCE: 6

Glu Glu Gln Tyr Asn Ser Thr Tyr Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Linker
<220> FEATURE:
<221> NAME/KEY: MOD_RES
<222> LOCATION: (5)..(5)
<223> OTHER INFORMATION: Linker

<400> SEQUENCE: 7

Glu Glu Gln Tyr Gln Ser Thr Tyr Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Glu Glu Gln Tyr Gln Ser Thr Tyr Arg
1               5
```

What is claimed is:

1. A method of producing a glutaminyl-modified antibody comprising:

(a) reacting, in a mixture, a deglycosylated antibody or aglycosylated IgG antibody, with at least 200 molar equivalents of a primary amine compound to provide at least a 97.5% drug occupancy relative to the number of sites available, according to:

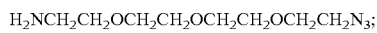

$H_2NCH_2CH_2OCH_2CH_2OCH_2CH_2OCH_2CH_2N_3;$ in the presence of transglutaminase at a pH between 7.6±0.05 and 7.8±0.05 for at least 4 hr, wherein antibody is first added to the mixture, followed by primary amine, and finally transglutaminase, at a temperature between about 25° C. and about 40° C.

2. The method of claim 1 wherein the primary amine compound of step (a) is at a concentration of at least 50 molar equivalents compared to the deglycosylated antibody or aglycosylated antibody.

3. The method of claim 1 wherein the primary amine compound of step (a) is at a concentration of at least 100 molar equivalents compared to the deglycosylated antibody or aglycosylated antibody.

4. The method of claim 1 wherein the primary amine compound of step (a) is at a concentration of at least 200 molar equivalents compared to the deglycosylated antibody or aglycosylated antibody.

5. The method of claim 1, wherein the transglutaminase of step (a) is present at 1 to 30 U per milligram of deglycosylated antibody or aglycosylated antibody.

6. The method of claim 1, wherein the transglutaminase of step (a) is present at least at 2.5 U per milligram of deglycosylated antibody or aglycosylated antibody.

7. The method of claim 1, wherein the transglutaminase of step (a) is present at least at 10 U per milligram of deglycosylated antibody or aglycosylated antibody.

8. The method of claim 1, wherein the transglutaminase of step (a) is present at about 25 U per milligram of deglycosylated antibody or aglycosylated antibody.

9. The method of claim 1, wherein the reaction of step (a) is at a pH of 7.6±0.05.

10. The method of claim 1, wherein the reaction of step (a) is at a pH of 7.7±0.05.

11. The method of claim 1, wherein the reaction of step (a) is at a pH of 7.8±0.05.

12. The method of claim 1, wherein the transglutaminase of step (a) is a microbial transglutaminase.

13. The method of claim 1, wherein step (a) is conducted for at least 18 hours.

14. The method of claim 1, wherein step (a) is conducted for at least 24 hours.

15. The method of claim 1, wherein the antibody is deglycosylated with peptide N-glycosidase F (PNGaseF) prior to step (a).

16. The method of claim 1, wherein the antibody is aglycosylated.

17. The method of claim 1, wherein step (a) is conducted in one or more solvent(s) selected from the group consisting of water, buffered water, saline water, buffered saline water, and an organic solvent.

18. The method of claim 1, wherein step (a) is conducted in water buffered with phosphate, HEPES, or MOPS.

19. A glutaminyl-modified antibody produced by the method of claim 1.

20. The method of claim 1, further comprising:
(b) purifying the glutaminyl-modified antibody via affinity chromatography or protein A chromatography.

21. The method of claim 20, further comprising
(c) reacting the glutaminyl-modified antibody with a reactive payload compound to form an antibody-payload conjugate.

22. The method of claim 20, further comprising
(c) reacting the glutaminyl-modified antibody with a reactive linker-payload compound to form an antibody-linker-payload conjugate.

23. The method of claim 20, further comprising
(c) reacting the glutaminyl-modified antibody with a reactive linker compound to form an antibody-linker conjugate; and
(d) reacting the antibody-linker conjugate with a reactive payload compound to form an antibody-linker-payload conjugate.

24. The method of claim 1, that provides less than 10% side product, relative to desired antibody conjugates.

25. A pharmaceutical composition comprising the antibody of claim 1 and one or more pharmaceutically acceptable diluents, excipients, or carriers.

26. A method of treating a condition in a subject in need thereof comprising administering to the subject a pharmaceutically acceptable amount of the antibody of claim 1.

27. The method of claim 26, wherein the condition is cancer.

28. The method of claim 1, wherein the antibody comprises a modification at HC Q295.

29. The method of claim 1, wherein the antibody comprises a HC N297Q modification.

30. A method of producing a glutaminyl-modified antibody comprising:
(a) reacting in a mixture a deglycosylated antibody or aglycosylated IgG antibody, with at least 200 molar equivalents of a primary amine compound to provide a DAR of at least 4.0, according to:

$H_2NCH_2CH_2OCH_2CH_2OCH_2CH_2OCH_2CH_2N_3$;

in the presence of transglutaminase at a pH between 7.6±0.05 and 7.8±0.05 for at least 4 hr, wherein antibody is first added to the mixture after, followed by primary amine, and finally transglutaminase at a temperature between about 25° C. and about 40° C.

31. The method of claim 1, wherein the reaction of step (a) is between pH of 7.6 to 7.8.

32. The method of claim 30, wherein the reaction of step (a) is between pH of 7.6 to 7.8.

* * * * *